US006828427B1

(12) United States Patent
Hebert

(10) Patent No.: US 6,828,427 B1
(45) Date of Patent: Dec. 7, 2004

(54) OLIGOMERIC AMINODIOL-CONTAINING COMPOUNDS, LIBRARIES THEREOF, AND PROCESS OF PREPARING THE SAME

(75) Inventor: Normand Hebert, Cardiff, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 08/973,381

(22) PCT Filed: Jun. 7, 1996

(86) PCT No.: PCT/US96/09604

§ 371 (c)(1),
(2), (4) Date: Mar. 25, 1998

(87) PCT Pub. No.: WO96/40672

PCT Pub. Date: Dec. 19, 1996

Related U.S. Application Data

(63) Continuation-in-part of application No. 08/483,311, filed on Jun. 7, 1995, now Pat. No. 6,184,389, which is a continuation-in-part of application No. PCT/US95/00356, filed on Jan. 11, 1995, which is a continuation-in-part of application No. 08/180,134, filed on Jan. 11, 1994, now Pat. No. 5,519,134, which is a continuation-in-part of application No. 08/179,970, filed on Jan. 11, 1994, now Pat. No. 6,448,373.

(51) Int. Cl.$^7$ .................. C07H 21/00; A61K 38/00; C07K 17/00; C12Q 1/68
(52) U.S. Cl. .................. 536/23.1; 536/25.3; 530/300; 530/333; 435/6
(58) Field of Search .................. 536/23.1, 25.3; 530/300, 333, 350; 435/6; 436/501; 514/2, 44

(56) References Cited

U.S. PATENT DOCUMENTS

| | | | |
|---|---|---|---|
| 3,687,808 A | 8/1972 | Merigan, Jr. et al. | 195/28 |
| 3,856,835 A | 12/1974 | Guillot | 260/429.9 |
| 4,958,013 A | 9/1990 | Letsinger | 536/27 |
| 5,144,045 A | 9/1992 | Wissner et al. | 549/219 |
| 5,210,264 A | 5/1993 | Yau | 558/167 |
| 5,212,295 A | 5/1993 | Cook | 536/26.7 |
| 5,218,105 A | 6/1993 | Cook et al. | 536/25.31 |
| 5,288,514 A | 2/1994 | Ellman | 427/2 |
| 5,324,483 A | 6/1994 | Cody et al. | 422/131 |
| 5,419,966 A | 5/1995 | Reed et al. | 428/406 |

FOREIGN PATENT DOCUMENTS

| | | |
|---|---|---|
| WO | WO 87/01374 | 3/1987 |
| WO | WO 91/12331 | 8/1991 |
| WO | WO 91/13080 | 9/1991 |
| WO | WO 91/19735 | 12/1991 |
| WO | WO 92/02532 | 2/1992 |
| WO | WO 92/03568 | 3/1992 |
| WO | WO 92/05186 | 4/1992 |
| WO | WO 93/04204 | 3/1993 |
| WO | WO 93/07883 | 4/1993 |
| WO | WO 93/15221 | 8/1993 |
| WO | WO 94/08051 | 4/1994 |
| WO | WO 94/24314 | 10/1994 |
| WO | WO 94/26775 | 11/1994 |
| WO | WO 94/27719 | 12/1994 |
| WO | WO 94/28028 | 12/1994 |
| WO | WO 94/28424 | 12/1994 |
| WO | WO 95/18623 | 7/1995 |
| WO | WO 95/18820 | 7/1995 |

OTHER PUBLICATIONS

Cloudsdale, I.S. et al., "Synthetic Studies in the Ajmaline Series", *J. Org. Chem.*, 1982, 47, 919–928.

Davies, H.M.L. et al., "Divergent Pathways in the Intramolecular Reactions between Rhodium–Stabilized Vinylcarbenoids and Pyrroles: Construction of Fused Tropanes and 7–Azabicyclo[4.2.0]Octadienes", *J. Org. Chem.*, 1996, 61, 2305–2313.

Verschueren, K. et al., "A Facile Synthesis of 1,2,3, 4–Tetrahydro–7–hydroxyisoqunoline–3–carboxylic Acid, a Conformationally Constrained Tyrosine Analogue", *Synthesis*, 1992, 458–460.

Atherton et al., "The Fluorenylmethoxycarbonyl Amino Protecting Group", Chapter 1 in *The Peptides*, Gross and Meienhofer, Eds., Academic Press, New York, 1987, 9, 1–38.

Augustyns, K. et al., "Influence of the Incorporation of (S)–9–(3,4–dihydroxy–butyl) adenine on the Enzymatic Stability and Base–Pairing Properties of Oligodeoxynucleotides", *Nucl. Acids Res.*, 1991, 19(10), 2587–2593.

Carell, T. et al., "A Novel Procedure for the Synthesis of LIbraries Containing Small Organic Molecules", *J. Angew. Chem. Int. Ed. Engl.*, 1994, 33, 2059–2061.

Carell, T. et al., "A Solution–Phase Screening Procedure for the Isolation of Active Compounds from a Library of Molecules", *Angew. Chem. Int. Ed. Engl.*, 1994, 33, 2061–2064.

Chen et al., "Analagous Organic Synthesis of Small–Compound Libraries: Validation of Combinatorial Chemistry in Small–Molecule Synthesis", *J. Am. Chem. Soc.*, 1994, 116, 2661–2662.

Cossy, J. et al., "Formation of Optically Active 3–Hydroxypiperidines", *Tetrahedron Letters*, 1995, 36(4), 549–552.

DeWitt, S. et al., "Diversomers": An Approach to Nonpeptide Nonoligomeric Chemical Diversity. *PNAS USA*, 1993, 90, 6909–6913.

Ezquerra, J. et al., "Short and Efficient Enantioselective Synthesis of cis and trans Pyrrolidine–2.5 Dicarboxylic Acids", *Tetrahedron Letters*, 1993, 34(31), 4989–4992.

Garegg, P. et al., "Nucleoside Hydrogenphosphonates in Oligonucleotide Synthesis", *Chemica Scripta*, 1986, 26, 159–62.

(List continued on next page.)

*Primary Examiner*—Ardin H. Marschel
(74) *Attorney, Agent, or Firm*—Woodcock Washburn LLP

(57) ABSTRACT

Oligomeric compounds comprising a plurality of aminodiol monomer subunits joined by linking groups are provided, as well as libraries of such compounds and processes for preparing the oligomeric compounds and libraries.

14 Claims, 2 Drawing Sheets-

OTHER PUBLICATIONS

Farooqui, F. et al., "Effect of Structural Variations in Cholesteryl–Conjugated Oligonucleotides on Inhibitory Activity towards HIV–1", *Bioconjugate Chem.,* 1991, 2, 422–426.

Froehler, B., "Deoxynucleoside H–Phosphonate Diester Intermediates in the Synthesis of Internucleotide Phosphate Analogues", *Tetrahedron Letters,* 1986, 27(46), 5575–5578.

Froehler, B. et al., "Nucleoside H–Phosphonates: Valuable Intermediates in the Synthesis of Deoxyoligonucleotides", *Tetrahedron Letters,* 1986, 27(4), 469–472.

Gryaznov, S.M. and Sokolova, N.I., "A New Method for the Synthesis of Oligodeoxynucleotides Containing Internucleotide Phosphoramidate Bonds", *Tetrahedron Letters,* 1990, 31. 3205–3208.

Gryaznov, S. and Potapov, "A New Approach to the Synthesis of Oligodeoxyribonucleotides with Alkylamino Groups Linked to Internucleotide Phosphate Groups", *Tetrahedron Letters,* 1991, 32(30), 3715–3718.

Hebert et al., "Synthesis of N–Substituted Hydroxyprolinol Phosphoramidites for the Preparation of Combinatorial Libraries", *Tetrahedron Lett.,* 1994, 35(51), 9509–9512.

Iso, Y. et al., "Synthesis of Viologen–tagged Oligodeoxynucleotides", *Tetrahedron Letters,* 1992, 33(4), 503–506.

Jung, P. et al., "Hybridization of Alternating Cationic/Anionic Oligonucleotides to RNA Segments", *Nucleosides & Nucleotides,* 1994, 13(6&7), 1597–1605.

Letsinger, R. et al., "Cationic Oligonucleotides", *J. Am. Chem. Soc.,* 1988, 110, 4470–4471.

Look, G. et al., "Trimethylorthoformate: A Mild and Effective Dehydrating Reagent for Solution and Solid Phase Imine Formation", *Tetrahedron Letters,* 1995, 36(17), 2937–2940.

Ohlmeyer, M. et al., "Complex Synthetic Chemical Libraries Indexed With Molecular Tags", *PNAS USA,* 1993, 90, 19022–10926.

Peterson et al., "Synthesis and Biological Evaluation of 4–Purinylpyrrolidine Nucleosides", *J. Med. Chem.,* 1991, 34, 2787–2797.

Pon, R.T., "Solid–Phase Supports in Oligonucleotide Synthesis", Protocols for Oligonucleotides and Analogs: Synthesis and Properties, Chapter 19, Agrawal, S., Ed., Humana Press, 1993.

Ritter, A. and Miller, "Amino Acid–Derived Chiral Acyl Nitroso Compounds: Diastereoselectivity in Intermolecular Hetero Diels–Alder Reactions", *J. Org. Chem.,* 1994, 59, 4602–4611.

Ritter, A. and Miller, "Asymmetric Syntheses of Novel Amino Acids and Peptides from Acylnitroso–Derived Cycloadducts", *Tetrahedron Letters,* 1994, 35(50), 9379–9382.

Saab, N. et al., "Synthesis and Evaluation of Unsymmetrically Substituted Polyamine Analogues as Modulators of Human Spermidine Spermine–$N^1$–Acetyltransferase (SSAT) and as Potential Antitumor Agents", *J. Med. Chem.,* 1993, 36, 2998–3004.

Samukov, V. et al., "2–(4–Nitrophenyl) sulfonylethoxycarbonyl(Nsc) Group as a Base–Labile α–Amino Protection for Solid Phase Peptide Synthesis", *Tetrahedron Letters,* 1994, 35(42), 7821–7824.

Simon, R. et al., "Peptoids: A Modular Approach to Drug Discovery", *PNAS USA,* 1992, 89, 9367–9371.

Takahashi et al., "Preparation of New Chiral Pyrrolidine–ebisphosphines as Highly Effective Ligands for Catalytic Assymetic Synthesis of R–(–)–Pantolactone", *Tetra Lett.,* 1986, 27(37), 4477–4480.

Takeda et al., "Practical Asymmetric Synthesis of (R)–(–)–Phenylephrine Hydrochloride Catalyzed by (2R, 4R)–MC-CPM–Rhodium Complex", *Tetra. Lett.,* 1989, 30(3), 367–370.

Verhart, C.G. and Tesser, "New Base–labile Amino–protective Groups for Peptide Synthesis", *Recueil des Travaux Chimiques des Pay–Bas,* 1988, 107, 621–626.

Zuckermann, R. et al., "Efficient method for the preparation of peptoids [oligo(N–substituted glycines)] by submonomer solid–phase synthesis", *J. Am. Chem. Soc.,* 1992, 114, 10646–10647.

Achari, et al., "Facing up to Membranes: Structure Function Relationships in Phospholipases", *Cold Spring Harbor Symposia on Quantitative Biology,* 1987, L11, 441–452.

Agrawal, S., ed., "Protocols for Oligonucleotides and Analogs", Humana Press, New Jersey, 1993.

Alul, et al., "Oxalyl–CPG: A Liable Support for Synthesis of Sensitive Oligonucleotide Derivatives", *Nucl. Acids Res.,* 1991, 19, 1527–1532.

Beaucage et al., "Advances in the Synthesis of Oligonucleotides by the Phosphoramidite Approach", *Tetra. Lett.,* 1992, 48, 2223–2311.

Bodanszky, M., "Principles of Peptide Synthesis", Springer–Verlag, Berlin–New York, 1984.

Bomalaski, J. et al., "Human extracellular recombinant phospholipase A, induces an inflammatory response in rabbit joints", *J. Immunology,* 1991, 146, 3904–3910.

Bouzard, D. et al., "Fluoronaphthyridines and quinolones as antibacterial agents. 2. synthesis and structure–Activity relationships of new 1–tert–butyl 7–substituted derivatives", *J. Med. Chem.,* 1990, 33, 1344–1352.

Braish, T. et al., "Synthesis of (S,S)–and (r,R)–2–Alkyl–2.5–diazabicyclo[2.21]heptanes", *J. Org. Chem.,* 1990, 55, 1684–1687.

Bridges, R. et al., "Conformationally defined neurotransmitter analogues. Selective inhibition of glutamate uptake by one pyrrolidine–2,4–dicarboxylate diastereomer", *J. Med. Chem.,* 1991, 34, 717–725.

Burack, W. et al., "Role of lateral phase separation in the modulation of phospholipase $A_2$ activity", *Biochemistry,* 1993, 32, 583–589.

Campbell, et al., "Inhibition of Phospholipase $A_2$: a Molecular Recognition Study", *J. Chem. Soc., Chem. Commun.,* 1998, 1560–1562.

Cho et al., "The Chemical Basis for Interfacial Activation of Monomeric Phospholipases $A_2$", *J. Biol. Chem.,* 1988, 263, 11237–11241.

Cooper et al., "A Route of Optically Active Trisubstituted Pyrrolidine using Claisen Rearrangements of Azalctones", *Tetrahedron Letters,* 1987, 28, 3031–3034.

Davidson et al., "1–Stearyl,2–Stearoylaminodeoxy Phosphatidylcholine, A Potent Reversible Inhibitor Of Phospholipase $A_2$", *Biochem. Biophys. Res. Commun.,* 1986, 137, 587–592.

Davidson et al., "Inhibition of Phospholipase $A_2$ by "Lipocortins" and Calpactins", *J. Biol. Chem.,* 1987, 262, 1698–1705.

Dennis, "Phospholipases", in "The Enzymes", Boyer, P.D., ed., Academic Press, 1983, vol. 16, Chapter 9, pp. 307–353.

Ecker, et al., "Rational Screening of Oligonucleotide Combinatorial Libraries for Drug Discovery", *Nucl. Acids Res.*, 1993, 21, 1853–1856.

Englisch, U. and Gauss, D.H., "Chemically Modified Oligonucleotides as Probes and Inhibitors", *Angewande Chemie, Int. Ed.*, 1991, 30, 613–629.

Franson, et al. "Phospholipid metabolism by phagocytic cells. Phospholipases $A_2$ associated with rabbit polymorphonuclear leukocyte granules", *J. Lipid Res.*, 1974, 15, 380–388.

Freeman, J.P., ed., "Reduction of alpha–amino Acids: L–Valinol", in *Organic Syntheses*, New York: John Wiley & Sons, Inc., 530–533, 1990.

Gait, M.J., ed., *Oligonucleotide Synthesis, A Practical Approach*, Oxford: IRL Press, 1984.

Geysen, et al., "Strategies for epitope analysis using peptide synthesis", *J. Immun. Meth.*, 1987, 102, 259–274.

Glaser, et al., "Phospholipase $A_2$ enzymes: regulation and inhibition", *TIPS Review*, 1993, 14, 92–98.

Grainger, et al., "An enzyme caught in action: direct imaging of hydrolytic function and domain formation of phospholipase $A_2$ in phosphatidylcholine monolayers", *FEBS Letters*, 1989, 252, 73–82.

Green et al. in "Protective Groups in Organic Synthesis", 2nd Ed., John Wiley & Sons, New York, 1991.

Houghten, et al., "Generation and use of synthetic peptide combinatorial libraries for basic research and drug discovery", *Nature*, 1991, 354, 84–86.

Jaeger, et al., "Pyrrolidinediols. 1–Substituted 3–Hydroxymethyl–4–hydroxypyrrolidines and Derivatives", *J. Organic Chem.*, 1965, 30, 740–744.

Jordis, U. et al., "Synthesis of (1R,4R)–and (1S, 4S)–2.5–diazabicyclo[2.2.1]heptanes and their n–substituted derivatives", *Synthesis*, 1990, 925–930.

Kroschwitz, J.I., "Polynucleotides", in "Concise encyclopedia of polymer science and engineering", 1990, *Wiley–Interscience Publication*, 858–859.

Lombardo et al., "Cobra Venom Phospholipase $A_2$ Inhibition by Manoalide", *J. Biol. Chem.*, 1985, 260, 7234–7240.

Märki, F. et al., "Differential inhibition of human secretory and cytosolic phospholipase $A_2$", *Agents Actions*, 1993, 38, 202–211.

McKennon, M.J. and Meyers, A.I., "A Convenient Reduction of Amino Acids and Their Derivatives", *J. Org. Chem.*, 1993, 58, 3568–3571.

Mellor, D.P., "Chemistry of Chelation and Chelating Agents in International Encyclopedia of Pharmacology and Therapeutics", Section 70, "The Chelation of Heavy Metals", Levine, W.G., ed., New York, Pergamon Press, 1979.

Miyake, A. et al., "The Novel Natural Product YM–26567–1 [(–)–trans–4–(3–dodecanoyl–2,4,6–trihydroxyphenyl)–7–hydroxy–2–(4–hydroxyphenyl) chroman]: A Competitive Inhibitor of Group II Phospholipase $A_2$", *J.Pharm.Exp.Therap.*, 1992, 263, 1302–1307.

Noel, J.P. et al., "Phospholipase $A_2$ Engineering. 3. Replacement of Lysine–56 by Neutral Residues Improves Catalytic Potency Significantly, Alters Substrate Specificity, and Clarifies the Mechanism of Interfacial Recognition", *J. Am. Chem. Soc.*, 1990, 112, 3704–3706.

Oinuma, H. et al., "Synthesis and biological evaluation of substituted benzenesulfonamides as novel potent membrane–bound phospholipase $A_2$ inhibitors", *J. Med. Chem.*, 1991, 34, 2260–2267.

Owens, R. et al., "The rapid identification of HIV protease inhibitors through the synthesis and screening of defined peptide mixtures", *Biochem. & Biophys. Res.*, 1991, 181(1), 402–408.

Pruzanski et al., "Enzymatic Activity and Immunoreactivity of Extracellular Phospholipase $A_2$ in Inflammatory Synovial Fluids", *Inflammation*, 1992, 16, 451–457.

Remuzon et al., "Preparation of (6R)–(1R, 4R)–6–Methyl–2–(p–Toluene–sulfonyl)–5–Phenylmethyl–2.5–Siazabicyclo[2.2.1]Heptanes, Intermediates in a synthesis of New Quinolones", *Heterocycles*, 1992, 34(2), 241–245.

Remeuzon et al., "Synthesis of (1R,4R,7S)– and (1S,4S,7S)–2–(4–Tolysulfony))–5–phenylmethyl–7–methyl–2.5–diaabicyclo[2.2.1]heptanes via Regioselective opening of 3,4–Epoxy–D–proline with Lithium Dimethyl Cuprate", *J. Heterocyclic Chem.*, 1993, 30, 517–523.

Rosen et al., "Design, synthesis, and properties of (4S)–7–(4–Amino–2–substituted–pyrrolidin–1–yl) quinolone–3–carboxylic acids", *J. Med. Chem.*, 1988, 31, 1598–1611.

Scott, David L. et al., "Interfacial Catalysis: The Mechanism of phospholipase $A_2$", *Science*, 1990, 250, 1541–1546.

Tanaka et al., "A novel type of phospholipsaw $A_2$ inhibitor, thjielocin A1B, and mechanism of action", *J. Antibiotics*, 1992, 45(7), 1071–1078.

Vishwanath, B.S. et al., "Edema–inducing activity of phospholipase $A_2$ purified from human synovial fluid and inhibition by aristolochic acid", *Inflammation*, 1998, 12(6), 549–561.

Washburn, W.N. and Dennis, E.A., "Suicide–inhibitory Bifunctionally linked Substrates (SIBLINKS) as phospholipase $A_2$ Inhibitors", *Biol. Chem.*, 1991, 266(8), 5042–5048.

Wery et al., "Structure of recombinant human rheumatoid arthritic synovial fluid phospholipase $A_2$ at 2.2 Å resolution", *Nature*, 1991, 342, 79–82.

Wright et al., "Large scale synthesis of oligonucleotides via phosphoramidite nucleosides and a high–loaded polystyrene support", *Tetrahedron Letters*, 1993, 34(21), 3373–3376.

Wyatt et al., "Combinatorially selected guanosine–quartet structure is a potent inhibitor of human immunodeficiency virus envelope–mediated cell fusion", *Proc. Natl. Acad. Sci. USA*, 1994, 91, 1356–1360.

Yang, C. and Chang, L., "Studies on the status of lysine residues in phospholipase $A_2$ from Naja naja atra (Taiwan cobra) snake venom", *Biochem. J.*, 1989, 262, 855–860.

Yuan, W. et al., "Synthesis and evaluation of phospholipid analogues as inhibitors of cobra venom phospholipase $A_2$", *J. Am. Chem. Soc.*, 1987, 109, 8071–8081.

"Pyrrolidine Derivatives", *Chem. Abstracts* 1987, 106:213757w, p. 644.

Ko, S.Y. et al., "p–Nitrobenzoate esters of epoxy alcohols: Convenient synthons for water–soluble epoxy alcohols", *J. Orig. Chem.*, 1987, 52, 667–671.

Ko, S.Y. and Sharpless, K.B., "In situ opening of epoxy alcohols: A convenient alternative to the isolation of unstable epoxy alcohols", *J. Org. Chem.*, 1986, 51, 5413–5415.

Hanson, R.M., "The synthetic methodology of nonracemic glycidol and related 2.3–epoxy alcohols", *Chemical Reviews*, 1991, 91(4), 437–475.

Klunder et al., "Asymmetric Epoxidation of Allyl Alcohol: Efficient Routes to Homochiral β–Adrenergic Blocking Agents", *J. Org. Chem.,* 1986, 3710–3712.

Klunder et al., "Arenesulfonate Derivatives of Homochiral Glycidol: Versatile Chiral Building Blocks for Organic Synthesis", *J. Org. Chem.,* 1989, 54, 1295–1304.

Misiura et al., "Biotinyl and Phosphotyrosinyl Phosphoramidite Derivatives Useful in the Incorporation of Multiple Reporter Groups on Synthetic Oligonucleotides", *Nuclei Acids Res.,* 1990, 18, 4345–4354.

Ramirez et al., "Nucleotidophospholipids: Oligonucleotide Derivatives with Membrane–Recognition Groups", *J. Am. Chem. Soc.,* 1982, 104(20), 5483–5486.

Telser et al., "Synthesis and characterization of DNA oligomers and duplexes containing covalently attached molecular labels: comparison of biotin, fluorescein, and pyrene labels by thermodynamic and optical spectroscopic measurements", *J. Am. Chem. Soc.,* 1989, 111, 6966–6976.

OLIGOMERIC AMINODIOL-CONTAINING COMPOUNDS, LIBRARIES THEREOF, AND PROCESS OF PREPARING THE SAME

CROSS REFERENCE TO RELATED APPLICATIONS

This application is a continuation-in-part of U.S. application Ser. No. 08/483,311, filed Jun. 7, 1995, now U.S. Pat. No. 6,184,389, which is a continuation-in-part of International patent application Serial No. PCT/US95/00356 filed Jan. 11, 1995, which is a continuation-in-part of U.S. application Ser. No. 08/180,134, filed Jan. 11, 1994, now U.S. Pat. No. 5,519,134, which is a continuation in part of U.S. application Ser. No. 08/179,970, filed Jan. 11, 1994, which issued on Sep. 10, 2002 as U.S. Pat. No. 6,448,373. Each of these patent applications are assigned to the assignee of this application and are incorporated by reference herein.

BACKGROUND OF THE INVENTION

Traditional processes of drug discovery involve the screening of complex fermentation broths and plant extracts for a desired biological activity or the chemical synthesis of many new compounds for evaluation as potential drugs. The advantage of screening mixtures from biological sources is that a large number of compounds are screened simultaneously, in some cases leading to the discovery of novel and complex natural products with activity that could not have been predicted otherwise. The disadvantages are that many different samples must be screened and numerous purifications must be carried out to identify the active component, often present only in trace amounts. On the other hand, laboratory syntheses give unambiguous products, but the preparation of each new structure requires significant amounts of resources. Generally, the de nova design of active compounds based on the high resolution structures of enzymes has not been successful.

It is thus now widely appreciated that combinatorial libraries are useful per se and that such libraries and compounds comprising them have great commercial importance. Indeed, a branch of chemistry has developed to exploit the many commercial aspects of combinatorial libraries.

In order to maximize the advantages of each classical approach, new strategies for combinatorial deconvolution have been developed independently by several groups. Selection techniques have been used with libraries of peptides (Geysen, H. M., Rodda, S. J., Mason, T. J., Tribbick, G. and Schoofs, P. G., *J. Immun. Meth.* 1987, 102, 259–274; Houghten, R. A., Pinilla, C., Blondelle, S. E., Appel, J. R., Dooley, C. T. and Cuervo, J. H., *Nature*, 1991, 354, 84–86; Owens, R. A., Gesellchen, P. D., Houchins, B. J. and DiMarchi, R. D., *Biochem. Biophys. Res. Commun.*, 1991, 181, 402–408; Doyle, M. V., PCT WO 94/28424; Brennan, T. M., PCT WO 94/27719); nucleic acids (Wyatt, J. R., et al., *Proc. Natl. Acad. Sci. USA*, 1994, 91, 1356–1360; Ecker, D. J., Vickers, T. A., Hanecak, R., Driver, V. and Anderson, K., *Nucleic Acids Res.*, 1993, 21, 1853–1856); nonpeptides and small molecules (Simon, R. J., et al., *Proc. Natl. Acad. Sci. USA*, 1992, 89, 9367–9371; Zuckermann, R. N., et al., *J. Amer. Chem. Soc.*, 1992, 114, 10646–10647; Bartlett, Santi, Simon, PCT W091/19735; Ohlmeyer, M. H., et al., *Proc. Natl. Acad. Sci. USA*, 1993, 90, 10922–10926; DeWitt, S. H., Kiely, J. S., Stankovic, C. J., Schroeder, M. C. Reynolds Cody, D. M. and Pavia, M. R., *Proc. Natl. Acad. Sci. USA*, 1993, 90, 6909–6913; Cody et al., U.S. Pat. No. 5,324,483; Houghten et al., PCT WO 94/26775; Ellman, U.S. Pat. No. 5,288,514; Still et al., PCT WO 94/08051; Kauffman et al., PCT WO 94/24314; Carell, T., Wintner, D. A., Bashir-Hashemi, A. and Rebek, J., *Angew. Chem. Int. Ed. Engel.*, 1994, 33, 2059–2061; Carell, T., Wintner, D. A. and Rebek, J., *Angew. Chem. Int. Ed. Engel.*, 1994, 33, 2061–2064; Lebl, et al., PCT WO 94/28028). A review of the above references reveals that the most advanced of these techniques are those for selection of peptides and nucleic acids. Several groups are working on selection of heterocycles such as benzodiazepines. With the exception of Rebek et al., scant attention has been given to combinatorial discovery of other types of molecules.

The majority of the techniques reported to date involve iterative synthesis and screening of increasingly simplified subsets of oligomers. Monomers or sub-monomers that have been utilized include amino acids, amino acid-like molecules, i.e. carbamate precursors, and nucleotides, both of which are bifunctional. Utilizing these techniques, libraries have been assayed for activity in either cell-based assays, or for binding and/or inhibition of purified protein targets.

A technique, called SURF™ (Synthetic Unrandomization of Randomized Fragments), involves the synthesis of subsets of oligomers containing a known residue at one fixed position and equimolar mixtures of residues at all other positions. For a library of oligomers four residues long containing three monomers (A, B, C), three subsets each containing 27 compounds would be synthesized (NNAN, NNBN, NNCN, where N represents equal incorporation of each of the three monomers). Each subset is then screened in a functional assay and the best subset is identified (e.g. NNAN). A second set of subsets is synthesized and screened, each containing the fixed residue from the previous round, and a second fixed residue (e.g. ANAN, BNAN, CNAN, each containing 9 molecules). Through successive rounds of screening and synthesis, a unique sequence with activity in the functional assay can be identified. The SURF™ technique is described in Ecker, D. J., Vickers, T. A., Hanecak, R., Driver, V. & Anderson, K., *Nucleic Acids Res.*, 1993, 21, 1853–1856. The SURF™ method is further described in PCT patent application WO 93/04204, the entire disclosure of which is herein incorporated by reference.

The combinatorial chemical approach that has been most utilized to date, utilizes an oligomerization from a solid support using monomeric units and a defined connecting chemistry, i.e. a solid support monomer approach. This approach has been utilized in the synthesis of libraries of peptides, peptoids, carbamates and vinylogous peptides connected by amide or carbamate linkages or nucleic acids connected by phosphate linkages as exemplified by the citations in previous paragraphs above. A mixture of oligomers (pool or library) is obtained from the addition of a mixture of activated monomers during the coupling step or from the coupling of individual monomers with a portion of the support (bead splitting) followed by remixing of the support and subsequent splitting for the next coupling. In this monomeric approach, each monomeric unit would carry a tethered letter, i.e., a functional group for interaction with the target. Further coupling chemistry that allows for the insertion of a tethered letter at a chemically activated intermediate stage is referred to as the sub-monomer approach.

The diversity of the oligomeric pool is represented by the inherent physical properties of each monomer, the number of different monomers mixed at each coupling, the physical properties of the chemical bonds arising from the coupling chemistry (the backbone), the number of couplings (length of oligomer), and the interactions of the backbone and monomer chemistries. Taken together, these interactions provide a unique conformation for each individual molecule.

There remains a need in the art for molecules which have fixed preorganized geometry that matches that of targets such as proteins and enzymes, nucleic acids, lipids and other targets. The backbone of such molecules should be rigid with some flexibility, and such molecules should be easy to construct via automated synthesis on solid support.

SUMMARY OF THE INVENTION

In accordance with this invention there are provided oligomeric compounds and libraries of such compounds comprising a plurality of aminodiol monomer subunits joined by linking groups, wherein each of said aminodiol monomer subunits has one of the structures I, II, III, IV, V, VI, VII, VIII, IX, X, or XI;

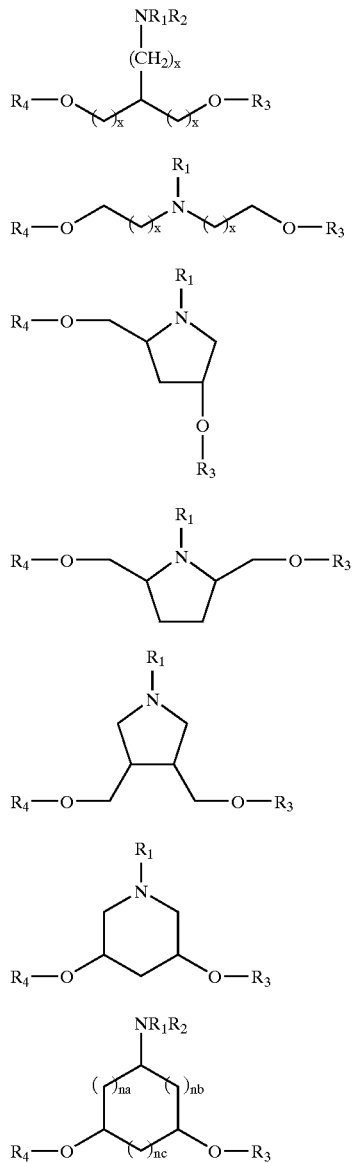

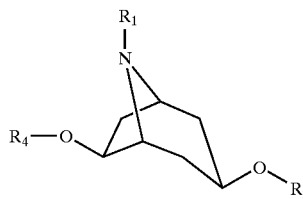

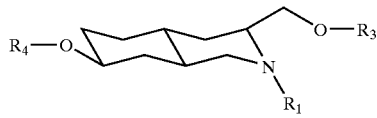

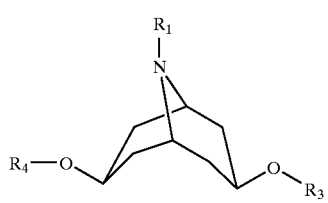

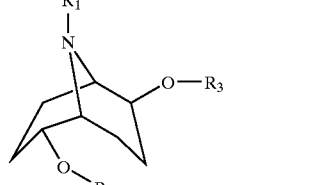

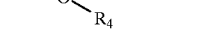

wherein:
each x is, independently, 0 to 5;
na, nb and nc are each, independently, 0 to 2, where the sum of na, nb and nc is from 1 to 5;
$R_1$ is —T—L or a base labile protecting group;
T is a single bond, a methylene group or a group having formula:

$$\{[CR_6R_7]_m-(R_5)-[CR_8R_9]_n-[C(R_{10})]_p-(E)-\}_q-$$

where:
$R_{10}$ is =O, =S, or =$NR_{11}$;
$R_5$ and E, independently, are a single bond, CH=CH, C≡C, O, S, $NR_{11}$, or $C_6$–$C_{14}$ aryl;
each $R_6$, $R_7$, $R_8$, $R_9$, $R_{11}$, $R_{12}$ and $R_{13}$ are, independently, H, alkyl or haloalkyl having 1 to about 10 carbon atoms, alkenyl having 2 to about 10 carbon atoms, alkynyl having 2 to about 10 carbon atoms, or aryl having 7 to about 14 carbon atoms;
m and n, independently, are 0 to 5;
p is 0 or 1;
q is 1 to about 10;
L is H, substituted or unsubstituted $C_2$–$C_{10}$ alkyl, substituted or unsubstituted $C_2$–$C_{10}$ alkenyl, substituted or unsubstituted $C_2$–$C_{10}$ alkynyl, substituted or unsubstituted $C_4$–$C_7$ carbocyclic alkyl, substituted or unsubstituted $C_4$–$C_7$ carbocyclic alkenyl, substituted or unsubstituted $C_4$–$C_7$ carbocyclic alkynyl, substituted or unsubstituted $C_6$–$C_{14}$ aryl, an ether having 2 to 10 carbon atoms and 1 to 4 oxygen or sulfur atoms, a nitrogen containing heterocycle, a sulfur containing heterocycle, an oxygen containing heterocycle, a metal coordination group, a conjugate group, halogen, hydroxyl (OH), thiol (SH), keto (C=O), carboxyl
(COOH), amide ($CONR_{12}$), amidine (C(=NH)
$NR_{12}R_{13}$), guanidine (NHC(=NH)$NR_{12}R_{13}$),
glutamyl ($R_{12}OOCCH(NR_{12}R_{13})(CH_2)_2C$(=O),
nitrate ($ONO_2$), nitro ($NO_2$), nitrile (CN), trifluoromethyl ($CF_3$), trifluoromethoxy ($OCF_3$), O-alkyl, S-alkyl,
NH-alkyl, N-dialkyl, O-aralkyl, S-aralkyl, NH-aralkyl,
amino ($NH_2$), azido ($N_3$), hydrazino ($NHNH_2$),
hydroxylamino ($ONH_2$), sulfoxide (SO), sulfone
($SO_2$), sulfide (S—), disulfide (S—S), silyl, a nucleosidic base, an amino acid side chain, a carbohydrate, a
biopharmaceutically active moiety, or group capable of
hydrogen bonding where the substituent groups are
selected from hydroxyl, amino, alkoxy, alcohol, benzyl,
phenyl, nitro, thiol, thioalkoxy, halogen, alkyl, aryl,
alkenyl, and alkynyl groups;

$R_2$ is hydrogen or $C_1$–$C_{10}$ alkyl;

$R_3$ and $R_4$ are independently hydrogen, an acid labile
hydroxyl protecting group, a linking group or a conjugate group, wherein said linking group has the formula:

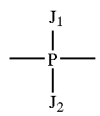

wherein:

$J_1$ is =O or =S;

$J_2$ is OH or $N(Y_0)T_0$;

$Y_0$ is H or $[Q_2]_j$—$Z_2$;

$T_0$ is $[Q_1]_k$—$Z_1$, or together $Y_0$ and $T_0$ are joined in a nitrogen heterocycle;

$Q_1$ and $Q_2$ independently are $C_2$–$C_{10}$ alkyl, $C_2$–$C_{10}$ alkenyl, $C_2$–$C_{10}$ alkynyl, $C_4$–$C_7$ carbocylo alkyl $C_4$–$C_7$ carbocylo alkenyl, a heterocycle, an ether having 2 to 10 carbon atoms and 1 to 4 oxygen or sulfur atoms, a polyalkyl glycol, or $C_7$–$C_{14}$ aralkyl;

j and k independently are 0 or 1;

$Z_1$ and $Z_2$ independently are H, $C_1$–$C_2$ alkyl, $C_2$–$C_{20}$ alkenyl, $C_2$–$C_{20}$ alkynyl, $C_6$–$C_{14}$ aryl, $C_7$–$C_{15}$ aralkyl, halogen, CH=O, $OR_{12}$, $SR_{12}$, $NR_{12}R_{13}$, C(=NH)$NR_{12}R_{13}$, $CH(NR_{12}R_{13})$, NHC(=NH)$NR_{12}R_{13}$, $CH(NH_2)C$(=O)OH, C(=O)$NR_{12}R_{13}$, C(=O)$OR_{12}$, a metal coordination group, a reporter group, a nitrogen-containing heterocycle, a purine, a pyrimidine, a phosphate group, a polyether group, or a polyethylene glycol group; and provided that at least one of said aminodiol monomer subunits in said oligomeric compound does not have structure III.

Further in accordance with this invention there are provided processes for preparing oligomeric compounds and libraries of such compounds comprising:

(a) selecting an aminodiol monomer subunit having the structure I, II, III, IV, V, VI, VII, VIII, IX, X, or XI:

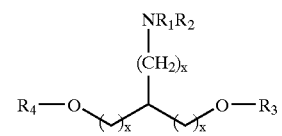

I

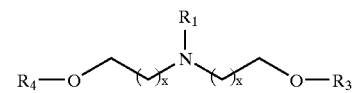

II

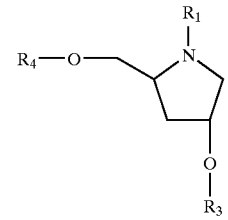

III

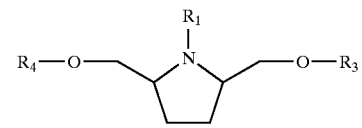

IV

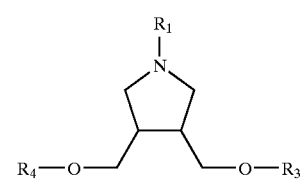

V

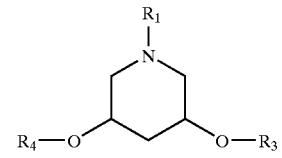

VI

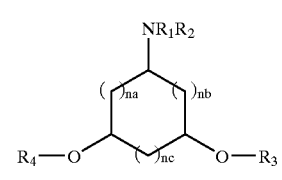

VII

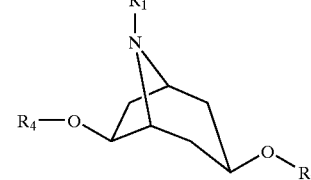

VIII

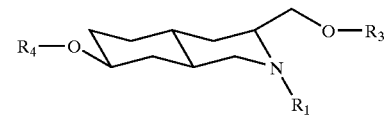

IX

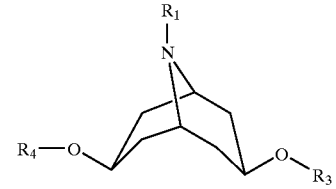

X

-continued

XI wherein:
 each x is, independently, 0 to 5;
 na, nb and nc are each, independently, 0 to 2, where the sum of na, nb and nc is from 1 to 5;
 $R_1$ is a base labile protecting group;
 $R_2$ is hydrogen or $C_1$–$C_{10}$ alkyl; and
 one of $R_3$ or $R_4$ is hydrogen or an activated phosphite group and the other of $R_3$ or $R_4$ is an acid labile hydroxyl protecting group;

(b) attaching said aminodiol monomer subunit to a solid support to form a solid support bound aminodiol monomer subunit;

(c) treating said acid labile hydroxyl protecting group with a dilute acid to form a free hydroxyl group, (d) reacting said free hydroxyl group with a further aminodiol monomer subunit having structure I, II, III, IV, V, VI, VII, VIII, IX, X, or XI, thereby forming an oligomeric compound bound to said solid support, said oligomeric compound containing a phosphite linkage;

(e) optionally iteratively repeating steps (c) and (d) to increase the length of the oligomeric compound bound to said solid support;

(f) optionally, prior to step (c) or after step (d) oxidizing said phosphite linkage to form a phosphate linking group wherein said linking groups are selected having formula:

$$-\overset{\overset{\displaystyle J_1}{|}}{\underset{\underset{\displaystyle J_2}{|}}{P}}-$$

wherein:
 $J_1$ is =O or =S;
 $J_2$ is OH or N ($Y_0$)$T_0$;
 $Y_0$ is H or $[Q_2]_j$—$Z_2$;
 $T_0$ is $[Q_1]_k$—$Z_1$, or together $Y_0$ and $T_0$ are joined in a nitrogen heterocycle;
 $Q_1$ and $Q_2$ independently, are $C_2$–$C_{10}$ alkyl, $C_2$–$C_{10}$ alkenyl, $C_2$–$C_{10}$ alkynyl, $C_4$–$C_7$ carbocylo alkyl or alkenyl, a heterocycle, an ether having 2 to 10 carbon atoms and 1 to 4 oxygen or sulfur atoms, a polyalkyl glycol, or $C_7$–$C_{14}$ aralkyl;
 j and k independently, are 0 or 1;
 $Z_1$ and $Z_2$ independently are H, $C_1$–$C_2$ alkyl, $C_2$–$C_{10}$ alkenyl, $C_2$–$C_{20}$ alkynyl, $C_6$–$C_{14}$ aryl, $C_7$–$C_{15}$ aralkyl, halogen, CH=O, $OR_{12}$, $SR_{12}$, $NR_{12}R_{13}$, C(=NH) $NR_{12}R_{13}$, $CH(NR_{12}R_{13})$, NHC(=NH)$NR_{12}R_{13}$, $CH(NH_2)C(=O)OH$, $C(=O)NR_{12}R_{13}$, $C(=O)OR_{12}$, a metal coordination group, a reporter group, a nitrogen-containing heterocycle, a purine, a pyrimidine, a phosphate group, a polyether group, or a polyethylene glycol group; and (g) prior to step (e) or after step (f) contacting said solid support bound aminodiol monomer subunit or said support bound oligomeric compound with a base to remove said base labile amino protecting group to form the solid support bound aminodiol monomer subunit or support bound oligomeric compound having a free amine, and derivatizing said free amine with a group of the formula -T-L;

wherein:
 T is a single bond, a methylene group or a group having formula:

$\{[CR_6R_7]_m-(R_5)-[CR_8R_9]_n-[C(R_{10})]_p-(E)-\}_q-$ where:
 $R_{10}$ is =O, =S, or =$NR_{11}$;
 $R_5$ and E, independently, are a single bond, CH=CH, C≡C, O, S, $NR_{11}$, or $C_6$–$C_{14}$ aryl;
 each $R_6$, $R_7$, $R_8$, $R_9$, $R_{11}$, $R_{12}$ and $R_{13}$ are, independently, H, alkyl or haloalkyl having 1 to about 10 carbon atoms, alkenyl having 2 to about 10 carbon atoms, alkynyl having 2 to about 10 carbon atoms, or aryl having 7 to about 14 carbon atoms;
 m and n, independently, are 0 to 5;
 p is 0 or 1;
 q is 1 to about 10;
 L is H, substituted or unsubstituted $C_2$–$C_{10}$ alkyl, substituted or unsubstituted $C_2$–$C_{10}$ alkenyl, substituted or unsubstituted $C_2$–$C_{10}$ alkynyl, substituted or unsubstituted $C_4$–$C_7$ carbocyclic alkyl, substituted or unsubstituted $C_4$–$C_7$ carbocyclic alkenyl, or unsubstituted $C_4$–$C_7$ carbocyclic alkynyl, substituted or unsubstituted $C_6$–$C_{14}$ aryl, an ether having 2 to 10 carbon atoms and 1 to 4 oxygen or sulfur atoms, a nitrogen containing heterocycle, a sulfur containing heterocycle, an oxygen containing heterocycle, a metal coordination group, a conjugate group, halogen, hydroxyl (OH), thiol (SH), keto (C=O), carboxyl (COOH), amide (CONR$_{12}$), amidine (C(=NH) NR$_{12}$R$_{13}$), guanidine (NHC(=NH)NR$_{12}$R$_{13}$), glutamyl (R$_{12}$OOCCH(NR$_{12}$R$_{13}$)(CH$_2$)$_2$C(=O), nitrate (ONO$_2$), nitro (NO$_2$), nitrile (CN), trifluoromethyl (CF$_3$), trifluoromethoxy (OCF$_3$), O-alkyl, S-alkyl, NH-alkyl, N-dialkyl, O-aralkyl, S-aralkyl, NH-aralkyl, amino (NH$_2$), azido (N$_3$), hydrazino (NHNH$_2$), hydroxylamino (ONH$_2$), sulfoxide (SO), sulfone (SO$_2$), sulfide (S—), disulfide (S—S), silyl, a nucleosidic base, an amino acid side chain, a carbohydrate, a biopharmaceutically active moiety, or group capable of hydrogen bonding where the substituent groups are selected from hydroxyl, amino, alkoxy, alcohol, benzyl, phenyl, nitro, thiol, thioalkoxy, halogen, alkyl, aryl, alkenyl, and alkynyl groups;

(h) optionally repeating steps (c) and (d) followed by step (g) to increase the length of the oligomeric compound bound to said solid support;

(i) treating said oligomeric compound bound to said solid support with acid to deprotect any protecting groups; and (j) cleaving said oligomeric compound from said solid support.

DESCRIPTION OF PREFERRED EMBODIMENTS

Figure 1A:
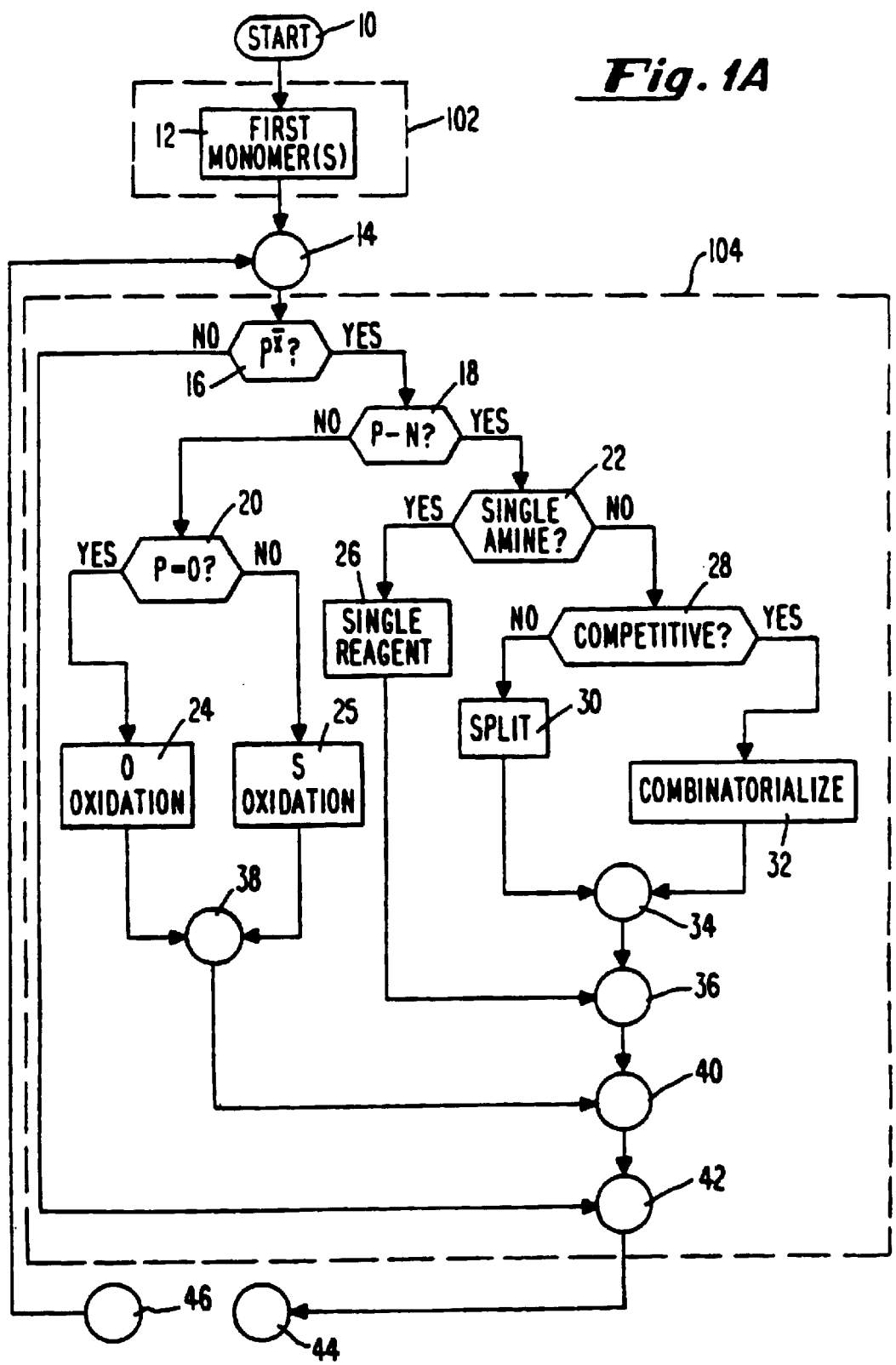
FIG. 1A and FIG. 1B are flow schemes illustrating certain processes of the inventions.

The present invention provides combinatorial libraries of phosphate linked aminodiol monomer subunits having phosphodiester, phosphorothioate, and phosphoramidate linkages. As used in the context of the present invention an aminodiol monomer subunit (monomer subunit or backbone segment) is a cyclic or acyclic compound having a protected reactive amino group either primary or secondary and two hydroxyls that can be either primary or secondary. One of the hydroxyls is protected with an acid labile protecting group and the other is in the form of the free hydroxyl or in the form of an H-phosphonate. The monomer subunits of the invention are coupled using H-phosphonate chemistry to form oligomeric compounds which are substituted with diverse functional groups.

Oligomeric compounds of the invention have reactive sites, also referred to as combinatorial sites, that may be combinatorialized with diverse functional groups. Sites that are available for combinatorializing include reactive amino groups, terminal hydroxyl groups, and H-phosphonate phosphorous groups that can be oxidized with, for example, a) carbon tetrachloride and primary or secondary amines to form a phosphoramidate, b) iodine and water to form phosphodiesters, or c) sulfur in carbon disulfide to form phosphorothioates and terminal hydroxyls. Terminal hydroxyls may also be substituted with a variety of functional groups such as nucleotides or nucleosides to give a chimeric compound or may include any of a variety of other groups such as conjugates, and reporter groups.

Functional groups may be attached directly to combinatorial sites or may include a tethering group to alter their orientation in space. The functional groups are attached to the backbone segment and phosphoramidate moiety with or without intervening tethering groups. Tethering groups, as used in the context of this invention, are bivalent or polyvalent groups that have a primary or secondary amine or other suitable group to react with an H phosphonate backbone segment of the invention together with a second functional group capable of binding a "letter". Such tethers can be used to position "letters" in space with respect to the linear backbone of the oligomeric compound synthesized or to link letters that themselves do not include an amine group—necessary to form a phosphoramidate linkage—as an inherent part of the letter. A particularly preferred group of compounds, when substituted with an appropriate amine functional group where necessary, useful as tethering groups include, but are not limited to $C_2$–$C_{10}$ alkyl, $C_2$–$C_{10}$ alkenyl, $C_1$–$C_{10}$ alkynyl, $C_4$–$C_7$ carbocylo-alkyl or alkenyl, heterocycles, an ether having 2 to 10 carbon atoms and 1 to 4 oxygen or sulfur atoms, polyalkylene glycols and $C_7$–$C_{14}$ aralkyl groups. Other representative tethers useful in the practice of the invention are disclosed in U.S. application Ser. No. 08/116,801, filed Sep. 3, 1993, entitled "Thiol-Derivatized Nucleosides and Oligonucleosides" and U.S. application Ser. No. 117,363, filed Sep. 3, 1993, entitled "Amine-Derivatized Nucleosides and Oligonucleosides", the disclosures of which are hereby incorporated by reference.

The present invention provides for the addition of functional groups onto the backbone of the oligomeric compounds on the solid support. In contrast to previous methods, the synthesis of a large set of monomer subunits bearing various functional groups is not necessary. In one aspect the oligomeric compounds of the invention are composed of three components. The preparation of the combinatorial libraries begins with an aminodiol monomer subunit attached to the solid support directly through a linker stable to the synthesis conditions, but cleavable to release the compound into solution at the end of the synthesis. Preferred linkers include esters, particularly succinic acid.

Alternatively, the monomers can be coupled to a constant moiety attached to the CPG, such as DMT ethylene glycol or a similar diol. Other attachment points to the solid support are possible, for example: nucleosides, amino acids or other groups imparting pharmacokinetic, pharmacodynamic or other desirable properties.

The backbone segments are a structurally diverse set of aminodiols which give different relative orientations of the functional groups. The backbone segment amine function, also referred to as the reactive amino group, or amino combinatorial site, is protected with a base labile protecting group and one hydroxyl is blocked with a protecting group removable with mild acid such as a dimethoxytrityl (DMT) ether. The nitrogen protecting group is first removed from the backbone segment(s) and diverse functional groups added to the reactive amino group. Methods for achieving this are described below. A second monomer subunit can then be added through H-phosphonate coupling after removal of the acid labile protecting group on the terminal end of the compound on the solid support by, for example, treating with dilute acid. The intermediate hydrogen phosphonate diester can be oxidized with, for example, a solution of $CCl_4$ Pyridine (1:1) containing 10% (v/v) of a primary or secondary amine, resulting in the formation of a phosphoramidate linkage. Alternatively the H-phosphonate linkage can be oxidized to the phosphodiester or the phosphorothioate using standard methods and techniques. The second backbone segment can then be substituted with diverse functional groups as above. Any combination of backbone segments and functional groups at the backbone segment amino combinatorial sites can be introduced at any position of the oligomer and a large number of amines can be used at the oxidation step. By repeating these synthetic steps an oligomeric compound is synthesized having any desired sequence of functional groups on the monomer subunits, and amidate derivatives at any linking position. Random positions are introduced into the library by dividing the solid support into portions before the addition of the appropriate reagent. Either the monomers, the monomer substituents or the amines can be randomized. At least one position in the oligomer subsets must be fixed to allow iterative deconvolution. The library subsets are screened in the biological assay of interest. The most active subset defines the most active residue at the fixed position. Further rounds of synthesis and screening are used to determine the sequence of the most active compound in the library.

One feature of the present invention is the use of a nitrogen blocking group to block the reactive amino site. Once the first aminodiol monomer subunit is attached to the solid support, the nitrogen blocking group can be removed under basic (non hydrolytic) conditions. The nitrogen is then derivatized with the diverse functional group of choice. This group can be attached to the amino combinatorial site via a variety of linkage groups: amide, sulfonamide, carbamate, urea, aminoalkane, thiocarbamate, thiourea, etc. This can be accomplished by choosing the appropriate electrophile to derivatize the nitrogen. For example, carboxylic acids can be activated using peptide coupling reagents such as EDC, BOP or HATU. Other reagents which can be used include acid chlorides, -fluorides, -imidazolides, -anhydrides, sulfonyl chlorides, chloroformates, isocyanates, aldehydes (under reductive alkylation conditions), alkyl halides, isothiocyanates, etc. Thus each time a functional group is desired in a library it is introduced via the appropriate coupling conditions using simple starting materials.

The aminodiol monomer subunits in the combinatorial library each bear functional groups e.g. "letters" in addition to those that form linkages. When the aminodiol monomer subunits are linked together, these functional groups provide diverse properties ("diversity") to the resulting oligomeric compounds. The functional groups include hydrogen-bond donors and acceptors, ionic moieties, polar moieties, hydrophobic moieties, aromatic centers, and electron-donors and acceptors. Together, the properties of the individual monomers contribute to the uniqueness of the oligomeric compounds in which they are found. Thus, a library of such oligomers would have a myriad of properties, i.e., "diversity." Collectively, the properties of the individual monomers that together form an oligomeric compound contribute to the uniqueness of such oligomeric compound and impart certain characteristics thereto for interaction with cellular, enzymatic or nucleic acid target sites.

A protecting group such as a member of the trityl family preferably can be used as the acid labile protecting group of one of the two hydroxyls of the aminodiol monomer subunit. The trityl family includes at least trityl, mono-methoxytrityl, dimethoxytrityl and trimethoxytrityl. The dimethoxytrityl group is preferred and can be added by reacting the primary hydroxyl group with 4,4'-dimethoxytrityl chloride. Other hydroxyl protecting groups can be used. Representative hydroxyl protecting groups are described by Beaucage, et al., *Tetrahedron* 1992, 48, 2223. Preferred hydroxyl protecting groups are acid-labile, such as the trityl, monomethoxytrityl, dimethoxytrityl, trimethoxytrityl, 9-phenylxanthine-9-yl (Pixyl) and 9-(p-methoxyphenyl) xanthine-9-yl (MOX).

In other aspects of the present invention the use of acid labile groups which are stable to the trichloroacetic acid treatment used for DMT removal such as BOC-type protecting groups are used. They are stable to extended TCA treatment, but are removed by trifluoroacetic acid solutions (e.g. 5% in $CH_2Cl_2$). Another protecting group class which is compatible to this methodology is the allyl class. These groups are cleaved using transition metal catalysts. These types of protecting group are particularly valuable in cases where the selective deprotection of a particular functional group is desired while the oligomer is still attached to the solid support, allowing a new reactive site to be uncovered. Additional protecting group tactics are possible: e.g. photolabile protecting groups are also compatible with this methodology.

In another aspect of the invention, nitrogen protecting groups that are stable to acid treatment and are selectively removed with base treatment are used to make reactive amino groups selectively available for substitution. Examples of such groups are the FMOC (E. Atherton, R. C. Sheppard in *The Peptides*. S. Udenfriend, J. Meienhofer, Eds. Academic Press, Orlando, 1987, vol 9, p1–38), and various substituted sulfonylethyl carbamates exemplified by the Nsc group (V. V. Samukov, A. N. Sabirov, P. I. Pozdnyakov, *Tetrahedron Lett*, 1994, 35, p7821; C. G. J. Verhart, G. I. Tesser, *Rec. Trav. Chim. Pays-Bas*, 1987, 107, p. 621).

Heterocycles, including nitrogen heterocycles, suitable for use as functional groups include, but are not limited to, imidazole, pyrrole, pyrazole, indole, 1H-indazole, a-carboline, carbazole, phenothiazine, phenoxazine, tetrazole, thiazole, oxazole, oxadiazole, benzoxazole, benzimidazole, triazole, pyrrolidine, piperidine, pyridine, quinoline, piperazine and morpholine groups.

Purines and pyrimidines suitable for use as functional groups include adenine, guanine, cytosine, uridine, and thymine, as well as other synthetic and natural nucleobases (nucleosidic bases) such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, amino, thiol, thioalkyl, hydroxyl and other 8-substituted adenines and guanines, 5-trifluoromethyl and other 5-substituted uracils and cytosines, 7-methylguanine. Further purines and pyrimidines include those disclosed in U.S. Pat. No. 3,687,808, those disclosed in the *Concise Encyclopedia Of Polymer Science And Engineering*, pages 858–859, Kroschwitz, J. I., ed. John Wiley & Sons, 1990, and those disclosed by Englisch et al., *Angewandte Chemie*, International Edition 1991, 30, 613.

Alkyl, alkenyl, and alkynyl groups according to the invention include but are not limited to substituted and unsubstituted straight chain, branch chain, and alicyclic hydrocarbons. Further, in the context of this invention, a straight chain compound means an open chain compound, such as an aliphatic compound, including alkyl, alkenyl, or alkynyl. A branched compound, as used herein, comprises a straight chain compound, such as an alkyl, alkenyl, alkynyl compound, which has further straight or branched chains attached to the carbon atoms of the straight chain. A cyclic compound, as used herein, refers to closed chain compounds, i.e. a ring of carbon atoms, such as an alicyclic or aromatic compound. The straight, branched, or cyclic compounds may be internally interrupted, as in alkoxy or heterocyclic compounds. In the context of this invention, internally interrupted means that the carbon chains may be interrupted with heteroatoms such as O, N, or S. However, if desired, the carbon chain may have no heteroatoms.

Further in the context of this specification aryl groups include but are not limited to substituted and unsubstituted aromatic hydrocarbyl groups. Aralkyl groups include but are not limited to groups having both aryl and alkyl functionalities, such as benzyl and xylyl groups. Preferred aryl and aralkyl groups include, but are not, limited to, phenyl, benzyl, xylyl, naphthyl, tolyl, pyrenyl, anthracyl, azulyl, phenethyl, cinnamyl, benzhydryl, and mesityl. These can be substituted or unsubstituted.

The aliphatic and aromatic groups as noted above may be substituted or unsubstituted. In the context of this invention, substituted or unsubstituted, means that the compounds may have any one of a variety of substituents, in replacement, for example, of one or more hydrogen atoms in the compound, or may have no substituents. Typical substituents for substitution include, but are not limited to, hydroxyl, alkoxy, alcohol, benzyl, phenyl, nitro, thiol, thioalkoxy, halogen, or alkyl, aryl, alkenyl, or alkynyl groups.

Conjugate groups of the invention include intercalators, reporter molecules, polyamines, polyamides, polyethers including polyethylene glycols, and other moieties known in the art for enhancing the pharmacodynamic properties or the pharmacokinetic properties. Typical conjugate groups include PEG groups, cholesterols, phospholipids, biotin, phenanthroline, phenazine, phenanthridine, anthraquinone, acridine, fluoresceins, rhodamines, coumarins, and dyes.

Metal coordination groups according to the invention include but are not limited to hydroxamic acids, catecholamide, acetylacetone, 2,2'-bipyridine, 1,10-phenanthroline, diacetic acid, pyridine-2-carboxamide, isoalkyldiamine, thiocarbamato, oxalate, glycyl, histidyl and terpyridyl. Other metal coordination groups are known, as for example see Mellor, D. P., *Chemistry of Chelation and Chelating Agents in International Encyclopedia of Pharma-*

*cology and Therapeutics*, Section 70, The Chelation of Heavy Metals, Levine, W. G. Ed., Pergamon Press, Elmford, N.Y., 1979.

Solid supports according to the invention include controlled pore glass (CPG), oxalyl-controlled pore glass (see, e.g.,) or Poros—a copolymer of polystyrene/divinylbenzene.

Non-reactive functionalities used as functional groups, such as groups that enhance pharmacodynamic properties, include groups that improve uptake and enhance resistance to enzymatic or chemical degradation. Non-reactive functionalities may also enhance pharmacokinetic properties. In the context of this invention, such groups improve uptake, distribution, metabolism or excretion. Non-reactive functionalities include, but are not limited to, alkyl chains, polyamines, ethylene glycols, steroids, polyamides, aminoalkyl chains, amphipathic moieties, and conjugate groups attached to any of the nitrogenous sites for attachment, as described above.

A number of functional groups can be introduced into compounds of the invention in a blocked form and subsequently deblocked to form a final, desired compound. In general, a blocking group renders a chemical functionality of a molecule inert to specific reaction conditions and can later be removed from such functionality in a molecule without substantially damaging the remainder of the molecule (Green and Wuts, Protective Groups in Organic Synthesis, 2d edition, John Wiley & Sons, New York, 1991). For example, amino groups can be blocked as phthalimido groups, as 9-fluorenylmethoxycarbonyl (FMOC) groups, and with triphenylmethylsulfenyl, t-BOC or CBZ groups. Hydroxyl groups can be protected as acetyl groups. Representative hydroxyl protecting groups are described by Beaucage et al., *Tetrahedron* 1992, 48, 2223. Preferred hydroxyl protecting groups are acid-labile, such as the trityl, monomethoxytrityl, dimethoxytrityl, trimethoxytrityl, 9-phenylxanthine-9-yl (Pixyl) and 9-(p-methoxyphenyl) xanthine-9-yl (MOX). Chemical functional groups can also be "blocked" by including them in a precursor form. Thus, an azido group can be used considered as a "blocked" form of an amine since the azido group is easily converted to the amine.

Additional functional groups according to the invention include but are not limited to H, alkyl or substituted alkyl, alkenyl or substituted alkenyl, alkynyl or substituted alkynyl, carbocyclic alkyl, alkenyl or alkynyl or substituted carbocyclic, or aryl or substituted aryl where the substituent groups are selected from hydroxyl, amino, alkoxy, alcohol, benzyl, phenyl, nitro, thiol, thioalkoxy, halogen, alkyl, aryl, alkenyl, or alkynyl groups; an gluether having 2 to 10 carbon atoms and 1 to 4 oxygen or sulfur atoms; a nitrogen, sulfur or oxygen containing heterocycle; a metal coordination group; a conjugate group; halogen; hydroxyl (OH); thiol (SH); keto (C=O); carboxyl (COOH); amide (CONR$_{12}$), amidine (C(=NH)NR$_{12}$R$_{13}$), guanidine (NHC(=NH) NR$_{12}$R$_{13}$), glutamyl (R$^1$OOCCH(NR$_{12}$R$_{13}$) (CH$_2$)$_2$C(=O), nitrate (ONO$_2$), nitro (NO$_2$), nitrile (CN), trifluoromethyl (CF$_3$), trifluoromethoxy (OCF$_3$), O-alkyl, S-alkyl, NH-alkyl, N-dialkyl, O-aralkyl, S-aralkyl, NH-aralkyl, amino (NH$_2$), azido (N$_3$), hydrazino (NHNH$_2$), hydroxylamino (ONH$_2$), sulfoxide (SO), sulfone (SO$_2$), sulfide (S—), disulfide (S—S), silyl, a nucleosidic base, an amino acid side chain, a carbohydrate, a biopharmaceutically active moiety, or group capable of hydrogen bonding where the substituent groups are selected from hydroxyl, amino, alkoxy, alcohol, benzyl, phenyl, nitro, thiol, thioalkoxy, halogen, alkyl, aryl, alkenyl, and alkynyl groups.

Functional groups of the invention can be represented by structure:

—T—L;

where T is a single bond, a methylene group or a group having formula:

$$\{[CR_6R_7]_m\text{—}(R_5)\text{—}[CR_8R_9]_n\text{—}[C(R_{10})]_p\text{—}(E)\text{—}\}_q\text{—}$$

where:

R$_{10}$ is =O, =S, or =NR$_{11}$;

R$_5$ and E, independently, are a single bond, CH=CH, C≡C, O, S, NR$_{11}$, or C$_6$–C$_{14}$ aryl;

each R$_6$, R$_7$, R$_8$, R$_9$, R$_{11}$, R$_{12}$ and R$_{13}$ are, independently, H, alkyl or haloalkyl having 1 to about 10 carbon atoms, alkenyl having 2 to about 10 carbon atoms, alkynyl having 2 to about 10 carbon atoms, or aryl having 7 to about 14 carbon atoms;

m and n, independently, are 0 to 5;

p is 0 or 1;

q is 1 to about 10;

L is H, substituted or unsubstituted C$_2$–C$_{10}$ alkyl, substituted or unsubstituted C$_2$–C$_{10}$ alkenyl, substituted or unsubstituted C$_2$–C$_{10}$ alkynyl, substituted or unsubstituted C$_4$–C$_7$ carbocyclic alkyl, substituted or unsubstituted C$_4$–C$_7$ carbocyclic alkenyl, substituted or unsubstituted C$_4$–C$_7$ carbocyclic alkynyl, substituted or unsubstituted C$_6$–C$_{14}$ aryl, an ether having 2 to 10 carbon atoms and 1 to 4 oxygen or sulfur atoms, a nitrogen containing heterocycle, a sulfur containing heterocycle, an oxygen containing heterocycle, a metal coordination group, a conjugate group, halogen, hydroxyl (OH), thiol (SH), keto (C=O), carboxyl (COOH), amide (CONR$_{12}$), amidine (C(=NH)NR$_{12}$R$_{13}$), guanidine (NHC(=NH) NR$_{12}$R$_{13}$), glutamyl (R$_{12}$OOCCH (NR$_{12}$R$_{13}$)(CH)$_2$ C(=O), nitrate (ONO$_2$), nitro (NO$_2$), nitrile (CN), trifluoromethyl (CF$_3$), trifluoromethoxy (OCF$_3$), O-alkyl, S-alkyl, NH-alkyl, N-dialkyl, O-aralkyl, S-aralkyl, NH-aralkyl, amino (NH), azido (N$_3$), hydrazino (NHNH$_2$), hydroxylamino (ONH$_2$), sulfoxide (SO), sulfone (SO$_2$), sulfide (S—), disulfide (S—S), silyl, a nucleosidic base, an amino acid side chain, a carbohydrate, a biopharmaceutically active moiety, or group capable of hydrogen bonding where the substituent groups are selected from hydroxyl, amino, alkoxy, alcohol, benzyl, phenyl, nitro, thiol, thioalkoxy, halogen, alkyl, aryl, alkenyl, and alkynyl groups.

As used in this specification, a "functional" group is one that, when attached to a parent molecule, imparts to that molecule a particular and unique characteristic. It contributes diversity to the parent molecule by rendering the parent molecule different in some way from what it was before attachment of the group. Several chemical functional groups can be attached to a particular molecule and when considered together, the sum total of their properties will impart global diversity characteristics to the parent molecule. Each set of combinations of chemical functional groups on a particular molecule will modify the parent such that the parent molecule having each particular combinations of groups will be different from the parent molecule having any of the other combinations of groups. When all of the combinations of the groups on the parent are considered, a library of compounds will be formed that include all of the possible combinations of groups.

Oligomeric compounds of the invention can be synthesized with both the position and the choice of the chemical functional groups predetermined, or allowed to be selected by combinatorial selection. In the context of this invention, "combinatorial" does not mean arbitrary, haphazard or indiscriminate. In the context of this invention, "combinatorial" is construed to mean that within the totality of the population of oligomeric compounds that can be formed using a particular set of functional groups and a particular location of combinatorial sites within the oligomeric compound, there will be sub-populations of each of the possible species. Thus, each of the different combinations of a) choice of functional group and b) positioning of the functional groups will be represented.

"Combinatorial" is distinct from "random." To illustrate the distinction, if all or nearly all possible combinations are present in the total molecular population, then it is a combinatorial population of molecules. If, however, only one or a small number of molecules from that total population is selected, then the selected molecule or molecules might be randomly selected if it is picked at whim or will from the total population. When the totality of the population is considered, all species are present and it is not a random population. If a systematic selection was made until the totality of the population was exhausted, then all of the species would eventually be selected, however, the order of selection might be random. Thus, in certain preferred embodiments, a pre-ordered selection and/or location of chemical functional groups will be present. In further preferred embodiments, a combinatorialized population of all possible combinations and ordering of the chemical functional groups is present. In even further preferred embodiments, the sequence is modulated between fixed and combinatorial. This is especially useful, as for example, in certain deconvolution strategies.

"Deconvolution" is construed to mean taking the totality of a population and systematically working through that population to establish the identity of a particular memeber, selected members, or all members of the population. In deconvoluting a combinatorial library of compounds, systematic selection is practiced until an individual oligomeric compound or a group of individual oligomeric compounds having a particular characteristic, as for instance being an active species in a specific functional assay, is identified.

Conjugate groups can also be used as functional groups in the present invention. Conjugate groups include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, phospholipids, biotin, phenanthroline, phenazine, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA or protein targets. Groups that enhance the pharmacokinetic properties, in the context of this invention, include groups that improve compound uptake, distribution, metabolism or excretion. Representative conjugate groups are disclosed in International Patent Application PCT/US92/09196, filed Oct. 23, 1992, U.S. patent application Ser. No. 116,801, filed Sep. 3, 1993, and U.S. Pat. No. 5,218,105. Each of the foregoing is commonly assigned with this application. The entire disclosure of each is incorporated herein by reference.

Amines include amines of all of the above alkyl, alkenyl and aryl groups including primary and secondary amines and "masked amines" such as phthalimide. Amines of this invention are also meant to include polyalkylamino compounds and aminoalkylamines such as aminopropylamines and further heterocycloalkylamines, such as imidazol-1, 2, or 4-yl-propylamine.

Amino groups amenable to the present invention have the formula $N(Y_0)T_0$, wherein:

$Y_0$ is H, or $[Q_2]_j$—$Z_2$;

$T_0$ is $[Q_1]_k$—$Z_1$, or together $Y_0$ and $T_0$ are joined in a nitrogen heterocycle;

$Q_1$ and $Q_2$ independently, are $C_2$–$C_{10}$ alkyl, $C_2$–$C_{10}$ alkenyl, $C_2$–$C_{10}$ alkynyl, $C_4$–$C_7$ carbocylo alkyl or alkenyl, a hetero-cycle, an ether having 2 to 10 carbon atoms and 1 to 4 oxygen or sulfur atoms, a polyalkyl glycol, or $C_7$–$C_{14}$ aralkyl;

j and k independently, are 0 or 1;

$Z_1$ and $Z_2$ independently are H, $C_1$–$C_2$ alkyl, $C_2$–$C_{10}$ alkenyl, $C_2$–$C_{20}$ alkynyl, $C_6$–$C_{14}$ aryl, $C_7$–$C_{15}$ aralkyl, halogen, CH=O, $OR_{12}$, $SR_{12}$, $NR_{12}R_{13}$, C(=NH)$NR_{12}R_{13}$, CH($NR_{12}R_{13}$), NHC(=NH)$NR_{12}R_{13}$, CH($NH_2$)C(=O)OH, C(=O)$NR_{12}R_{13}$, C(=O)$OR_{12}$, a metal coordination group, a reporter group, a nitrogen-containing heterocycle, a purine, a pyrimidine, a phosphate group, a polyether group, or a polyethylene glycol group.

In some preferred embodiments, the oligomeric compounds of the invention are from 2 to about 30 aminodiol monomers in length. More preferred embodiments have from 2 to about 15 aminodiol monomers, and especially preferred embodiments have from 2 to about 6 aminodiol monomers.

To synthesize a combinatorial library having a large degree of chemical diversity is an important aspect of the present invention. Chemical diversity is introduced at one level by varying the nature of the phosphorus linkage. Phosphorus linkages amenable to the present invention include phosphodiester (OPO), phosphorothioate (OPS), and phosphoramidate (OPN). The desired combinatorial library can be prepared with a single type of phosphorus linkage, or with different linkages at each position of the oligomer. For example, a single OPS linkage can be selectively introduced at any position in a OPO oligomer. In fact, all possible combinations of OPO, OPS, and OPN linkages can be introduced selectively into the oligomeric compounds. The presence or absence of a type of linkage at a particular position in an oligomer will have profound effects on the properties of the molecule.

In the case of phosphoramidate linked libraries, a further level of diversity is possible by oxidizing the H-phosphonate diester linkage with a solution such as $CCl_4$ Pyridine (1:1) containing 10% (v/v) of a primary or secondary amine, resulting in the formation of a phosphoramidate linkage. Any of the H-phosphonate monomer subunits can be introduced at any position of the oligomer and a large number of amines can be used at the oxidation step. Thus it is possible to introduce a wide variety of amines into the oligomeric compound at H-phosphonate linkages by oxidation to the OPN linkage. It is possible to have the same amine substituents at each OPN linkage or a different amine at each position. In the preparation of a combinatorial library from a set of monomer subunits, amines and function groups, all possible combinations are synthesized simultaneously.

Chemical diversity can be generated at several levels in SURF™ libraries. We have described below the preparation of a number of monomer subunits. These monomers have been prepared to explore two aspects of chemical diversity: first a wide number of functional groups are available, covering a range of chemical properties. Second, these functional groups can be attached directly to combinatorial sites or via tethering groups to combinatorial sites. Many different tethering groups are commercially available and are amenable to the present invention. The use of tethering groups alters the presentation of functional groups, in space in different ways, allowing variable flexibility.

Hydrogen phosphonate chemistry allows additional chemical modifications to be introduced into oligomeric compounds. Oligonucleosides phosphodiesters and phosphorothioates have been prepared using this approach,(see Froehler, B. C., Matteucci, M. D. *Tetrahedron Lett.* 1986, 27, 469–472), as well as oligonucleosides phosphoramidates (see Froehler, B. C. *Tetrahedron Lett.* 1986, 27, 5575–5579. Letsinger, R. L., Singman, C. N., Histand, G., Salunkhe, M. *J. Am. Chem. Soc.* 1988, 110, 4470–4471. The synthesis of oligomeric compounds containing both phosphodiesters and phosphoramidates was reported, as well as the use of phosphoramidite chemistry in conjunction with the synthesis of phosphoramidates (see Jung, P. M., Histand, G., Letsinger, R. L. *Nucleosides & Nucleotides*, 1994, 13, 1597–1605). In this latter work, alternating phosphodiester and phosphoramidate oligomeric compounds were prepared by coupling phosphoramidites and H-Phosphonates to the growing oligomer, followed by the appropriate oxidation step. In general, however, all the examples described thus far have incorporated the same amine substitution at all phosphoramidate linkages in the oligomer. These studies have shown the feasibility of using the phosphoramidate bond as an additional site for the incorporation of diverse functional groups.

A wide variety of amines can be used in the oxidative step, and the monomers of the present invention support the necessary chemistry. Thus, for the preparation of combinatorial libraries incorporating phosphoramidate linkages, the monomer subunits of the present invention used as the corresponding H-Phosphonate monoesters. In one aspect of the present invention this is accomplished using $PCl_3$ and imidazole as the phosphitylating reagent (see Garegg, P. J., Regberg, T., Stawinski, J., Strömberg, R. *Chem. Scr.* 1986, 26, 59–62). These H-phosphonates monomer subunits may be oligomerized on solid support by activation with pivaloyl chloride, adamantoyl chloride or other appropriate activating agent. The intermediate H-Phosphonate diesters are oxidized to the phosphate diesters in high yields using iodine in aqueous pyridine. This allowed for the comparison of the coupling efficiency of the H-phosphonate and phosphoramidite methods. Essentially the same coupling efficiency is achieved with both methodologies. The H-phosphonate diesters are converted to phosphoramidates by the use of a 10% solution of the appropriate amine in pyridine/$CCl_4$ (1:1). Under these conditions, a H-phosphonate diester is oxidized to a phosphoryl chloride via an Arbuzov reaction, followed by displacement of the chloride by a primary or secondary amine. The second step has proven to be quite general, with a wide variety of amines giving satisfactory yields. Moreover, the yield of phosphoramidate is comparable to the yield of phosphodiester.

Several types of libraries are available through this methodology. The simplest kind is a library made from a set of monomer subunits of the present invention, and a set of 4 to 16 or more functional groups, of 2 to 10 or more monomer subunits in length, which is substituted at phosphorus with a single amine. These libraries are prepared by split bead synthesis, following the H-phosphonate synthesis protocol rather than phosphoramidite chemistry.

In one aspect of the present invention, intermediate H-phosphonate diesters are left intact until the final step. At that point the oligomer library pools are oxidized with $CCl_4$/Pyridine containing 10% of the appropriate primary or secondary amine. The library therefore is composed of all possible sequences of the monomers, separated into subsets unique at a fixed position, linked together by a constant phosphoramidate linkage. It should be evident that the final properties of the library will be determined by the choice of amine used in the oxidation step. Thus, water solubility, pharmacokinetics and pharmacodynamics of the library components can be modulated by the choice of amine.

It is also possible to prepare oligomer libraries with mixed linkages by having an intermediate oxidation step (see Gryaznov, S. M., Sokolova, N. I. *Tetrahedron Lett.* 1990, 31, 3205–3208; Gryaznov, S. M., Potapov, V. K. *Tetrahedron Lett.* 1991, 32, 3715–3718; Farooqui, F., Sarin, P. S., Sun, D., Letsinger, R. L. *Bioconjugate Chem.*, 1991, 2, 422–426; Iso, Y., Yoneda, F., Ikeda, H., Tanaka, K., Fuji, K. *Tetrahedron Lett.* 1992, 33, 503–506). Thus, a portion of the oligomer library is synthesized by H-phosphonate chemistry, which can be oxidized with ($R_2NH$, $CCl_4$/Py or S8, $CS_2$/TEA or $H_2O$, $CCl_4$/Py), and a second portion of the library synthesized and oxidized with a second set of reagents. This creates a chimeric library, where a segment of the random oligomeric compounds in each subset has a different linkage than the rest of the molecule.

By extension of this methodology, it is possible to incorporate a different linkage at each position of the oligomer library by having a different oxidation step after each monomer subunit coupling. The linkage can be combinatorialized by performing a separate oxidation on a portion of the H-phosphonate diester-linked solid support, followed by pooling of the subsets in the same way that the monomer subunit positions are randomized. Thus, each monomer and the linkage between them can be randomized by a split synthesis strategy.

One advantage of the present invention is that the simple design of monomer subunits of the inventions allows for combining rational drug design with screen mechanisms for thousands of compounds. This is achieved by using the monomer subunits of the invention in a combinatorial techniques such as the SURF™ strategies.

In one preferred embodiment, functional groups appended to oligomeric compounds of the invention are selected for their potential to interact with, and preferably inhibit, the enzyme $PLA_2$. Thus, the oligomeric compounds of the invention can be used for topical and/or systematic treatment of inflammatory diseases including atopic dermatitis and inflammatory bowel disease. In selecting the functional groups, advantage can be taken of $PLA_2$'s preference for anionic vesicles over zwitterionic vesicles. In selecting the backbone segments that bear these functional groups, further advantage can be taken of fact that the natural substrate of $PLA_2$ contains a phosphate group. Therefore, phosphodiester or phosphorothioate and other phosphate linked oligomeric compounds may be selected, providing a negatively charged compound for binding with the positively charged interfacial binding site of $PLA_2$.

Compounds of the invention also include aromatic functional groups to facilitate binding to the cleft of the $PLA_2$ enzyme. (see, Oinuma, et al., *J. Med. Chem.* 1991, 34, 2260; Marki, et al., *Agents Actions* 1993, 38, 202; and Tanaka, et al., *J. Antibiotics* 1992, 45, 1071). Benzyl and 4-hexylbenzyl groups are preferred aromatic groups. The compounds of the invention can further include hydrophobic functional groups such as tetraethylene glycol groups. Since the $PLA_2$ enzyme has a hydrophobic channel, hydrophobicity is believed to be an important property of inhibitors of the enzyme.

In certain embodiments of the invention, aminodiol monomer subunits are incorporated into libraries of oligomeric compounds and increasingly less complex subsets of oligomeric compounds are identified in combinatorial screening techniques such as the above described SURF™ technique by successive rounds of screens. The PLA$_2$ assay can be effected using a combinatorial screening strategy such as the SURF™ strategy. For this assay, the libraries of oligomeric compounds are screened for inhibition of human type II PLA$_2$ enzymatic activity. Typically, these libraries contain about 100 to 100,000 different compounds. Successive iterations of the SURF™ technique is effected to select unique oligomeric compounds from the library. The libraries additionally can be screened in other in vitro assays to determine further mechanisms of inhibition.

Upon identification of oligomeric compounds in a first phase of screening, further modifications can be made to the contents of the libraries of oligomeric compounds. For example, if a first iteration of screening results in an active compound that contains a benzyl group, then in subsequent iterations of the screen this aromatic residue can then be varied using substituted benzyl groups. In this way, structural activity is identified in a stepwise manner to define potent inhibitors of the enzymatic activity.

To maximize the identification of a tight binding oligomeric inhibitor of PLA$_2$ via a combinatorial approach, an array of functional groups typically are included in a randomized library.

Aminodiol monomer subunits can be linked with one another to form homopolymeric structures or they can be linked with nucleotides and/or other moieties to form chimeric structures. For example, chimeric structures can be formed that include one or more regions or "stretches" of the monomer subunits of the invention joined to one or more regions or "stretches" of naturally occurring or synthetic oligonucleotides or to other synthetic or natural oligomeric compounds such as peptides, peptoids, peptide nucleic acids, oligo and/or polysaccharides. Further, oligomeric compounds of the invention can be incorporated into chimeric structures along with the compounds disclosed in the patent application entitled "Monomeric Diols And Phosphate Linked Oligomeric compounds Formed Therefrom," Ser. No. 08/179,970 filed Jan. 11, 1994; which is the parent case for PCT/US95/0049, filed Jan. 11, 1995; and the patent application entitled "Oligonucleosides Mimics Having Nitrogen-Containing Linkages," Ser. No. 08/180,124, filed Jan. 11, 1994; which is the parent case for PCT Application bearing attorney docket ISIS-1852, filed Jan. 11, 1995. The foregoing patent applications are commonly assigned, and are incorporated herein by reference.

In one aspect of the invention, a combinatorial library of oligomeric compounds is synthesized by first attaching a plurality of aminodiol monomer subunits, each having structure I, II, III, IV, V, VI, VII, VIII, IX, X, or XI, below, to a solid support.

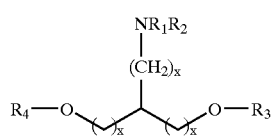

The first aminodiol monomer subunits have base labile protecting groups for $R_1$ and a hydrogen or an alkyl group for $R_2$, if present. One of $R_3$ and $R_4$ is an acid labile protecting group and the other is hydrogen e.g. a free hydroxyl. The free hydroxyl is reacted with a group on the solid support to effect the attachment of the aminodiol monomer subunit to the solid support. Alternatively other bifunctional groups such as ethylene glycol are attached to the solid support with many such compounds known in the art and many commercially available. Solid supports are also available with linking groups previously attached, ready for use without a derivatization step.

The base labile protecting group on the reactive amino group is removed by contacting with a base such as 10% piperidine in DMF or DBU (diazabicycloundecene) in pyridine, and a substituted carboxylic acid or another electrophilic reagent (acid chloride, sulfonyl chloride, etc.) is then covalently linked to the backbone segment amino combinatorial site using standard coupling methods (for examples see Bodansky, M., *Principles of Peptide Synthesis*, 1984, Springer-Verlag, Berlin). Carbamates can be obtained by the treatment of the amine with an appropriate alkyl or aryl chloroformate. Carbamates can be obtained by the treatment of the amine with an appropriate alkyl or aryl chloroformate, in the presence of a catalyst such as pyridine. A urea or thiourea can be formed by reacting the backbone segment amino combinatorial site with an isocyanate or isothiocyanate, or by treatment with carbonyl diimidazole followed by a second amine, in the presence of base. Sulfonamides can be prepared from the amine by the reaction with a sulfonyl chloride in the presence of a base. The nitrogen can be alkylated by treatment with a halide such as the illustrative halides (benzyl bromide, 3-methylbenzyl bromide, 3-methoxybenzyl bromide or 3-nitrobenzyl bromide) used in the examples below. A wide spectrum of halides can be used for this purpose. Additionally, amino compounds can be functionalized by reaction with an aldehyde or ketone forming a Schiff base. The Schiff base is then reduced in the presence of a reducing agent such as $NaCNBH_3$.

Functional groups that require protection are derivatized using acid labile protecting groups which are stable to TCA. The acid labile hydroxyl protecting group is removed by treating with an acid (3% TCA in dichloromethane) and the resulting free hydroxyl is reacted with a second aminodiol monomer subunit H-phosphonate having a base labile protecting group for $R_1$ and a hydrogen or an alkyl group for $R_2$, if present. One of $R_3$ and $R_4$ is an acid labile protecting group and the other is an activated phosphite. The free hydroxyl of the first monomer subunit on the solid support is reacted with the activated phosphite of the second monomer subunit to form a phosphite linkage thereby increasing the length of the growing oligomeric compound by one monomer subunit.

The phosphite linkage is oxidized to a phosphoramidate using a 10% solution of a primary or secondary amine in $CCl_4$/pyridine. The base labile protecting group on the second monomer subunit is then removed with piperidine as above. The resulting amino group is further reacted with an activated functional group. If desired, additional monomer subunits can be added by repeating the synthetic steps described above.

Monomer subunits of the invention can be used to prepare oligomeric compounds having either preselected sequences or sequences determined via combinatorial strategies. One useful combinatorial strategy is the above-noted SURF™ strategy, which is disclosed and claimed in U.S. patent application Ser. No. 749,000, filed Aug. 23, 1991, and PCT Application US92/07121, filed Aug. 21, 1992, both of which are commonly assigned with this application. The entire disclosure of these applications are herein incorporated by reference.

The following is an example of the methods used for the synthesis of a simple combinatorial library. The variable parameters which can be controlled are the following: the backbone segments, the functional groups attached to the backbone segment amino combinatorial site, the amines attached at the phosphoramidate linkage, and the length of the oligomer. In the example described here a very simple library composed of only 32 molecules will be described. This library is prepared by using two different backbone segments, A and B, two carboxylic acids X and Y, and two amines, P and Q. 1) One begins by weighing equal amounts of solid supports derivatized with A and B. The two solid supports are mixed together by suspending the gels in DMF/dichloromethane (1:1) or other solvent, and mixing gently. If more than two backbone segments are used in the library, all the different supports are mixed together at this stage. The mixture of supports is then treated with piperidine in DMF to remove the N-protecting group from both supports. 2) The mixture is separated into a number of equal portions corresponding to the number of reagents to be added in the next step, in this case two. To the first mixture is added activated carboxylic acid X, to the is added activated Y. Once the reaction is complete, the solid supports are mixed as above to give an equimolar mixture of all four possible combinations. The mixture is then treated with trichloroacetic acid to remove the DMT protecting groups on the monomer subunits and provide a free OH group. 3) The mixture is separated into a number of equal portions corresponding to the number of monomer subunits to be added, in this case two. To each mixture a monomer subunit H-phosphonate is then coupled, the solid supports are again mixed, and the support is again divided into equal portions corresponding to the number of amines to be added, in this case two. 4) At this stage all eight possible combinations are present. Each portion is treated separately with a solution an amine, P or Q in $CCl_4$/Pyridine. The portions are then pooled, treated with piperidine in DMF and split. 5) Each mixture of 16 compounds on solid support treated with an activated carboxylic acid, X and Y. The result is two unique pools of 16 compounds each, which can then be deprotected to remove the terminal DMT group and any protecting groups on the functionalities, and cleaved from the solid support. It is also possible to add further combinatorial sites by coupling additional monomer subunits and extending the library molecules. We have used the following nomenclature to describe mixtures of compounds in a concise manner: X represents a fixed position, that is the backbone segment or functional group on the amino combinatorial site at that position is unique and serves to define the pool composition. N represents an equimolar mixture of all possible structures at a particular position. The subscript defines the synthetic step in the library synthesis. In the above example the library made was $X_5N_4N_3N_2N_1$, where $X_5$=X or Y, $N_4$ is an equal mixture of P and Q, $N_3$=A and B, $N_2$=X and Y, and $N_1$=A and B. In this case the fixed position is the last one, but similar methods can be used to fix any position in the library independently. It is also possible to have a single structure or functionality at any position. Once the most active moiety at position 5 is determined for a particular assay e.g. A, then two additional pools are synthesized having this residue in all cases. A second position is fixed and the remainder randomized: for example $A_5X_4N_3N_2N_1$, where $N_{1-3}$ are as above and $X_4$ is either P or Q. A unique structure is determined after 5 rounds of synthesis and screening. The advantage is uncovered when more than two possible components are used in each position: If ten different components are available at each position then 100,000 unique structures exist, yet only 5 rounds of synthesis and screening are necessary.

Illustrative of the SURF™ strategy is a 2'-O-methyl oligonucleosides library (see, Ecker et. al., ibid.) shown in Table I, below. Table I describes the selection of a 2'-O-methyl oligonucleotide for binding to an RNA hairpin. The $K_D$'s, i.e., the binding constants, were determined by gel shift. "X" is used to indicate the position being varied and underlining is used to indicate positions that become fixed during successive iterations of the SURF™ strategy.

TABLE I

|  | $K_D$ (mM) | | | |
| --- | --- | --- | --- | --- |
| Subsets | X = A | X = C | X = G | X = T |
| Round 1 NNNNXNNNN | 22 | <u>10</u> | >100 | >100 |
| Round 2 NNNN<u>C</u>NXNN | >10 | <u>4</u> | >10 | >10 |
| Round 3 NNXN<u>C</u>N<u>C</u>NN | >10 | <u>0.5</u> | >10 | >10 |
| Round 4 NN<u>C</u>XN<u>C</u>NN | >10 | <u>0.15</u> | >10 | >10 |
| Round 5 NN<u>CCC</u>X<u>C</u>NN | <u>0.08</u> | >1 | 0.4 | >1 |
| Round 6 NN<u>CCC</u>ACXN | <u>0.05</u> | >0.5 | 0.08 | >0.5 |
| Round 7 NX<u>CCC</u>ACAN | >0.1 | >0.1 | <u>0.03</u> | >0.1 |
| Round 8 NG<u>CCC</u>ACAX | 0.05 | <u>0.02</u> | 0.05 | 0.04 |
| Round 9 XG<u>CCC</u>ACAC | 0.03 | 0.05 | 0.02 | <u>0.01</u> |

One aspect of the present invention is the inclusion of monomer subunits of the invention in the above-described SURF™ strategy. The SURF™ strategy is equally applicable to libraries of chemical compounds of the present invention in a completely parallel manner. Many other assays are also used as the selection criteria to deduce a winning sequence with the highest activity The functional groups appended to the reactive amino groups of the oligomeric compounds of the invention can be of various structures that impart particular interactive properties to the oligomeric compounds. These chemical functional groups can effect interactions of at least the following types: hydrogen-bond donors and acceptors, ionic, polar, hydrophobic, aromatic, electron donors and acceptors, pi bond stacking or metal binding. As a result of such interactions, the oligomeric compounds of the invention have unique properties effecting the overall global shape, the conformational space, electron density, dipole moment and ability of the compound to interact with enzyme pockets and other binding sites and other similar properties.

To detect an active sequence generated via a combinatorial technique, the concentration of the active molecule is selected to be of sufficiently great that the molecule can be detected within the sensitivity of the chosen assay. As will be recognized, the number of unique structures within a subset produced via a combinatorial technique depends on the length of the oligomer and the number of different functionalities employed. The number of structures is given by the product of the number components at each variable position. This is illustrated in Table II. Table II also indicates the concentration of each sequence when the subset concentration is 100 uM, a typical high-test concentration. We have found that the complexity of the library can be based upon an estimate of the expected $IC_{50}$ (i.e., a concentration at which 50% of enzyme activity is inhibited) that is desirable in a final oligomeric compound. For an expected $IC_{50}$ of 100 nM, the complexities shown in Table II are acceptable, that is, the libraries shown in Table II have complexities that would allow detection of a unique sequence with an $IC_{50}$ of about 100 nM or less.

TABLE II

| Complexity of Libraries | | |
| --- | --- | --- |
| Variable Positions (Mer) | Sequences nM per Subset | Each Sequence At 100 µM Subset |
| 5 Components | | |
| 4-mer | 125 | 800 |
| 5-mer | 625 | 160 |
| 6 Components | | |
| 4-mer | 216 | 463 |
| 5-mer | 1,296 | 77 |
| 7 Components | | |
| 4-mer | 343 | 291 |
| 8 Components | | |
| 4-mer | 512 | 195 |
| 10 Components | | |
| 4-mer | 1,000 | 100 |

The functional groups or components can also be referred to as "letters." The use of such terminology reflects the fact that the different functional groups on the compounds of the invention are positioned in sequences (either predetermined or by random selection) much like letters of the alphabet, hence the term "letter." These letters can be "reactive" or "non-reactive." By "reactive," it is meant that they will interact with a target molecule in some manner (that need not but can be predefined). By non-reactive," it is meant that they are not designed to primarily interact with a target molecule, and in fact while they may interact with the target molecule, the primary purpose of the non-reactive moieties are to impart other properties to the molecule such as, but not necessarily limited to, effecting up-take, distribution, metabolism or identification.

A further advantage of this invention is the ability to synthesize oligomeric compounds that, in addition to or in place of variability in the sequences of the diverse functional groups, have an asymmetric sequence of monomer subunits. Stated otherwise, the monomer subunits can also vary within the oligomeric compounds. This is easily accomplished by using different aminodiol monomer subunits that eventually become the backbone of the oligomeric compounds.

The oligomeric compounds of the invention can be used in diagnostics, therapeutics and as research reagents and kits. They can be used in pharmaceutical compositions by including a suitable pharmaceutically acceptable diluent or carrier. In preferred embodiments, the compounds of the invention act as inhibitors of enzymes such as phospholipase $A_2$; as inhibitors of pathogens such as virus, mycobacterium, bacteria (gram negative and gram positive), protozoa and parasites; as inhibitors of ligand-receptor interactions such as PDGF (platelet derived growth factor), $LTB_4$ (leukotriene $B_4$), IL-6 and complement $C5_A$; as inhibitors of protein/protein interactions including transcription factors such as p50 (NF_B protein) and fos/jun; for the inhibition of cell-based interactions including ICAM induction (using inducers such as IL1-β, TNF and LPS) and as herbicides and insecticides. In other preferred embodiments, the compounds of the invention are used as diagnostic reagents for each of the above noted biological entities, and as reagents in assays and as probes. In other preferred embodiments, the compounds of the invention are used to chelate heavy metals and as imaging agents.

The functional groups can be selected based on chain length, i.e. short versus long, based on the use of a ring versus a linear group, use of an aromatic versus aliphatic group, use of a functionalized group versus a non-functionalized group, to mention only a few of the wide variety of chemical functional groups available. Indeed simply varying functional moieties, e.g. acid, alcohol, aldehyde, amide, amine, amidine, azo, azoxy, double bond, ether, ethylene oxide, guanidine, halide, haloalkyl, hydrazine, hydroxylamine, ketone, mercaptan, nitrate, nitrile, nitro, nitroso, quaternary nitrogen, sulfide, sulfone, sulfoxide, triple bond, urea, etc. on a single backbone segment amino combinatorial site, e.g. a simple alkyl group, yields a vast array of diversity functions. When this is expanded to include placement of such varied functional moieties on a broad platform of backbones, e.g. a series of alkyl compounds, a series of aryl compounds, a series of alicyclic compounds, etc., the potential for a vast array of chemical functional groups is apparent. Other chemical functional groups include alkyl, alkenyl, alkynyl, alicyclic and substituted alkyl, alkenyl, alkynyl, alicyclic; aryl and substituted aryl; aralkyl, substituted aralkyl, heterocycles, nucleobases such as pyrimidines and purines, metal chelating groups and moieties as found in the α-position of amino acids, such as those shown below:

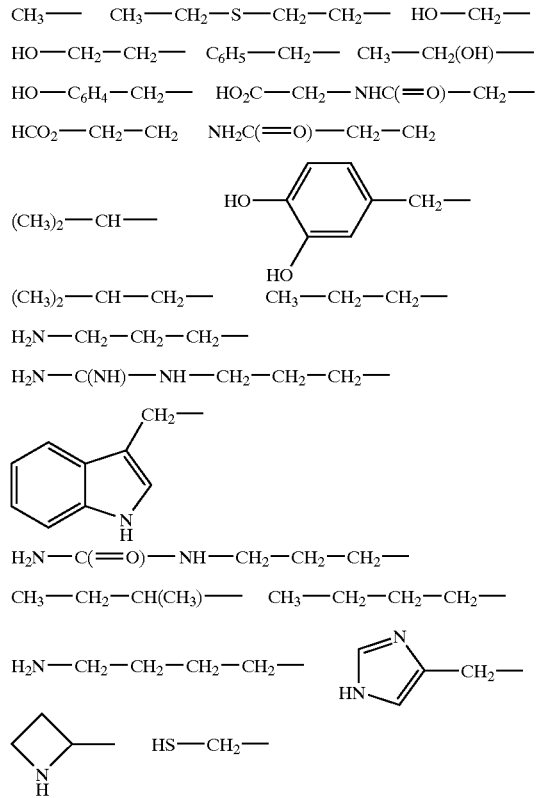

Figure 1B:
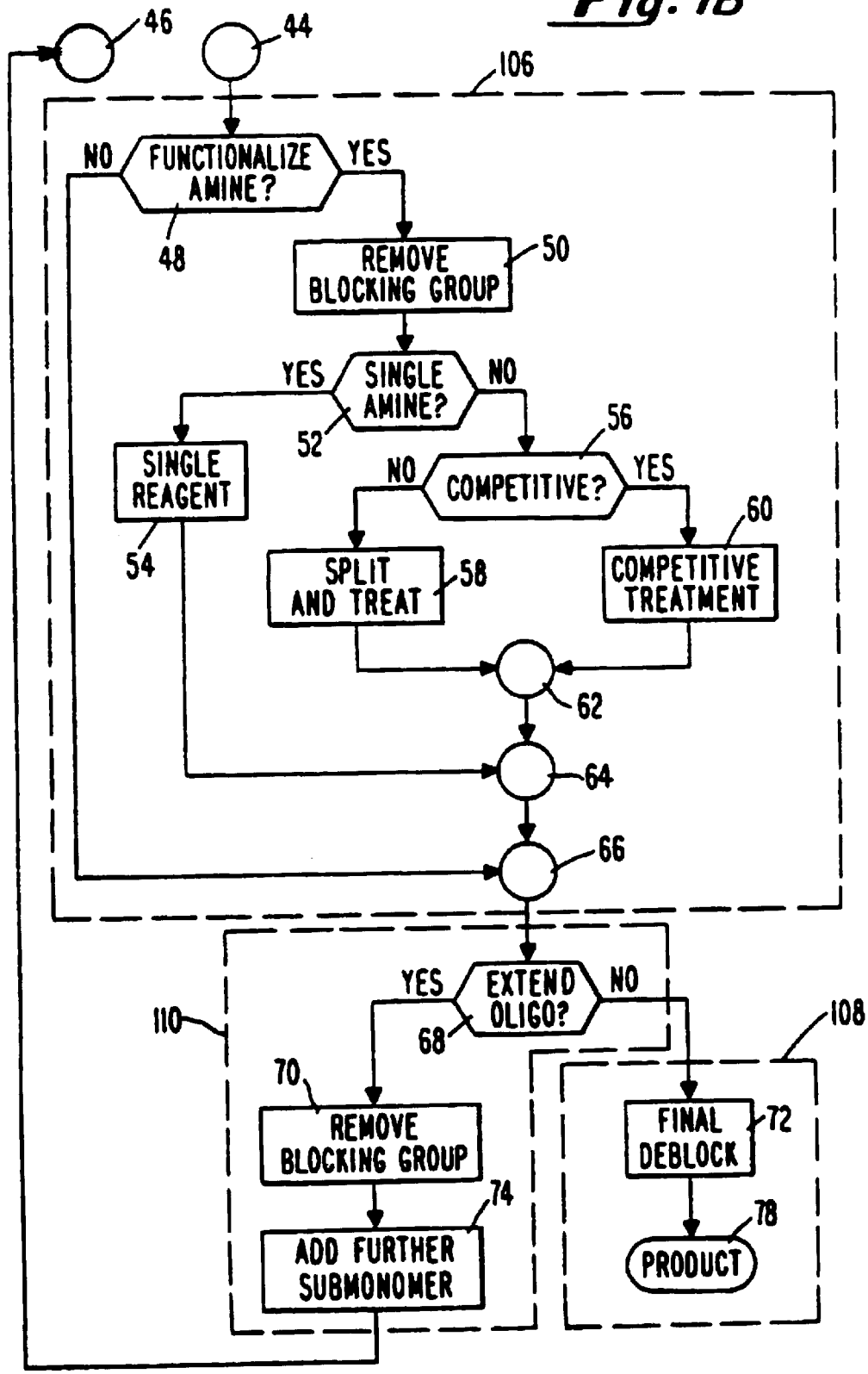

The various combination of reactions that can be effected utilizing the teaching of this invention can be further demonstrate by use of a logical flow scheme. This flow scheme is set forth in FIGS. 1A and 1B.

Referring to the figures, at the start 10 of the synthesis, an aminodiol monomer subunit or group of aminodiol monomer subunits is/are selected. The selected monomer or monomers are processed at process step 12 wherein the aminodiol monomer subunit or subunits is/are attached to a solid support as per Examples 26, 30, 35, 45, 46, 57, 55, and 61, set forth below. The aminodiol monomer subunit may be attached to the solid support via a H-phosphonate diester linkage, through a succinyl linkage, or through an ethyleneglycol linkage. Many other types of linkages are known in the art and are amenable to the present invention. A group of aminodiol monomer subunits may be advantageously attached at this step by utilizing a split bead synthesis. The process steps effected at process step 12 can be otherwise characterized as a selecting and attaching procedure depicted by box 102.

From the procedure box 102, the path of the flow scheme intersects convergent point 14. Convergent point 14 represents the point in the iterative process of the invention wherein growing oligomeric compounds from later steps are reintroduced via this iterative process to undergo further oxidation, amine group functionalization and elongation as discussed below.

Downstream of the convergent point 14, the processes of the invention further include an oxidization step effected via procedures included in the general oxidization procedure depicted by box 104. At decision block 16, within the oxidization procedure generally depicted at box 104, the product of process step 12 (or the growing oligomeric compounds introduced at convergent point 14) is (are) either converted by oxidation from $P^{III}$ to $P^V$ compounds via the positive branch of this step or the $P^{III}$ phosphite linkages are not oxidized and the compounds are maintained with $P^{III}$ linkages and are taken to the next decision step via the negative branch of decision block 16 leading to convergent point 42. For those products of process step 12 (or the growing oligomeric compounds introduced at convergent point 14) wherein oxidization is desired during this iteration of the process (those moving along the positive branch of decision block 16), at decision block 18 they are either converted to phosphoramidates via the positive branch leading from decision block 18 or they are converted into phosphorothioates or phosphodiesters via the negative branch leading from decision block 18.

At decision block 20, growing oligomeric compounds are either oxidized to phosphodiesters at process step 24 via the positive branch of decision block 20 or they are oxidized to phosphorothioates at process step 25 via the negative branch of decision block 20. Oxidation to either the phosphorothioate or phosphodiester, as illustrated in Example 69, can be effected simultaneously on multiple positions on the same growing oligomeric compound, as for instance if the negative branch was taken at decision block 16 for one or more previous iterations of the process. If there are previous unoxidized sites and if the positive branch of decision block 16 is selected during the current iteration, multiple monomeric units are oxidized simultaneously. The resulting phosphodiesters and phosphorothioates converge at convergent point 38 and from there lead to convergent point 40.

Following the positive branch from decision block 18, growing oligomeric compounds at decision block 22 can be converted to phosphoramidates by one of three process steps. First, the decision to effect substitution using a single amine is effected at decision block 22. Growing oligomeric compounds following the positive branch from decision block 22 are converted at process step 26 using a single amine in solution as illustrated in Example 67, to give phosphoramidate linkages having uniform substituents. Growing oligomeric compounds following the negative branch from decision block 22 are combinatorialzed by one of two processes. Growing oligomeric compounds following the negative branch from the competitive combinatorialzation decision block 28 are combinatorialzed at process step 30 by a split bead synthesis. Growing oligomeric compounds following the positive branch of decision block 28 are combinatorialized at process step 32 using a mixture of amines as illustrated in Example 67 Method B.

Growing oligomeric compounds that may have been oxidized (via the positive branch of decision block 16) or may not have been oxidized (via the negative branch of decision block 16) converge at convergent point 42 within the general oxidization procedure box 106. From convergent point 42 the process is continued on FIG. 1B via connector point 44 that connects FIG. 1A and FIG. 1B. A further connector point, point 46, leads back from FIG. 1B to FIG. 1A.

At decision block 48 within the generalized functionalization procedure depicted by box 106, following the positive branch of decision block 48, the growing oligomeric compounds, at process step 50, are deblocked to expose a free amino site on the growing oligomeric compound. This free amino site is now available for functionalization. Alternatively, following the negative branch from decision block 48, amino deblocking and functionalization is bypassed. Following the negative branch of decision block 48, the amine protecting groups are maintained and the growing oligomeric compound is taken directly to convergent point 66.

If in one or more earlier iterations of the process, the negative branch of decision block 48 was selected, there will be multiple amino sites that now are protected and can be deblocked for functionalization. Thus functionalization can be effected at one or at more than one site during any one iteration of the functionalization procedure generally depicted by box 106.

Following the positive branch of the functionalization procedure decision block 48, after deblocking at process step 50, several alternatives are available for functionalization of the resulting free amino site(s). At decision block 52, functionalization with a single functional group or with multiple functional groups is queried. Following the positive branch from decision block 52, functionalization is effected with a single functional group. This functionalization can be performed on a single position or, as noted above, if the functionalization procedure was bypassed in prior iterations of the process, multiple amino positions in a growing oligomeric compound or combinatorial library of such compounds can be functionalized simultaneously. The negative branch of decision block 52 leads to decision block 56 where the deprotected amino site on the growing oligomeric compound can be functionalized with multiple reagents via two different combinatorialization procedures. Following the negative branch from decision block 56, combinatorialization of the free amino site(s) of the growing oligomeric compound(s) is effected at process step 58 using a split bead synthesis. Following the positive branch from decision block 56, combinatorialization of the free amino site(s) is effected at process step 60 by using a mixture of compounds e.g. carboxylic acids or acid halide as, for example, via Examples 63 and 65.

The products of process steps 58 and 60 converge at convergent point 62 and these in turn converge with the products of process step 54 at convergent point 64. Both of these points converge at convergent point 66 where intermediates that were shunted by the deblocking process step 50 via the negative branch of the decision block 48 also converge.

A query is made at decision block 68 to discontinue synthesis or to further elongate the growing oligomeric compound. If the current oligomeric compounds is of sufficient length, at decision block 68, a decision to effect final deblocking, generally depicted by box 108, is made. Following the negative branch of decision block 68, final deblocking is effected at process step 72 to give the final product or products 78.

If further extension of the growing oligomeric compound is desired, the positive branch of decision block 68 is followed. This leads to the extension procedure generally depicted by box 110. To effect oligomeric compound elongation, at process step 70 a hydroxyl protecting group is removed and at process step 74 a further aminodiol monomer subunit is added. The growing oligomeric compound is now re-introduced at conversion point 14 (via connecting point 46) into the process loop for a further iteration of synthesis depicted in FIG. 1A. Here the process of selection of paths independently leading to or bypassing oxidation and/or functionalization is then repeated.

The process of the invention can generally be characterized as first selecting and attaching one or more monomer subunits to a support. This corresponds generally to procedure box 102 of the figures. For the moment bypassing the oxidization procedure, generally depicted by box 104, and the functionalization procedure, generally depicted by box 106, the hydroxyl blocking group of the monomeric subunits can be removed and a further iteration of the addition of monomer units effected. This is accomplished by the extension procedure generally depicted by box 110.

If during this iteration of the process, oxidization of the phosphate linker is desired, oxidization will be effected via the oxidization procedure generally depicted by box 104. Further if prior to the next iteration but post the oxidization procedure, functionalization of the amino group of the last monomer subunit(s) added is desired, functionalization is effected via the functionalization procedure generally depicted by box 106.

If the growing oligomeric compound or compounds is/are of sufficient length, synthesis is halted and the compound or compounds are deblocked and cleaved from their supports via the final deblocking procedure, generally depicted by box 108.

It is of course recognized that the oxidization step of the first monomer subunit can be effected or oxidization of each subsequently added monomer subunit can be effected during the iteration of the process when they are added. Alternatively, oxidization need not be effected for each monomeric subunit added but can be effected during some subsequent iteration of the process. It is further recognized that functionalization of the amino site can be effected for the first monomer subunit and it can be effected for each added monomer subunit. Alternatively, functionalization need not be effected for each monomeric subunit added but can be effected during some subsequent iteration of the process.

EXAMPLE 1

N-Fmoc-trans-4-Hydroxy-L-Proline trans-4-Hydroxy-L-proline (5.00 g, 38.2 mmol) and NaHCO$_3$ (8.00 g, 95.2 mmol) were suspended in 150 ml H$_2$O/Dioxane (1:1). Fluorenylmethyl chloroformate (11.4 g, 44.0 mmol) in 25 ml toluene was added dropwise. The temperature of the reaction was not allowed to rise above 25° C. during the addition. The mixture was stirred vigorously overnight, and then quenched with 50 ml saturated NaHCO$_3$ solution and 50 ml water. The solution was then extracted with 100 ml diethyl ether. The aqueous layer was acidified to pH 1 with concentrated HCl, and extracted twice with ethyl acetate, and the organic extracts washed with brine. The solution was dried with MgSO$_4$, filtered and the solvent removed in vacuo. The pure product crystallized from the concentrated solution. Yield: 13.4 g (100%). $^1$H NMR: (CDCl$_3$, 200 MHz) δ 7.75–7.15 (8H, m, ArH), 4.55–4.05 (5H, m, ArCHCH$_2$, H2, H4), 3.65–3.45 (2H, m, 2 H5), 2.35–2.10 (2H, m, 2 H3).

EXAMPLE 2

N-Fmoc-3-Hydroxypyrrolidine-5-Methanol

To a solution of N-Fmoc-trans-4-hydroxy-L-proline (13.4 g, 38.1 mmol) in 250 ml THF was added borane-methyl sulfide (78 mmol, 5.78 g, 7.22 ml) dropwise at room temperature. After the evolution of H$_2$ had ceased, the solution was heated to reflux with mechanical stirring. After 1 hour a white precipitate had formed. Methanol was carefully added, and the resulting solution refluxed for a further 15 minutes. The solution was cooled to room temperature, the solvents evaporated under reduced pressure, and the residual gum coevaporated with 2×100 ml methanol. The resulting crystalline product weighed 12.0 g (35.3 mmol, 93%). $^1$H NMR: (CDCl3, 200 MHz) δ 7.85–7.25 (8H, m, ArH), 4.50–4.10 (5H, m, ArCHCH2, H3, H5), 3.80–3.40 (4H, m, 2 H2, 2 H6), 2.15–1.95 (1H, m, H2a), 1.80–1.60 (1H, m, H2b).

EXAMPLE 3

N-Fmoc-5-Dimethoxytrityloxymethyl-3-Hydroxypyrrolidine

The diol, N-Fmoc-3-hydroxypyrrolidine-5-methanol (10.59 g, 31.2 mmol) was coevaporated with dry pyridine (2×50 ml), redissolved in 200 ml dry pyridine, and cooled in an ice bath. Dimethoxytrityl chloride (11.0 g, 32.5 mmol) was added in portions over 30 min, and the solution stirred at 0° C. overnight. Methanol was then added (10 ml), and the solvent removed under reduced pressure. The resulting gum was redissolved in toluene (100 ml), filtered to remove the pyridinium hydrochloride and taken to dryness again. The residue was dissolved in CH$_2$Cl$_2$ (300 ml), washed with 150 ml 0.1 M citric acid solution, 150 ml sat NaHCO$_3$, brine, and dried with Mgso$_4$ followed by evaporation. The residue was crystallized from methanol and dried to give (15.4 g, 23.9 mmol, 77%).

EXAMPLE 4

5-Dimethoxytrityloxymethyl-3-Hydroxypyrrolidine

To a solution N-Fmoc-5-dimethoxytrityloxymethyl-3-hydroxypyrrolidine (3.40 g, 5.30 mmol) in 15 ml DMF was added piperidine (1.09 ml, 0.935 g, 11.0 mmol). The solution was stirred at room temperature for 1 hour, water (100 ml) added, and the aqueous solution extracted with ethyl acetate (2×75 ml). The organic extracts were washed with aqueous NaHCO$_3$, brine, dried with MgSO$_4$ and evaporated. The residue was purified by flash column chromatography using a gradient of 1–3% MeOH in CH$_2$Cl$_2$ containing 0.5% triethylamine. Pure product was obtained (1.86 g, 84%). $^1$HNMR: (CDCl$_3$, 200 MHz) δ 7.42–6.80 (13H, ArH), 4,35 (1H, m, H5), 3.77 (6H, s, 2 OCH$_3$), 3.62 (1H, m, H3), 3.13–2.88 (4H, m, 2 H6, 2 H2), 1.87 (1H, q, H4a), 1.65 (1H, m, H4b).

EXAMPLE 5

N-(Phenylacetyl)-5-Dimethoxytrityloxymethyl-3-Hydroxy-pyrrolidine

Phenylacetic acid (1.50 g, 11 mmol) and HOBT (1.63 g, 12 mmol) were dissolved in 100 ml CH$_2$Cl$_2$ and EDC (15 mmol, 2.88 g) was added. After 15 min, 5-dimethoxytrityloxymethyl-3-hydroxypyrrolidine was added, followed by DIEA (20 mmol, 3.5 ml). The reaction was stirred until the starting material was consumed, and quenched with 10 ml NaHCO$_3$. The mixture was extracted twice with ethyl acetate, washed with NaHCO$_3$, brine, dried with MgSO$_4$, and evaporated. The product was purified by flash chromatography to give 4.0 g product (75%). $^1$H NMR: (CDCl$_3$, 200 MHz) (2 rotamers, 3'-O-TMS) d 7.43–7.13, 6.88–6.74 (13 Ar—H), 4.67, 4.49, 4.37, 4.13 (4 m, 2H, H3, H5), 3.78 (s, 6H, OCH$_3$), 3.78–3.50 (m, 2H, H2a, b), 3.66, (s, 2H, CH$_2$Ar) 3.35 (q, 1H, H6a), 3.12 (m, 1H, H6b), 2.14–1.70 (m, 2H, H4a, b), 0.10 (d, 9H, OSi(CH$_3$)$_3$).

EXAMPLE 6

Succinic Acid Fluorenylmethyl Ester

Fluorenemethanol (10.0 g, 51.0 mmol) was dissolved in 150 ml CH$_2$Cl$_2$, and succinic anhydride (5.6 g, 56 mmol) was added. The solution was stirred for 6 h, and a further portion of succinic anhydride (2.5 g, 25 mmol) was added, and stirring continued overnight. The reaction appeared complete by TLC. The solvent was then removed, and the residue extracted with ethyl acetate, washed with 1% HCl, water, brine, dried (MgSO$_4$) and evaporated to an oil which crystallized on standing. A quantitative yield of crude product was obtained which was used without further purification.

EXAMPLE 7

(N1-Thymine)-2-Acetic Acid

Methyl bromoacetate (25.5 g, 15.2 ml, 160 mmol) was added to a suspension of K$_2$CO$_3$ (44.2 g, 320 mmol) and thymine (20.2 g, 160 mmol) in 500 ml dry DMF with stirring overnight. The suspension was filtered and the solvent removed under reduced pressure. The residue was suspended in 120 ml H$_2$O and 30 ml 4 N HCl, stirred for 30 minutes and filtered again. The solid was suspended in 250 ml H$_2$O, to which was added 100 ml 2.5 M NaOH. The solution was heated to boiling, cooled and acidified to pH 1 with concentrated HCl. The precipitate was dried in vacuo to give 13.6 g (73.6 mmol, 46%) pure product. $^1$H NMR: (DMSO-d6, 200 MHz) δ 7.48 (s, 1H, H6), 4.37 (s, 2H, CH$_2$), 1.76 (s, 3H, CH$_3$).

EXAMPLE 8

N-Fmoc-3-Aminopropionic Acid

Sodium bicarbonate (2.52 g, 30 mmol) and 3-aminopropionic acid (1.00 g, 11.2 mmol) were dissolved in 50 ml water and 50 ml dioxane was added. A solution of fluorenylmethyl chloroformate (3.10 g, 12.0 mmol) in 50 ml dioxane was added dropwise with stirring. After 6 hours the solution was diluted with water (100 ml) and saturated bicarbonate solution (50 ml), extracted once with diethyl ether, and the aqueous layer acidified to pH 2 with concentrated HCl. The cloudy solution was extracted with ethyl acetate (2×100 ml), washed with brine and dried with $MgSO_4$. After evaporation a mixture of the title product and the peptide dimer was obtained. The pure product was obtained by flash chromatography. $^1$H NMR: ($CDCl_3$, 200 MHz) δ 7.95–7.26 (8H, m, ArH), 7.40–7.15 (3H, m, $CHCH_2O$), 3.20 (2H, t, J=8 Hz, $CH_2N$), 2.40 (2H, t, J=8 Hz, $HOOCCH_2$).

EXAMPLE 9

N-Imidazolyl-2-Acetic Acid

Imidazole (3.7 g, 54 mmol) was added to a suspension of sodium hydride (2.6 g of a 60% dispersion in oil, 60 mmol) in 50 ml dry THF. Bromoacetic acid (3.4 g, 24 mmol) was then added and the mixture stirred overnight. Water (1 ml) was then added and the solvent removed under reduced pressure. The residue was taken up in water (50 ml, pH >10), extracted with ether and the organic layer discarded. The aqueous layer was acidified to pH 1 with concentrated HCl and extracted again with ether. The aqueous layer was evaporated to dryness. The oily residue was dissolved in absolute ethanol (EtOH) to precipitate NaCl, and recrystallized from acetone/methanol to give 1.22 g (7.5 mmol, 30%) pure product as the hydrochloride. $^1$H NMR: (DMSO-d6, 200 MHz) δ 9.20 (s, H2), 7.76 (d, J=1.5 Hz), 7.69 (d, J=1.5 Hz), 5.20 (s, $CH_2$).

EXAMPLE 10

(9-Adenine)-2-Acetic Acid Ethyl Ester

Sodium hydride (8.20 g 60% in oil, 205 mmol) was added to a suspension of adenine (25.0 g, 185 mmol) in 500 ml DMF. After vigorous stirring for 2 hours using a mechanical stirrer, $H_2$ evolution stopped and a thick slurry was obtained. Ethyl bromoacetate (55.6 g, 36.9 ml, 333 mmol) was added dropwise over 3 hours, and stirring continued for a further 1 hour. Water (10 ml) and $H_2SO_4$ were added to pH 4. The solvent was evaporated and the residue suspended in 500 ml $H_2O$, filtered and washed with water. The residue was recrystallized from 400 ml ethanol to give 23.8 g (108 mmol, 58%) pure product.

EXAMPLE 11

(N6-Benzoyl-9-Adenine)-2-Acetic Acid

To a suspension of (9-adenylyl)-2-acetic acid ethyl ester (6.06 g, 27.4 mmol) in 250 ml dry pyridine was added benzoyl chloride (9.60 ml, 11.6 g, 82 mmol), and the solution stirred for 4 hours at room temperature. Methanol (25 ml) was added and the solvents evaporated. The residue was dissolved in ethyl acetate (2×250 ml), washed with 0.1 N HCl, $H_2O$, saturated $NaHCO_3$, brine, and dried with $Na_2SO_4$. The organic extracts were evaporated and the solid residue was redissolved in 250 ml THF at 0° C., to which was added 100 ml 1M NaOH. The solution was stirred at 0° C. for 1 hour and acidified to pH 1 with concentrated HCl, and the aqueous portion extracted once with ether. The product, which began to crystallize almost immediately, was collected by filtration to yield 4.96 g (61%). $^1$H NMR: (DMSO-d6, 200 MHz) δ 8.86, 8.84 (d, H2, H8), 8.1 (d, 2H, J=7.0 Hz, ArH), 7.69–7.58 (m, 3H, Ar—H), 5.22 (s, 2H, $CH_2$).

EXAMPLE 12

N-4-Benzoylcytosine

Cytosine hemihydrate (12.0 g, 100 mmol) was coevaporated with pyridine and resuspended in 250 ml dry pyridine. Benzoyl chloride (58 ml, 70.3 g, 500 mmol) was added dropwise (exothermic). The solution was stirred at RT overnight, and water (50 ml) carefully added. The solvent was evaporated, and the residue dissolved in 700 ml $H_2O$ containing 55 g NaOH. The solution was stirred for 1 h after complete dissolution of the material. Concentrated HCl was then added to pH 4.0, the white precipitate was collected and boiled in 1 liter EtOH, cooled to RT and filtered to give 16.1 g product (75%).

EXAMPLE 13

N-4-Benzoyl-1-Cytosine-2-Acetic acid

To a suspension of N-4-Benzoylcytosine (15.0 g, 69.7 mmol) and $K_2CO_3$ (9.7 g, 70 mmol) in 500 ml DMF was added methyl bromoacetate (6.6 ml, 10.7 g, 70 mmol). The suspension was stirred vigorously for 3 days, filtered and evaporated. The residue was treated with water (120 ml), and 10 ml 4N HCl for 15 min, and the solid collected by filtration. The residue was resuspended in 120 ml water, and 60 ml 2N NaOH added. The suspension was stirred at RT for 45 min, until all the solids had dissolved. The solution was acidified to pH 2 with conc HCl, filtered, and the solid dried in vacuo at 60° C. to give 11.6 g product (61%).

EXAMPLE 14

N-2-Isobutyroyl-9-Guanine-2-Acetic Acid

To a suspension of 2-amino-6-chloropurine (10 mmol) and $K_2CO_3$ (15 mmol) in DMF (25 ml) is added ethyl bromoacetate (10 mmol). The mixture is stirred vigorously for 24 hours, filtered and the solvent evaporated. The residue is resuspended in 25 ml pyridine and isobutyroyl chloride added (20 mmol). After stirring for 18 hours, water is added and the solvent removed. The residue is suspended in 1N HCl and heated to reflux for 1 hour. The suspension is then cooled to 0° C., NaOH added to pH 12, and the suspension stirred for 1 hour. The solution is acidified to pH 3, and the product is collected by filtration.

EXAMPLE 15

Benzyl 3,6,9,12-Tetraoxatridecanoate

Triethyleneglycol monomethyl ether (10 mmol) and benzyl bromoacetate (11 mmol) are added to a suspension of anhydrous $K_2CO_3$ (15 mmol) in 50 ml anhydrous DMF. The suspension is stirred at room temperature overnight. Water is added and the emulsion is extracted with ethyl acetate (3×200 ml), washed with water, brine, and dried with $MgSO_4$. The solvent is evaporated and the residual oil purified by flash chromatography to give the title compound.

EXAMPLE 16

3,6,9,12-Tetraoxatridecanoic Acid

Benzyl-3,6,9,12-Tetraoxatridecanoate (5 mmol) is dissolved in methanol (50 ml) and 10% palladium on carbon is added (100 mg catalyst/mmol). The suspension is shaken under 30 psi $H_2$ until the starting material is consumed. The suspension is filtered through a short pad of Celite, washed thoroughly with methanol, and the solvent evaporated. The product is used directly without purification.

EXAMPLE 17

Benzyl Bis-[(2-Pyridyl)-2-ethyl]-Aminoacetate

To a suspension of $K_2CO_3$ (15 mmol) in 25 ml DMF was added 2,2'-bis(2-pyridylethyl)-amine (10 mmol) followed by benzyl bromoacetate (12 mmol). The suspension was stirred for 4 hours at room temperature. Water was then added, and the suspension extracted with ethyl acetate (2×100 ml), washed with 5% $Na_2CO_3$, water, brine, dried with $MgSO_4$ and the solvents removed. The product was obtained as an oil in quantitative yield. Product was identified by NMR.

EXAMPLE 18

Bis(2-(2-Pyridyl)ethyl)-Aminoacetic Acid

Benzyl bis-[(2-pyridyl)-2-ethyl]-aminoacetate (5 mmol) is dissolved in methanol (50 ml) and 10% palladium on carbon is added (100 mg catalyst/mmol). The suspension is shaken under 30 psi $H_2$ until the starting material is consumed. The suspension is filtered through a short pad of Celite, washed thoroughly with methanol, and the solvent evaporated. The product is used directly without purification.

EXAMPLE 19

N-Carbazolyl-2-Acetic acid

The title compound is prepared as per Example 13 using carbazole as the starting heterocycle.

EXAMPLE 20

N-Pyrrolyl-2-Acetic acid

The title compound is prepared as per Example 13 using pyrrole as the starting heterocycle.

EXAMPLE 21

N-Trifluoroacetyl-Glycine Triethylammonium salt

To a suspension of glycine (1.50 g, 20 mmol) in 100 ml dry methanol were added triethylamine (3.5 ml, 2.5 g, 25 mmol) and ethyl trifluoroacetate (3.0 ml, 3.55 g, 25 mmol). The mixture was stirred overnight to give a homogeneous solution. The solvents were removed and the resulting oil coevaporated with toluene to remove traces of methanol. The product was used without purification.

EXAMPLE 22

2-O-(Dimethoxytrityl)ethanol

A solution of ethylene glycol (2.45 ml, 44 mmol) in dry pyridine (25 ml) was cooled to 0° C. in an ice bath. Excess triethylamine (7 ml) and 4-dimethylaminopyridine catalyst (120 mg, 1 mmol) was added followed by the slow addition of dimethoxytrityl chloride (7.42 g, 21.9 mmol) over 30 minutes. The mixture was stirred at 0° C. for 1 hr and then room temperature for 1 hr. The resulting solution was quenched with methanol and evaporated to dryness under reduced pressure. The residue was dissolved in saturated $NaHCO_3$ and extracted with EtOAc. The EtOAc extracts were washed with cold saturated sodium bicarbonate and brine. The organic phase was separated, dried over sodium sulfate, filtered and evaporated under reduced pressure. The resulting residue was purified by flash column chromatography on silica gel using ethyl acetate-hexanes (gradient 10 to 20%). The title compound was isolated to yield 5.53 g (70%). $^1$H NMR: ($CDCl_3$) δ 7.50–7.20, 6.90–6.80 (m, 13 H, ArH), 3.80 (s, 6 H, $OCH_3$), 3.75 (t, 2H, $CH_2OH$), 3.25 (t, 2H, $DMTOCH_2$).

EXAMPLE 23

2-Dimethoxytrityl ethanol hemisuccinate Triethylammonium salt

A solution of 2-O-(dimethoxytrityl)ethanol (1.0 g, 2.77 mmol), triethylamine (0.4 ml, 3 mmol), and 4-dimethylaminopyridine catalyst (120 mg, 1 mmol) in dry dichloroethane was treated with succinic anhydride (410 mg, 0.41 mmol). The mixture was stirred at room temperature for 16 hrs. The mixture was filtered and the filtrate was purified by silica gel flash column chromatography using chloroform-methanol-triethylamine to yield the title compound as a triethylammonium salt. $^1$H NMR: ($CDCl_3$) δ 7.50–7.20, 6.90–6.80 (m, 13H, ArH), 4.26 (t, 2H, $CH_2OCO$), 3.80 (s, 6H, $OCH_3$), 3.25 (t, 2H, $DMTOCH_2$), 3.05 (q, 6H, $N(CH_2CH_3)_3$), 2.70 (m, 4H, $OOCCH_2CH_2COO$), 1.25 (t, 9H, $N(CH_2CH_3)_3$.

EXAMPLE 24

2-O-(Dimethoxytrityl)ethoxyphosphonic Acid

A solution of imidazole (4.29 g, 63 mmol)in dry acetonitrile at 0° C. (100 ml) was treated dropwise with $PCl_3$ (1.77 ml, 20.3 mmol) over a period of 30 minutes. The resulting solution was further treated with triethylamine (9.06 ml, 65 mmol). To the thick slurry was added 2-O-(dimethoxytrityl)ethanol (2.10 g, 5.81 mmol) in anhydrous acetonitrile (150 ml) slowly over a period of 30 minutes. The mixture was allowed to warm to room temperature and stirred for 15 minutes. The mixture was quenched with 1M TEAB and the mixture is evaporated in vacuo to a minimum volume and extracted with dichloromethane (2×150 ml). The dichloromethane extracts were washed with TEAB and evaporated in vacuo. The residue was purified by flash column chromatography using a gradient of 0% to 5% methanol in dichloromethane/1% triethylamine to yield 1.3 g purified material (43%). $^1$H NMR: ($CDCl_3$) δ 7.50–7.20, 6.90–6.80 (m, 13 H, ArH), 6.96 (d, 1H, $J_{PH}$=624 Hz, PH), 4.06 (m, 2H, $CH_2OP$), 3.80 (s, 6H, $OCH_3$), 3.25 (t, 2H, $DMTOCH_2$), 3.05 (q, 6H, $N(CH_2CH_3)_3$), 1.25 (t, 9H, $N(CH_2CH3)_3$). $^{31}$P NMR ($CDCl_3$); 5.89.

EXAMPLE 25

Synthesis of 2-O-(Dimethoxytrityl)-ethylsuccinate Half Ester

A solution of 2-O-(dimethoxytrityl)ethanol (1.0 g, 2.77 mmol), triethylamine (0.4 ml, 3 mmol), and 4-dimethylaminopyridine catalyst (120 mg, 1 mmol) in dry dichloroethane was treated with succinic anhydride (410 mg, 0.41 mmol). The mixture was stirred at room temperature for 16 hrs. The mixture was filtered and the filtrate was purified by silica gel flash column chromatography using chloroform-methanol-triethylamine to yield the title compound as a triethylammonium salt. $^1$H NMR: (CDCl$_3$) δ 7.50–7.20, 6.90–6.80 (m, 13H, ArH), 4.26 (t, 2H, CH$_2$OCO), 3.80 (s, 6H, OCH$_3$), 3.25 (t, 2H, DMTOCH$_2$), 3.05 (q, 6H, N(CH$_2$CH$_3$)$_3$), 2.70 (m, 4H, OOCCH$_2$CH$_2$COO), 1.25 (t, 9H, N(CH$_2$CH$_3$)$_3$.

EXAMPLE 26

Derivatization of LCAA CPG with 2-O-(Dimethoxytrityl)-ethylsuccinate Half Ester

2-O-(Dimethoxytrityl)ethylsuccinate half ester triethylammonium salt (135 mg) was dissolved in dichloromethane (5 ml). 4-Dimethylaminopyridine catalyst (40 mg, 0.2 mmol) was added followed by toluene diisocyanate (0.029 ml, 0.2 mmol). The mixture was shaken for 18 min. Long chain alkyl amine controlled pore glass (LCAA CPG) (1.0 g) was added and the mixture was shaken with the exclusion of light for 16 hrs. The mixture was filtered and washed with dichloromethane and then diethylether (3×10 ml each). The CPG was shaken for 16 hrs in pyridine/water (4:1), filtered, and rinsed with pyridine (5×5 ml). A 10 mg sample of the dried CPG was treated with 3% trichloroacetic acid in dichloromethane. The presence of the trityl ion qualitatively verified the derivatization. The loading was measured to be 30 μmol/g by measuring the absorbance of the dimethoxytrityl cation.

EXAMPLE 27

Synthesis of 10-O-(Dimethoxytrityl)-1-decanol

A solution of decane-1,10-diol in dry pyridine and containing excess triethylamine is treated with one equivalent of dimethoxytrityl chloride for a period of six hours. The resulting solution is evaporated to dryness under reduced pressure, the residue redissolved in methylene chloride and the solution washed with cold saturated sodium bicarbonate, water and brine. The organic phase is separated, dried over sodium sulfate, filtered and again evaporated under reduced pressure. The resulting residue is flash-chromatographed on silica gel using ethyl acetate-hexanes to isolate the purified product. Characterization by H-NMR yields signals for the DMT group (multiplet, 8.0–7.0 ppm), the decane group (multiplets, 1.2–4.0 ppm) and the alcohol (variable).

EXAMPLE 28

Synthesis of 10-O-(Dimethoxytrityl)decyloxyphosphonic acid

A solution of three equivalents of imidazole in dry acetonitrile is treated dropwise with one equivalent of PCl3 over a period of 30 minutes. The resulting solution is further treated with excess triethylamine to drive the reaction to completion. After 1 hr the mixture is treated with a solution of one equivalent of 10-O-(dimethoxytrityl)decan-1,10-diol in dry acetonitrile and the mixture stirred at room temperature for an additional hour. This mixture is treated with an excess of a solution of triethylammonium bicarbonate, pH 8, to yield the title compound. The compound is purified by repeated extraction of the bicarbonate solution with ethyl acetate. Pooling and drying of the extracts over sodium bicarbonate followed by evaporation of the solvent under reduced pressure yields a compound which is used as such without further purification. Characterization by $^{31}$P NMR (doublet, 6 ppm, JP-H=600 Hz) and $^1$H NMR yields signals for the DMT and the decane groups as for 10-O-(dimethoxytrityl)decandiol and signals for the triethylammonium groups (doublet, triplet, 3.2–2.2 ppm).

EXAMPLE 29

Synthesis of 10-O-(Dimethoxytrityl)decylsuccinate Half Ester

A solution of 10-O-(dimethoxytrityl)decan-1,10-diol in dry dichloromethane is treated with one equivalent of succinic anhydride, excess triethylamine and 5 mole % of 4-dimethylaminopyridine catalyst. The mixture is stirred overnight under anhydrous conditions and then further diluted with dichloromethane. This solution is washed with cold, saturated sodium bicarbonate, water and brine. The solution is then dried over magnesium sulfate, filtered and evaporated to dryness under reduced pressure. The resulting solid is purified by silica gel flash column chromatography using ethyl acetate-methanol-triethylamine to yield the title compound as the triethylammonium salt. The free acid is obtained by repeated coevaporation of this material with wet methanol. Characterization by $^1$H NMR yields signals for the DMT and decylene groups as for 10-O-(dimethoxytrityl) decan-1,10-diol and signals for the succinic group (two closely spaced doublet of doublets, 2.5–3.0 ppm).

EXAMPLE 30

Derivatization of LCAA CPG with 10-O-(Dimethoxytrityl)decylsuccinate Half Ester

A commercially obtained sample of controlled pore glass derivatized with long chain alkylamine groups (LCAA CPG) is suspended in dry acetonitrile. In a separate dry container, 10-O-(dimethoxytrityl)decylsuccinate half ester is treated with two equivalents of pentafluorophenol, excess triethylamine and two equivalents of dicyclohexyl carbodiimide. The mixture containing activated 10-O-(dimethoxytrityl) decylsuccinate half ester is stirred under argon for one hour and then added to the suspension of CPG while maintaining anhydrous conditions. The mixture is then shaken gently for 6 hr, the supernatant is separated and the process is repeated twice more. The quantity of 10-O-(dimethoxytrityl) decylsuccinate half ester which is used in each treatment is based on the concentration of available amine groups per gram of LCAA CPG, generally found to be 25–40 mmoles/gram. The CPG is then treated with a dilute solution of acetic anhydride in pyridine for 1 hr to cap all unreacted amine functionalities and then washed several times with acetonitrile. The extent to which this CPG has been derivatized is determined by treating an accurately weighed sample of the resulting CPG with 2% dichloroacetic acid in acetonitrile and measuring the absorbance of an aliquot of the supernatant at 498 nm.

EXAMPLE 31

2-N-Fmoc-2-Amino-1,3-Propanediol

2-Amino-1,3-propanediol (3.48 g, 38.2 mmol) and NaHCO$_3$ (8.00 g, 95.2 mmol) are suspended in 150 ml H$_2$O/Dioxane (1:1). Fluorenylmethyl chloroformate (11.4 g, 44.0 mmol) in 25 ml toluene is added dropwise. The temperature of the reaction is maintained below 25° C. during the addition. The mixture is stirred vigorously overnight, and then quenched with 50 ml saturated NaHCO$_3$ solution and 50 ml water. The solution is extracted with 100 ml diethyl ether. The aqueous layer is acidified to pH 1 with concentrated HCl, and extracted twice with ethyl acetate, and the organic extracts are washed with brine. The solution is dried with MgSO$_4$, filtered and the solvent removed in vacuo. The crude material is purified by silica gel column chromatography to give the title compound.

EXAMPLE 32

1-O-Dimethoxytrityl-N-Fmoc-2-Aminopropan-3-ol

A solution of N-Fmoc-2-amino-1,3-propanediol (13.79 g, 44 mmol) in dry pyridine (250 ml) is cooled to 0° C. in an ice bath. Excess triethylamine (7 ml) and 4-dimethylaminopyridine catalyst (120 mg, 1 mmol) is added followed by the slow addition of dimethoxytrityl chloride (14.8 g, 44 mmol) over 30 minutes. The mixture is stirred at 0° C. until complete. The resulting solution is quenched with methanol and evaporated to dryness under reduced pressure. The residue is dissolved in saturated $NaHCO_3$ and extracted with EtOAc. The EtOAc extracts are washed with cold saturated sodium bicarbonate and brine. The organic phase is separated, dried over sodium sulfate, filtered and evaporated under reduced pressure. The resulting residue is purified by flash column chromatography on silica gel to give the title compound.

EXAMPLE 33

1-O-Dimethoxytrityl-N-Fmoc-2-Aminopropane-3-O-phosphonic Acid

A solution of imidazole (4.29 g, 63 mmol) in dry acetonitrile at 0° C. (300 ml) is treated dropwise with $PCl_3$ (1.77 ml, 20.3 mmol) over a period of 30 minutes. The resulting solution is further treated with triethylamine (9.06 ml, 65 mmol). To the thick slurry was added 1-O-Dimethoxytrityl-N-Fmoc-2-Aminopropan-3-ol (3.58 g, 5.81 mmol) in anhydrous acetonitrile (150 ml) slowly over a period of 30 minutes. The mixture is allowed to warm to room temperature and stirred for 15 minutes. The mixture is quenched with pyridine/water 9:1 (100 mL) and the mixture is evaporated in vacua to a minimum volume and extracted with dichloromethane (2×150 ml). The dichloromethane extracts are washed with water and evaporated in vacuo. The residue is purified by silica gel column chromatography using dichloromethane/MeOH/pyridine to give the title compound.

EXAMPLE 34

1-O-Dimethoxytrityl-N-Fmoc-2-Aminopropane-3-O-Succinate

1-O-Dimethoxytrityl-N-Fmoc-2-aminopropan-3-ol is treated with succinic anhydride as per the general procedure of Example 60 to give the title compound.

EXAMPLE 35

Derivatization of LCAA CPG with 1-O-Dimethoxytrityl-N-Fmoc-2-Aminopropane-3-O-Succinate 1-O-Dimethoxytrityl-N-Fmoc-2-Aminopropane-3-O-Succinate ester is coupled onto LCAA CPG as per the general procedure of Example 61 to give the derivatized resin.

EXAMPLE 36

1-O-Dimethoxytrityl-2-Aminopropan-3-ol Succinate Derivatized Resin

The Fmoc protecting group on the 2-amino group of the 1-O-dimethoxytrityl-N-Fmoc-2-amino-1,3-propan-3-ol succinate derivatized CPG is removed by treatment with piperidine in dimethylformamide (DMF). CPG bound 1-O-dimethoxytrityl-N-Fmoc-2-amino-1,3-propanediol is treated with 2 equivalents of piperidine in DMF. The CPG is then washed with acetonitrile/pyridine 1:1 and then treated a second time with 2 equivalents of piperidine in DMF. Finally, the CPG is washed with acetonitrile-pyridine and then acetonitrile to give the deprotected material.

EXAMPLE 37

1-O-Dimethoxytrityl-2-N-(acetylthymine)amino-1,3-Propanediol Succinate Derivatized Resin Method A The 1-O-dimethoxytrityl-2-aminopropane-3-ol succinate derivatized resin (2.0 g, 1.0 mmol/gm loading, 1% cross-linked) is swollen in dichloromethane (200 mL) and to this is added thymine-2-acetic acid (2.0 g, 10 mmol), [O-(7-azabenzotriazol-1-yl)-1,1,3,-tetramethyluronium hexafluorophosphate (3.8 g, 10 mmol) and triethylamine (2.0 g, 20 mmol). After 30 to 60 minutes the resin is washed 5 times with dichloromethane (50 mL), then 3 times with diethyl ether (100 mL), and is dried under a stream of nitrogen. The free flowing resin powder is used as is.

Method B

The 1-O-dimethoxytrityl-2-amino-1,3-propanediol succinate derivatized resin (2.0 g, 1.0 mmol/gm loading, 1% cross-linked) is swollen in dichloromethane (200 mL) and to this is added HOBt (0.1 M), PyBOP (0.1 M), N-methylmorpholine (0.15 M), as solutions in DMF followed by thymine-2-acetic acid (2.0 g, 10 mmol). Coupling is allowed to proceed for 2–3 hours or overnight. The resin is washed 5 times with dichoromethane (50 mL), then 3 times with diethyl ether (100 mL), and is dried under a stream of nitrogen. The free flowing resin powder is used as is.

EXAMPLE 38

Sequential Addition and Functionalization of n Backbone Segments

The dimethoxytrityl protecting group of the derivatized resin of Example 37 is removed by a treatment with a solution of trichloroacetic acid (3% w/v) in dichloromethane. The solution is passed over the solid support until the DMT cation color is completely gone. The solid support is washed with dichloromethane until no trace of acid remains. The resin is then washed with acetonitrile-pyridine (4:1) followed by a simultaneous treatment of the CPG with 10 equivalents of 1-O-dimethoxytrityl-N-Fmoc-2-amino-3-O-phosphonic acid and 30 equivalents of adamantane carbonyl chloride in acetonitrile-pyridine (1:1). The mixture is agitated by circulating the reagents in the synthesis vessel for 2 minutes. The CPG is then briefly washed with acetonitrile-pyridine and then treated with diisopropyl phosphite adamantane carbonyl chloride to cap all unreacted hydroxyl groups. The CPG is washed with acetonitrile-pyridine and then acetonitrile. The resulting phosphonic acid diester is reacted with a large molar excess of 10% diethylamine (the amine letter) in carbon tetrachloride/pyridine (1:1). The solid support is shaken for 15 minutes and the supernatant is removed by filtration. The solid support is washed with pyridine. A second treatment with diethylamine in carbon tetrachloride/pyridine followed by shaking will ensure efficient oxidation to the phosphoramidate. The Fmoc protecting group is removed as per the general procedure of Example 62. The resulting free amine group is treated with thymine-2-acetic acid as per the procedure of Example 37. This procedure is repeated twice to give a dimer having thymineacetyl groups corresponding to the letter and the tether covalently bound to the amine group attached to carbon in the backbone segment. The functional groups bound to the phosphoramidate nitrogen are ethyl groups. This procedure when repeated n times will give a fully functionalized oligomer that is n+1 backbone segments long.

Upon completion of the addition of the last of the desired length and configuration of oligomeric sequence, the solid support is washed with pyridine/acetonitrile and the phosphoramidate is cleaved from the resin by treatment with concentrated ammonium hydroxide at room temperature for 3 hours. Evaporation of the supernatant and purification of the phosphoramidate on an RP-18 HPLC column yields the final oligomer.

EXAMPLE 39

N-Fmoc-Aspartic Acid-β-Benzyl Ester

Aspartic acid-β-benzyl ester (150 mmol) and diisopropylethylamine (66.3 ml, 49.1 g, 380 mmol) are suspended in 150 ml H$_2$O+300 ml dioxane. Fluorenylmethyl chloroformate (43.25 g, 1.1 eq) in 100 ml dioxane is added dropwise. The temperature of the reaction is not allowed to rise above 10° C. during the addition. The mixture is stirred vigorously overnight, and most of the solvent removed in vacuo. Water and satd bicarbonate solution are added (250 ml each), and the solution extracted with 250 ml diethyl ether, which is discarded. The aqueous layer is acidified to pH 1 with conc HCl, and extracted twice with ethyl acetate (2×300 ml), and the organic extracts washed with brine. The solution is dried with MgSO$_4$, filtered and the solvent removed in vacuo to give the title compound.

EXAMPLE 40

4-Hydroxy-2-N-Fmoc-aminobutanoic acid

2-N-Fmoc-aspartic acid-β-benzyl ester (10 mmol) is dissolved in dry THF (100 ml), cooled to 0° C. and Lithium borohydride (15 mmol) added. The solution is stirred at 0° C. and then room temperature until the complete disappearance of the starting material. Excess ethyl acetate is then added, and the solution is washed with 0.1M citric acid solution, brine and dried with MgSO$_4$. The crude material is purified by flash chromatography to give the title compound.

EXAMPLE 41

4-O-Dimethoxytrityl-2-N-Fmoc-aminobutanoic acid

4-Hydroxy-2-N-Fmoc-aminobutanoic acid (30 mmol) is coevaporated with dry pyridine (2×50 ml), redissolved in 200 ml dry pyridine, and cooled in an ice bath. Dimethoxytrityl chloride (22.0 g, 65 mmol) is added in portions over 30 min, and the solution stirred at RT overnight. Water is then added (10 ml), and the solution stirred until the trityl ester is completely hydrolyzed. The solvent is removed under reduced pressure. The residue is dissolved in CH$_2$Cl$_2$ (300 ml), washed with 150 ml 0.1 M citric acid solution, 150 ml sat NaHCO$_3$, brine, and dried with MgSO$_4$ followed by evaporation. The residue is purified by flash chromatography.

EXAMPLE 42

4-O-Dimethoxytrityl-2-N-Fmoc-aminobutan-1-ol

To a stirred solution of 4-O-Dimethoxytrityl-2-N-Fmoc-aminobutanoic acid (140 mmol) in 500 ml THF is added Borane-methyl sulfide (290 mmol, 21.8 g, 27.3 ml) dropwise at RT. Stirring is continued until the reaction is complete. Methanol is carefully added (vigorous H$_2$ evolution), and the resulting solution stirred for a further 15 min. The solvent is evaporated under reduced pressure, and the residual gum coevaporated with 2×300 ml MeOH. The product is purified by flash chromatography.

EXAMPLE 43

1-O-Dimethoxytrityl-2-N-Fmoc-2-Aminobutane-4-O-Phosphonic Acid

1-O-Dimethoxytrityl-2-N-Fmoc-2-aminobutan-4-ol is treated as per the general procedure of Example 59 to give the title compound.

EXAMPLE 44

1-O-Dimethoxytrityl-2-N-Fmoc-2-Aminobutan-4-O-Succinate

1-O-Dimethoxytrityl-2-N-Fmoc-2-aminobutan-1-ol is treated as per the general procedure of Example 60 to give the title compound.

EXAMPLE 45

1-Derivatization of LCAA CPG with 1-O-Dimethoxytrityl-2-N-Fmoc-2-Aminobutane-4-O-Succinate 1-O-Dimethoxytrityl-2-N-Fmoc-2-aminobutane-4-O-succinate is treated as per the general procedure of Example 61 to give the derivatized resin.

EXAMPLE 46

1-O-Dimethoxytrityl-2-Aminobutane-4-O-Succinate Derivatized Resin

The derivatized resin of Example 45 is treated as per the general procedure of Example 62 to remove the Fmoc protecting group giving the title compound attached to resin.

EXAMPLE 47

1-O-Dimethoxytrityl-2-(N-2-Acetylthymine)-Aminobutane-4-O-succinate Derivatized Resin The derivatized resin of Example 46 is treated with N-1-thymine-2-acetic acid as per the procedure of Example 37 to give the title compound attached to resin.

EXAMPLE 48

Synthesis of a 3-mer Having the 2-Amino-1,4-Butanediol Backbone Segment

1-O-Dimethoxytrityl-2-(N-2-acetylthymine)-aminobutane derivatized resin is treated with 1-O-dimethoxytrityl-2-N-Fmoc-2-amino-4-phosphonic acid-1,4-butanediol, morpholine, and N-1-thymine acetic acid as per the procedures of Example 38 and Example 126 to give a 3 mer with 2-N-acetylthymine bound to the amino groups and morpholine groups as the phosphoramidate substituent.

EXAMPLE 49

2-(N-Fmoc)-Glutamic acid-γ-methyl ester

Glutamic acid-γ-methyl ester (150 mmol) and diisopropylethylamine (66.3 ml, 49.1 g, 380 mmol) are suspended in 150 ml H₂O+300 ml dioxane. Fluorenylmethyl chloroformate (43.25 g, 1.1 eq) in 100 ml dioxane is added dropwise. The temperature of the reaction is not allowed to rise above 10° C. during the addition. The mixture is stirred vigorously overnight, and most of the solvent removed in vacuo. Water and satd bicarbonate solution are added (250 ml each), and the solution extracted with 250 ml diethyl ether, which is discarded. The aqueous layer is acidified to pH 1 with conc HCl, and extracted twice with ethyl acetate (2×300 ml), and the organic extracts washed with brine. The solution is dried with MgSO₄, filtered and the solvent removed in vacuo to give the title compound.

EXAMPLE 50

5-Hydroxy-4-N-Fmoc-aminopentanoic acid methyl ester

To a solution of 2-(N-Fmoc)-glutamic acid-γ-methyl ester (140 mmol) in 500 ml THF is added Borane-methyl sulfide (290 mmol, 21.8 g, 27.3 ml) dropwise at RT (3 neck flask, mechanical stirrer, condenser, dropping funnel). After the evolution of H₂ has ceased, the solution is heated to reflux with vigorous stirring. After 1 hr a white precipitate has formed. Methanol is carefully added (vigorous H₂ evolution), and the resulting solution refluxed for a further 15 min. The solution is cooled to RT, the solvents evaporated under reduced pressure, and the residual gum coevaporated with 2×300 ml MeOH. The product is purified by flash chromatography.

EXAMPLE 51

5-O-Dimethoxytrityl-4-Fmoc-aminopentanoic acid methyl ester

5-Hydroxy-4-N-Fmoc-aminopentanoic acid methyl ester (30 mmol) is coevaporated with dry pyridine (2×50 ml), redissolved in 200 ml dry pyridine, and cooled in an ice bath. Dimethoxytrityl chloride (11.0 g, 32.5 mmol) is added in portions over 30 min, and the solution stirred at 0° C. overnight. Methanol is then added (10 ml), and the solvent removed under reduced pressure. The resulting gum is redissolved in toluene (100 ml), filtered to remove the pyridinium hydrochloride and taken to dryness again. The residue is dissolved in CH₂Cl₂ (300 ml), washed with 150 ml 0.1 M citric acid solution, 150 ml sat NaHCO₃, brine, and dried with MgSO₄ followed by evaporation. The residue is purified by flash chromatography to give the title compound.

EXAMPLE 52

5-O-Dimethoxytrityl-4-Fmoc-aminopentan-1-ol

5-O-Dimethoxytrityl-4-Fmoc-aminopantanoic acid methyl ester (10 mmol) is dissolved in dry THF (100 ml), cooled to 0° C. and Lithium borohydride (10 mmol) added. The solution is stirred at 0° C. and then room temperature until the complete disappearance of the starting material. Excess ethyl acetate is then added, and the solution washed with 0.1M citric acid solution, sat NaHCO₃, brine and dried with MgSO₄. The product is purified by flash chromatography

EXAMPLE 53

5-O-Dimethoxytrityl-4-N-Fmoc-aminopentan-1-ol hydrogen phosphonate

Imidazole (6.81 g, 100 mmol) is dissolved in 400 ml dry CH₃CN and cooled to 0° C. Phosphorus trichloride (2.62 ml, 4.12 g, 30 mmol) is added dropwise, followed by triethylamine (21 ml, 15.2 g, 150 mmol). A thick slurry develops to which is added over 15 min a solution of 5-O-dimethoxytrityl-4-N-Fmoc-2-amino-1,5-pentanediol (10 mmol) in 50 ml CH₃CN. Once the addition is complete, the ice bath is removed and the solution stirred at RT for 30 min. The reaction is stopped by the addition of 100 ml pyridine/water (9:1). The solvent is removed and the residue extracted (3×200 ml) with CH₂Cl₂, and washed with water. The organic phase is dried with MgSO4 and concentrated under reduced pressure. The product is further purified by flash chromatography using a gradient of MeOH (1–10%) in CH₂Cl₂+1% pyridine.

EXAMPLE 54

5-O-Dimethoxytrityl-4-N-Fmoc-Aminopentane-1-O-Succinic Acid Half Ester

5-O-Dimethoxytrityl-4-N-Fmoc-aminopentane-1-ol is treated as per the general procedure of Example 60 to give the title compound.

EXAMPLE 55

Derivatization of LCAA CPG with 5-O-Dimethoxytrityl-4-N-Fmoc-Aminopentane-1-O-Succinic Acid Half Ester 5-O-Dimethoxytrityl-4-N-Fmoc-Aminopentane-1-O-Succinic Acid Half Ester is treated as per the general procedure of Example 61 to give the derivatized resin.

EXAMPLE 56

5-O-Dimethoxytrityl-4-Aminopentane-1-O-Succinic acid Derivatized Resin

The derivatized resin of Example 55 is treated as per the procedure of Example 62 to remove the Fmoc protecting group giving the title compound attached to resin.

EXAMPLE 57

5-O-Dimethoxytrityl-4-N-Phenylacetyl-Aminopentane-1-O-Succinic acid Derivatized Resin The derivatized resin of Example 56 is treated with phenyl acetic acid as per the procedure of Example 38 to give the title compound attached to resin.

EXAMPLE 58

Synthesis of a 3-mer Having the 2-amino-1,5-pentanediol Backbone Segment

1-O-Dimethoxytrityl-2(phenylacetyl)-Amino-5-Phosphonic Acid-1,5-pentanediol Derivatized Resin is treated with 1-O-dimethoxytrityl-2-N-Fmoc-2-amino-5-phosphonic acid-1,5-pentanediol, morpholine, and phenylacetic acid as per the procedure of Example 38 and Example 126 to give a 3 mer with phenylacetyl bound to the amino groups and morpholine groups as the phosphoramidate substituent.

EXAMPLE 59

General Procedure for Converting Aminodiol Monomer Subunits to the H-Phosphonate Monoesters N-Fmoc-5-Dimethoxytrityloxymethylpyrrolidine-3-O-Hydrogen Phosphonate Triethylammonium salt Imidazole (6.81 g, 100 mmol) was dissolved in 400 ml dry CH3CN and cooled to 0° C. Phosphorus trichloride (2.62 ml, 4.12 g, 30 mmol) was added dropwise, followed by triethylamine (21 ml, 15.2 g, 150 mmol). A thick slurry developed to which was added over 15 min a solution of N-Fmoc-5-dimethoxytrityloxymethyl-3-hydroxypyrrolidine (10 mmol) in 50 ml CH3CN. Once the addition was complete, the ice bath was removed and the solution stirred at RT for 30 min. The reaction was stopped by the addition of 100 ml Pyridine and 10 ml water. The solvent was removed and the residue coevaporated with 100 ml Pyridine, then 100 ml toluene. The residue was then dissolved in 0.05M TEAB, extracted (3×200 ml) with CH2Cl2, and the extract washed with 0.05M TEAB. The organic phase was dried with MgSO4 and concentrated under reduced pressure. The product was further purified by flash chromatography using a gradient of MeOH (1–10%) in CH2Cl2+0.5% TEA.

EXAMPLE 60

General Procedure for Converting Aminodiol Monomer Subunits to the Succinate Derivatives
N-Fmoc-5-Dimethoxytrityloxymethylpyrrolidine-3-O-Succinate N-Fmoc-5-Dimethoxytrityloxymethylpyrrolidine (2.0 mmol), succinic anhydride (300 mg, 3.0 mmol), DMAP (1.0 mmol, 120 mg) and triethylamine (0.4 ml, 3.0 mmol) are dissolved in dichloromethane and stirred overnight. The solution is extracted with dichloromethane, washed with 0.1M citric acid, water, brine, dried and evaporated. The residue is filtered through a short pad of silica and used directly.

EXAMPLE 61

N-Fmoc-5-Dimethoxytrityloxymethylpyrrolidine-Controlled Pore Glass (N-FMOC-5-DMT-hp-CPG)

N-Fmoc-5-Dimethoxytrityloxymethylpyrrolidine-3-O-Succinate is dissolved in dry dichloromethane (50 ml), DMAP added (250 mg, 2 mmol) followed by toluenediisocyanate (288 ul, 2.0 mmol). The mixture is swirled for 10 min then 10 g LCAA-CPG is added followed by DIEA (2 mmol, 0,34 ml). The suspension is kept in the dark and agitated periodically for 6–16 h. The solid is filtered, washed with dichloromethane and ether, then suspended in 80 ml pyridine+20 ml water. After 1 h, the support is filtered, washed with dry pyridine (5×), dichloromethane (3×), and suspended in 60 ml dichloromethane, to which 10 ml TEA, 10 ml acetic anhydride, 3 ml N-methylimidazole are added. After 1 h, the support is filtered, washed extensively with dichloromethane and ether and dried. The CPG is analyzed for loading by weighing a portion of CPG, dissolving in 0.1M toluene sulfonic acid and measuring the absorbance at 498 nm.

EXAMPLE 62

Deprotection of Backbone Segment Amino Combinatorial Site Protecting Groups General Procedure The solid support (1–10 umol) bearing an EMOC protected amine is washed with a 10% (v/v) solution of piperidine in DMF for 15 seconds, and suspended in the piperidine solution for 15 minutes. The solvent is removed and a fresh portion of piperidine/DMF is added for a further 15 minutes. The solid support is then washed with several portions of DMF to remove all traces of piperidine.

Using this procedure the Fmoc protected backbone segment amino combinatorial site of the solid support bound N-Fmoc-5-dimethoxytrityloxymethylpyrrolidine of Example 61 is deprotected.

EXAMPLE 63

Coupling of Carboxylic Acids to Backbone Segment Amino Combinatorial Sites General procedure Deprotected backbone segment amino combinatorial sites are treated simultaneously with a solution of a carboxylic acid (0.4 mmol/ml) and diisopropylethylamine (0.8 mmol/ml) in DMF, and BOP reagent or HATU(0.4 mmol/ml) in DMF. A tenfold excess of reagents are added at the 10 umol scale level. The reaction is allowed to proceed for 30 minutes and a further ten equivalents of carboxylic acid and BOP is added. After 30 minutes, the solid support is washed with DMF until all the reagents are removed.

EXAMPLE 64

Removal of the DMT Protecting Group General Procedure

Aminodiol monomeric subunits having dimethoxytrityl protecting group are deprotected using a solution of trichloroacetic acid (3%, w/v) in dichloromethane is passed over the solid support until the DMT cation color is completely gone. The solid support is washed with dichloromethane until no trace of acid remains.

EXAMPLE 65

Coupling of Sulfonyl Chlorides to Backbone Segment Amino Combinatorial Site General Procedure To the free amine on solid support obtained by piperidine treatment of the FMOC protected backbone segment is added simultaneously a solution of a sulfonyl chloride (0.1 mmol/ml) and diisopropylethylamine (0.25 mmol/ml) in pyridine/CH3CN. A tenfold excess of reagents is added at the 10 umol scale level. The reaction is allowed to proceed for 30 minutes, and the solid support was washed with Pyridine/CH3CN until all the reagents are removed.

EXAMPLE 66

Coupling of Acyl Groups to Backbone Segment Amino Combinatorial Site General Procedure To the free amine on solid support are added simultaneously a solution of an activated acylating agent (0.1 mmol/ml) and diisopropylethylamine (0.25 mmol/ml) in Pyridine/$CH_3CN$. A tenfold excess of reagents are added at the 10 umol scale level. The reaction is allowed to proceed for 30 minutes, the solid support is washed with Pyridine/$CH_3CN$ until all the reagents are removed. Groups useful for acylating the free amine combinatorial site include acid halides, acid fluorides, acid imidazolides, acid anhydrides, sulfonyl chlorides, chloroformates, isocyanates, isothiocyanates.

EXAMPLE 67

Phosphoramidate Library Synthesis General Procedures

The general procedures described below outline the methods for the preparation of phosphoramidate combinatorial libraries. All manipulations can be accomplished using an automated synthesizer to deliver solvents and reagents to a reaction vessel containing the reactants attached to a solid support, usually controlled pore glass (CPG) or Tentagel (TG). The design of such synthesizers and the loading of the solid support allow the manipulations to be performed on scales ranging from 50 pmol to approximately 10 mmol if desired. The manipulations can also be carried out manually by using a syringe with a glass frit as the reaction vessel, by drawing the appropriate solutions into the syringe. The reactions described can be carried out on single compounds attached to the solid support, or on complex mixtures prepared by the technique of bead portioning/mixing. In brief, these techniques involve the addition of unique reagents to an equal number of separate portions of solid support. Once the individual reactions are complete, the portions of solid support are combined and mixed thoroughly as a slurry in an appropriate solvent and redivided into the number of portions required by the number of different reagents in the next step. In this way, a unique reagent is added to a mixture of compounds, to create all possible combinations of the different reagents.

Oxidation of H-Phosphonate Diester linkages to Form Phosphoramidate Linkages Having Letters Method A: Incorporation of Letters in Predetermined Sequence The solid support (e.g. LCAA CPG) is derivatized with a first monomeric subunit or other group having a terminal reactive group capable of forming a covalent bond with a primary or secondary amine. Example 26 illustrates a non-aminodiol monomer subunit attached to a solid support and Example 45 illustrates attachment of an aminodiol monomer subunit to a solid support. When an aminodiol monomer subunit is derivatized to the solid support the amino group is deprotected using the general procedure of Example 62 and coupled with a letter having an optional tether as illustrated in Examples 36, 37, 63, and 65(also see Examples 122–130). The hydroxyl protecting group is then removed as illustrated in Example 64 and the next desired aminodiol monomer subunit having a phosphonic acid monoester group on one of the hydroxyls is condensed onto the terminal free hydroxyl of the derivatized solid support as per the procedure of Example 48. The resulting phosphonic acid diester is reacted with a large molar excess of a primary or secondary amine in carbon tetrachloride/pyridine to form the phosphoramidate having a letter attached thereto. The amine letter is added in a solution of carbon tetrachloride/pyridine. The solid support is washed with pyridine. A second treatment with a large molar excess of the amine letter in carbon tetrachloride/pyridine followed by shaking will ensure efficient oxidation to the phosphoramidate. The amino protecting group on the second backbone substituent is removed using piperidine treatment and the free amino is coupled to a letter as above. In this case the procedures give an oligomeric compound two units in length.

Additional functionalized monomer units can be added by repeating the following steps as often as desired: 1) removal of the oxygen protecting group, 2) coupling of an additional scaffold phosphonate monoester, 3) oxidation of the phosphonate diester with carbon tetrachloride in the presence of the desired amine letter, 4) removal of the nitrogen protecting group on the last scaffold monomer unit, 5) functionalization of the amino group with the desired functionality.

The oxidative incorporation of letters to form phosphoramidate linkages can be performed stepwise or all at once for a uniform substitution of letters. For the addition of two adjacent like letters in the oligomeric structure, the oxidation step can delayed until the backbone to support all of these letters is synthesized and all H phosphonate sites that will bear this letter are then oxidized simultaneously.

The above steps are repeated until all of the letters of the oligomer have been added. All letters are predetermined in this method of synthesis. Upon completion of the addition of the last of the desired length and configuration of the oligomeric compound, the solid support is washed with pyridine/acetonitrile and the phosphoramidate is cleaved from the resin by treatment with concentrated ammonium hydroxide at room temperature for 3 hours. Evaporation of the supernatant and purification of the phosphoramidate on an RP-18 HPLC column yields the final oligomer.

Method B: Incorporation of Phosphoramidate Letters in a Random Sequence

The method of oligomer synthesis as described above in Method A is repeated to synthesize the oligomer of desired length. To randomize the amine letters on the oligomer, the method of adding a letter as described in Method a above is followed except that, for randomization, the amine letters in carbon tetrachloride and a suitable cosolvent are added as a mixture, preferably one normalized for relative reactivity. Random distribution of amine letters from this mixture of amine letters is verified experimentally by treatment of an oligomer, which has been previously treated with a mixture of amine letters and subsequently worked up and purified, with 10% aqueous formic acid at 50–70° C. to release the amine letters. The actual percentages of incorporation of the individual amine letters is then determined by HPLC analysis of the reaction mixture and the relative individual rates are calculated. Having once determined the relative rates, in further iteration of the sequences, the concentration of amine letters within a mixture is adjusted to reflect these rate differences.

In a variation of this method of randomization, in a five mer all sites of which are to be randomized, the oxidation is effected simultaneously. The five mer backbone is synthesized as above and a mixture of the letters added. Upon completion of the backbone synthesis, the oxidation of amine letters is effected on all five sites as a single step.

In a further variation of this method of randomization, upon completion of the synthesis of the first backbone segment, the resin is split into five portion and each portion is individually oxidized with one of the amine letter. The individual portions of the resin are recombined and a further backbone segment is attached thereby extending the oligomeric compound a further unit. The resin is then again split, and the individual portion each oxidized with one of the amine letter. This cycle is repeated to complete the synthesis.

A Coupling of letters to the free amino positions is performed as in Method A for a predetermined sequence or Method B for a random sequence.

Method C: Incorporation of Amine Letters in Fixed/random Sequence

Combining methods A and B above can be used to fix certain positions while randomizing other positions as the oligomeric compound is synthesized. This method is further used in combination with a SURF™ combinatorial strategy.

The following is a representative list of amine letters:
allylamine
3,3-Dimethylaminopropylamine
1-Phenyl-1,3,8-Triazaspiro[4.5]decan-4-one
Azetidine
Benzylamine
Butylamine
L-(−)-2-Aminocaprolactam
Heptamethyleneimine cyclopropylamine
Diethylamine
Dimethoxyethylamine
2,5-Dimethyl-N-phenylpiperazine
Methylaminomethyl-1,3-dioxolane
N-Acetyl Ethylenediamine
3-Aminopropyl Imidazole
Methoxyethylamine
Morpholine
3-Aminopropyl Morpholine
Isonipecotamide
Piperonylamine
2-Aminomethylpyridine
Piperidine
Piperidone ethylene ketal
2-Aminoethyl-1-methylpyrrolidine
N(2-Pyridyl)piperazine
Piperonylpiperazine
3-Isopropoxypropylamine
Piperazine
Thienylethylamine
3-Trifluoromethoxybenzylamine
Tryptamine
Tetrahydrofurfurylamine

EXAMPLE 68

1-Acetyl Thymine/Benzylamine Phosphoramidate Oligomer Synthesis

A solid support is derivatized with 2-O-(dimethoxytrityl) ethylsuccinate half ester as in Example 26. The DMT protecting group is removed using the standard method of Example 64. 4-O-Dimethoxytrityl-2-N-Fmoc-aminobutan-1-ol is treated with $PCl_3$ as per Example 28 to form the phosphonic acid which is condensed onto the derivatized resin as in Example 38. The Fmoc amino protecting group is removed as per Example 4 and (N1-thymine)-2-acetic acid (Example 7) is coupled to the resulting free amino as per the method of Example 38. The above methods of examples 64, 28, 37 and 38 are repeated until six of the above phosphonic acid residues are incorporated. The resulting six mer is treated using the procedures of Example 67, with a large excess of benzylamine in carbon tetrachloride/pyridine. The solid support is shaken for 15 minutes and the supernatant is removed by filtration and then washed with pyridine. A second treatment with a large excess of benzylamine in carbon tetrachloride/pyridine followed by shaking will insure efficient oxidation to the phosphoramidate. The resin is washed with pyridine/acetonitrile and then the phosphoramidate is cleaved from the resin by a treatment with concentrated ammonium hydroxide at room temperature for 3 hours. Evaporation of the supernatant and purification of the phosphoramidate on an RP-18 HPLC column will yield the final oligomer. The stepwise H phosphonate coupling efficiency is determined by is measuring the absorbance of the trityl ion. The resulting six mer will have a benzylamine at each of the phosphoramidate linkages and will have an acetylthymine group at each of the backbone segment amino combinatorial sites.

EXAMPLE 69

Hydrogen Phosphonate Coupling General Procedure

A portion of solid support (CPG or other polymeric support e.g. TentaGel) derivatized with a DMT protected alcohol linked via a succinate linker (1 µmol) is loaded into a DNA synthesis column, and attached to an automated DNA synthesizer programmed to perform the following functions:
1) Wash with dichloromethane;
2) Treat with 3% trichloroacetic acid in dichloromethane to remove the DMT protecting group;
3) Wash with dichloromethane and $CH_3CN$/Pyridine (1:1);
4) Coupling: addition of alternating portions of 0.2 M Adamantoyl chloride or Pivaloyl chloride in $CH_3CN$/Py (1:1) and 0.05 M H-phosphonate monomer in $CH_3CN$/Py (1:1) for 1 min;
5) Wash with $CH_3CN$/Pyridine (1:1);
6) Stop and proceed to an oxidation procedure for oxidation of each linkage independently or repeat steps 1 through 5 to add additional monomer subunits prior to oxidation.

The product of this sequence of reactions is an H-phosphonate diester, which is oxidized by one of several methods including those described below.

Oxidation Procedure 1: Phosphodiester

The solid support-bound H-phosphonate diester is treated (manually or automatically) with equal volumes of solution A (0.2 M $I_2$ in THF) and solution B (N-methylmorpholine/$H_2O$/THF 1:1:8) for 5 min, followed by equal volumes of solution A and solution C (TEA/$H_2O$/THF 1:1:8) for 5 min, followed by washing with $CH_3CN$/Py (1:1).

Oxidation Procedure 2: Phosphorothioate

The solid support-bound H-phosphonate diester is treated (manually or automatically) with a solution of $S_8$ in $CS_2$/Lutidine for 30 min. The solid support is then washed with $CH_3CN$/Py (1:1).

Oxidation Procedure 3: Phosphoramidate

The solid support-bound H-phosphonate diester is treated (manually or automatically) with a solution of the required amine (10% V/V) in $CCl_4$/Pyridine 1:1 for 15–30 min. The solid support is then washed with $CH_3CN$/Py (1:1).

EXAMPLE 70

Combinatorial Library Synthesis Having Phosphoramidate Linkages

N-Fmoc-5-dimethoxytrityloxymethyl-3-hydroxypyrrolidine (Example 2), 1-O-dimethoxytrityl-N-Fmoc-2-amino-1,3-propanediol (Example 32), and 4-O-dimethoxytrityl-2-N-Fmoc-aminobutan-1-ol (Example 42) are treated in separate reactions with succinic anhydride as per example 60 to give the corresponding succinyl derivatives. In a separate set of reactions each of the above aminodiol monomer subunits are treated with $PCl_3$ as per Example 28 to give the corresponding H-phosphonate monoesters. A solid support is divided into three equal portions and each portion is treated with one of the succinyl derivatized aminodiol monomer subunits as per Example 61. The solid support is combined and the amino protecting groups are removed as per the general procedure of Example 62. The solid support is washed with pyridine/acetonitrile, dried, and redivided into three equal parts.

Each portion of the solid support is treated with one of (N1-Thymine)-2-acetic acid (Example 7), (N6-benzoyl-9-adenine)-2-acetic acid (Example 11), or N-4-benzoyl-1-cytosine-2-acetic acid (Example 13) following the general heprocedure of Example 63. The procedure of mixing, drying and redividing the solid support is repeated.

Each portion of solid support is treated with one of the H-phosphonate monoesters above as per the procedure of Example 30, to form the H-phosphonate diesters. The procedure of mixing, drying and redividing the solid support is repeated. Each portion of the solid support is treated with a large molar excess of one of benzylamine, 2-(2-aminoethyl)-1-methylpyrrolidine, or piperonyl amine in carbon tetrachloride/pyridine. The solid support is shaken for 15 minutes and the supernatant is removed by filtration and then washed with pyridine. A second treatment with a large excess of each amine letter in carbon tetrachloride/pyridine followed by shaking will insure efficient oxidation to the phosphoramidate. The solid support is combined and the amino protecting groups are removed as above. The solid support is washed with pyridine/acetonitrile, dried, and redivided.

Each portion of the solid support is treated with one of (N1-Thymine)-2-acetic acid (Example 7), (N6-benzoyl-9-adenine)-2-acetic acid (Example 11), or N-4-benzoyl-1-cytosine-2-acetic acid (Example 13) following the general procedure of Example 63. The procedure of mixing, deblocking the hydroxyl protecting group as per Example 64, drying and redividing the solid support is repeated.

Each portion of solid support is treated with one of the H-phosphonate monoesters above as per the procedure of Example 69 to form the H-phosphonate diesters. The procedure of mixing, drying and redividing the solid support is repeated. Each portion of the solid support is treated with a large molar excess of one of benzylamine, 2-(2-aminoethyl)-1-methylpyrrolidine, or piperonyl amine in carbon tetrachloride/pyridine. The solid support is shaken for 15 minutes and the supernatant is removed by filtration and then washed with pyridine. A second treatment with a large excess of each amine letter in carbon tetrachloride/pyridine followed by shaking will insure efficient oxidation to the phosphoramidate. The solid support is combined and the amino protecting groups are removed as above. The solid support is washed with pyridine/acetonitrile, dried, and redivided.

Each portion of the solid support is treated with one of (N1-Thymine)-2-acetic acid (Example 7), (N6-benzoyl-9-adenine)-2-acetic acid (Example 11), or N-4-benzoyl-1-cytosine-2-acetic acid (Example 13) following the general procedure of Example 63.

The resulting oligomeric compounds are cleaved from the solid support by a treatment with concentrated ammonium hydroxide at room temperature for 3 hours. Evaporation of the supernatant and purification of the phosphoramidate linked oligomeric compounds on an RP-18 HPLC column will yield the final combinatorial libraries consisting of all the possible oligomeric compounds that can be prepared using the three aminodiol monomer subunits, the three functional groups, and the three amines.

EXAMPLE 71

Combinatorial Library Synthesis Having Phosphodiester or Phosphorothioate Linkages A three mer is synthesized using the reagents and procedures of Example 68 except that oxidation of the H-phosphonate diester linkage is accomplished using the procedures illustrated in Example 69, Procedure 1 or 2, to give either uniform phosphodiester or uniform phosphorothioate linkages.

EXAMPLE 72

Combinatorial Library Synthesis Having Mixed Phosphodiester, Phosphorothioate, and Phosphoramidate Linkages A three mer is synthesized using the reagents and procedures of Example 68 except that oxidation of the H-phosphonate diester linkage is accomplished by dividing the solid support into three equal portions and using the procedures illustrated in Example 69, Procedure 1, 2, or 3 to give phosphodiester, phosphorothioate, or phosphoramidate linkages.

EXAMPLE 73

Standard Oligomer Coupling Cycle Using Standard DNA Synthesis Protocols

The oligomeric compounds of the invention are synthesized on an automated DNA synthesizer (Applied Biosystems model 380B) as is done with standard oligonucleotides using standard phosphoramidate chemistry with oxidation by iodine (see, Oligonucleotide Synthesis, A Practical Approach, M. J. Gait., ed., Oxford University Press, New York, 1990). For phosphorothioate oligomeric compounds, the standard oxidation bottle is replaced by 0.2 M solution of 3H-1,2-benzodithiole-3-one 1,1-dioxide in acetonitrile for the step wise thiation of the phosphite linkages. The thiation wait step is increased to 68 sec and is followed by the capping step. After cleavage from the CPG column and deblocking in concentrated ammonium hydroxide at 55° C. (18 hours), the oligomeric compounds can be purified by precipitation twice out of 0.5 M NaCl solution with 2.5 volumes ethanol or by HPLC chromatography using a RP-18 column. Analytical gel electrophoresis is effected in 20% acrylamide, 8 M urea, 454 mM Tris-borate buffer, pH=7.0. Phosphodiester and phosphorothioate oligomeric compounds are judged from polyacrylamide gel electrophoresis as to material length.

EXAMPLE 74

Synthesis of Sequence Specific Pyrrolidine Oligomer Having Phosphodiester Linkages "Aforvirsen" is an anti-papilloma agent having the nucleobase sequence:
SEQ ID NO:1 TTG CTT CCA TCT TCC TCG TC.
A pyrrolidine phosphodiester linked oligomer of this preselected sequence is prepared using the T, A, C and G reagents from Examples 7, 11, 13 and 14, respectively, as per the procedure of Example 73 using iodine as the oxidation reagent to give the phosphodiester linked oligomeric compound having the "Aforvirsen" sequence.

EXAMPLE 75

Synthesis of Sequence Specific Pyrrolidine Oligomer Having Phosphorothioate Linkages A pyrrolidine phosphorothioate-linked oligomer of sequence SEQ ID NO:1 TTG CTT CCA TCT TCC TCG TC is prepared using the T, A, C and G reagents from Examples 7, 11, 13 and 14, respectively, as per the procedure of Example 73 using 3H-1,2-benzodithiole-3-one 1,1-dioxide as the oxidation reagent to give the phosphorothioate linked oligomeric compound.

EXAMPLE 76

Preparation of N-(2-[1-Tyrosinyl]-acetyl)-2-hydroxymethylpyrrolidine-4-morpholinophosphoramidate-thymidine-phosphodiester-thymidine Trimer A controlled pore glass resin derivatized with a 3'-5' phosphodiester linked dimer of thymidine (5'-DMT-O-T-O-

P(=O)—O—T-CPG] was synthesized in a standard manner. Two aliquots of this resin (each 24.6 mg, 47.5 mmole/g resin) were separately detritylated using 3% trichloroacetic acid in dichloromethane and then sequentially washed with anhydrous acetonitrile and pyridine. Each was vigorously agitated with 1 mL of a solution of the N-(2-[1-Tyrosinyl] acetyl)-2-O-dimethoxytrityloxymethyl-pyrrolidine-3-H-phosphonate monomer (25 mM) in adamantoyl chloride (50 mM) and pyridine for five minutes. The resins were then washed repeatedly with anhydrous pyridine and blown dry with argon gas. To one column was added 1 mL of iodine/pyridine/water (2/90/8) solution and agitated vigorously; to the second column was added 1 mL of morpholine/carbon tetrachloride/pyridine (1/5/5) solution and both were agitated for 30 minutes. The columns were subsequently washed with pyridine and acetonitrile and then blown dry with argon gas. Products were cleaved from the CPG by treatment with 1 mL of concentrated ammonium hydroxide for 30 minutes. The ammonia solutions were evaporated to dryness and then treated with 80% acetic acid in water for 30 minutes to remove the trityl group An aliquot of the solution from the first column exhibited a single peak in an HPLC analysis (27.8 min, Vyadec C-18, 260 nm, linear gradient of ammonium acetate (pH 7)-acetonitrile, 0–75% acetonitrile in 52 minutes) corresponding to the phosphodiester trimer. A similar analysis yielded a pair of HPLC peaks (39.7 and 39.9 min) corresponding to the phosphoramidate diastereomeric trimers.

In a parallel set of experiments using the HPP-Tyrosine H-phosphonate monomer and the 5'-DMT-O-T-O—P(=O)—O-T-CPG, the coupled resins were oxidized to the phosphodiester trimer or to the phosphoramidate trimer using dimethylamine/carbon tetrachloride. These experiments yielded the phosphodiester trimer and the unresolved dimethylamine phosphoramidate trimers at 12.4 min by an HPLC analysis, under the conditions described before.

EXAMPLE 77

(5R)-O-(t-Butyldimethylsilyl)-(3R)-Hydroxypiperidine

N-Benzyl-(5R)-O-(t-butyldimethylsilyl)-(3R)-hydroxypiperidine (J. Cossy, C. Dumas, P. Michel, D. Gomez Pardo, *Tetrahedron Lett.*, 1995, 36, 549) is dissolved in ethanol synthesized according to the synthetic scheme set forth by Cossy et al. (Tetrahedron Lett., 1995, 36, 549). As set forth in Cossy et al., N-Benzyl-(5R)-O-(t-butyldimethylsilyl)-(3R)-hydroxypiperidine is prepared as follows.

Compound 15 was synthesized from (4R)-hydroxy-L-proline 14 in three steps.

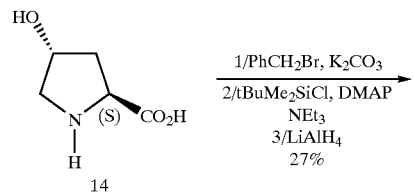

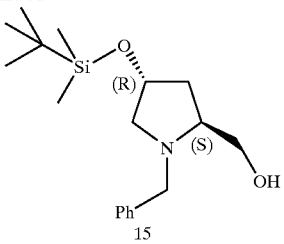

The ring expanded product 17 was obtained with a yield of 89%. After deprotection of the alcohol at C-5 the $\alpha_D$ was equal to +151° (c=0.5, ethanol).

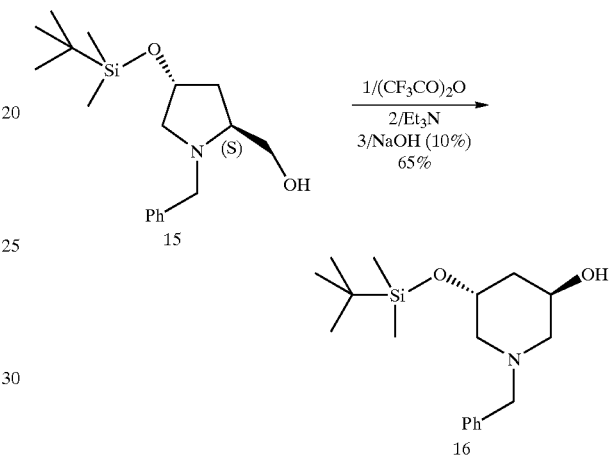

molecule was optically active, a C-2 axis of symmetry was present in the molecule and proved that the absolute configuration at C-3 was (R).

The first step of this ring expansion is probably the esterification of the alcohol by the trifluoroacetic anhydride and the formation of a quaternary ammonium salt. Without any triethylamine, no rearrangement is observed. When the triethylamine is added, an azidirinium ion is probably formed and the attack of the trifluoroacetate anion takes place either intra- or intermolecularly. A catalytic amount of 10% Pd/C is added, and the solution shaken under 3 ATM $H_2$. Once the starting material is consumed, the catalyst is filtered and the solvent removed under reduced pressure. The product is used without further purification.

EXAMPLE 78

N-(FMOC)-(5R)-O-(t-Butyldimethylsilyl)-(3R)-Hydroxypiperidine (5R)-O-(t-butyldimethylsilyl)-3R)-hydroxypiperidine and $Na_2CO_3$ (1.3 eq) are suspended in $H_2O$/Dioxane (1:1) (0.1M). Fluorenylmethyl chloroformate (1.1 eq) in toluene is added dropwise. The temperature of the reaction is not allowed to rise above 25° C. during the addition. The mixture is stirred vigorously overnight, acidified to pH 3 with concentrated HCl, and extracted twice with ethyl acetate. The organic extract is washed with brine. The solution is dried with $MgSO_4$, filtered and the solvent removed in vacuo. The product is purified by silica gel flash column chromatography.

EXAMPLE 79

N-(FMOC)-(3R)-O-Dimethoxytrityl-(5R)-O-(t-Butyldimethylsilyl)-Piperidine

N-(FMOC)-(5R)-O-(t-butyldimethylsilyl)-(3R)-hydroxypiperidine is coevaporated with dry pyridine, and

EXAMPLE 80

N-(FMOC)-(3R)-O-Dimethoxytrityl-(5R)-Hydroxypiperidine

N-(FMOC)-(3R)-O-dimethoxytrityl-(5R)-O-(t-butyldimethylsilyl)-Piperidine is dissolved in THF (0.1M), and added to a solution of tetrabutylammonium fluoride (3 eq) and acetic acid (9 eq)in THF. The solution is stirred until the starting material is consumed. The reaction is quenched with $NaHCO_3$, extracted with diethyl ether, washed with $NaHCO_3$, brine and dried with $MgSO_4$.

EXAMPLE 81

N-(FMOC)-(3R)-O-Dimethoxytrityl-Piperidine-(5R)-O-Hydrogen Phosphonate Triethylammonium salt The title compound is prepared from N-(FMOC)-(3R)-O-dimethoxytrityl-(5R)-hydroxypiperidine using the general procedure of Example 59.

EXAMPLE 82

N-(FMOC)-(3R)-O-Dimethoxytrityl-Piperidine-(5R)-O-Succinate

The title compound is prepared from N-(FMOC)-(3R)-O-dimethoxytrityl-(5R)-hydroxypiperidine using the general procedure of Example 60.

EXAMPLE 83

N-(FMOC)-(3R)-O-Dimethoxytrityl-Piperidine-(5R)-O-Succinyl-CPG

The title compound is prepared from N-(FMOC)-(3R)-O-dimethoxytrityl-piperidine-(5R)-O-succinate using the general procedure of Example 61.

EXAMPLE 84

(2S)-Carboxyethyl-Pyrrolidine-5-carboxylic acid-4-methylphenylthioester

The title compound is obtained as a mixture of epimers at C5 from N-BOC-Pyroglutamate ethyl ester using the method of J. Ezquerra, A., Rubio, C., Pedregal, G., Sanz, J. H., Rodriguez, J. L., Garcia R., *Tetrahedron Lett.* 1993, 34, 4989.

EXAMPLE 85

N-FMOC-(2S)-Carboxyethyl-Pyrrolidine-5-carboxylic acid-4-methylphenylthioester (2S)-Carboxyethyl-pyrrolidine-5-carboxylic acid-4-methylphenylthioester and $Na_2CO_3$ (1.3 eq) are suspended in $H_2O$/Dioxane (1:1) (0.1 M). Fluorenylmethyl chloroformate (1.1 eq) in toluene is added dropwise. The temperature of the reaction is not allowed to rise above 25° C. during the addition. The mixture is stirred vigorously overnight, acidified to pH 3 with concentrated HCl, and extracted twice with ethyl acetate. The organic extract is washed with brine. The solution is dried with $MgSO_4$, filtered and the solvent removed in vacuo. The product is purified by silica gel flash column chromatography.

EXAMPLE 86

N-FMOC-(2S)-Carboxyethyl-(5R)-Hydroxymethyl-Pyrrolidine and N-FMOC-(2S)-Carboxyethyl-(5S)-Hydroxymethyl-Pyrrolidine The mixture of thioesters from the Example 85 are dissolved in THF and treated with $Pd(OAc)_2$ and triethylsilane. Once the thioesters are reduced to the aldehyde, the solution is cooled to 0° C., and 1 eq $LiBH_4$ added. The reaction is stopped by the addition of acetic acid. The solvent is removed, and the residue extracted with ethyl acetate, washed with 5% NaHCO3, brine and dried with MgSO4. The products (epimers) are separated by silica gel flash column chromatography.

EXAMPLE 87

N-FMOC-(2S)-Carboxyethyl-(5R)-Dimethoxytrityloxymethyl-Pyrrolidine

N-FMOC-(2S)-carboxyethyl-(5R)-hydroxymethyl-pyrrolidine is coevaporated with dry pyridine, and redissolved in dry pyridine (0.1M). Dimethoxytrityl chloride (1.2 eq) is added in portions over 15 minutes, and the solution stirred at RT overnight. Methanol is then added (10 ml), and the solvent removed under reduced pressure. The resulting gum is redissolved in ethyl acetate, washed with 0.1 M citric acid, $NaHCO_3$, brine, dried with $MgSO_4$, and evaporated. The residue is purified by silica gel flash column chromatography.

EXAMPLE 88

N-FMOC-(2S)-Hydroxymethyl-(5R)-Dimethoxytrityloxymethyl-Pyrrolidine

N-FMOC-(2S)-carboxyethyl-(5R)-dimethoxytrityloxymethyl-pyrrolidine is dissolved in dry THF, cooled to 0° C., and 2 eq LiBH4 is added. The solution is warmed to room temperature until the starting material is consumed. The reaction is quenched with ethyl acetate, and washed with 0.1 M citric acid, $NaHCO_3$, brine, dried with $MgSO_4$ and evaporated. The product is purified by silica gel flash column chromatography.

EXAMPLE 89

N-FMOC-(5R)-Dimethoxytrityloxmethyl-Pyrrolidine-(2S)-oxymethyl-Hydrogen Phosphonate Triethylammonium salt The title product is prepared from N-FMOC-(2S)-Hydroxymethyl-(5R)-Dimethoxytrityloxymethyl-Pyrrolidine using the general procedure of Example 59.

EXAMPLE 90

N-FMOC-(5R)-Dimethoxytrityloxymethyl-Pyrrolidine-(2S)-Oxymethyl Succinate

The title product is prepared from N-FMOC-(2S)-Hydroxymethyl-(5R)-Dimethoxytrityloxymethyl-Pyrrolidine using the general procedure of Example 60.

EXAMPLE 91

N-FMOC-(5R)-Dimethoxytrityloxymethyl-
Pyrrolidine-(2S)-oxymethyl-Succinyl-CPG

The title product is prepared from N-FMOC-(5R)-dimethoxytrityloxymethyl-pyrrolidine-(2S)-Oxymethyl Succinate using the general procedure of Example 61.

EXAMPLE 92

N-FMOC-(2S)-Carboxyethyl-(5S)-
Dimethoxytrityloxymethyl-Pyrrolidine

N-FMOC-(2S)-Carboxyethyl-(5S)-Hydroxymethyl-Pyrrolidine is coevaporated with dry pyridine, and redissolved in dry pyridine (0.1M). Dimethoxytrityl chloride (1.2 eq) is added in portions over 15 minutes and the solution is stirred at RT overnight. Methanol (10 ml) is then added and the solvent removed under reduced pressure. The resulting gum is redissolved in ethyl acetate, washed with 0.1 M citric acid, concentrated $NaHCO_3$ solution, brine, dried with $MgSO_4$, and evaporated. The residue is purified by silica gel flash column chromatography.

EXAMPLE 93

N-FMOC-(2S)-Hydroxymethyl-(5S)-
Dimethoxytrityloxymethyl-Pyrrolidine

N-FMOC-(2S)-carboxyethyl-(5S)-dimethoxytrityloxymethyl-pyrrolidine is dissolved in dry THF, cooled to 0° C., and 2 eq $LiBH_4$ is added. The solution is warmed to room temperature until the starting material is consumed. The reaction is quenched with ethyl acetate, and washed with 0.1 M citric acid, concentrated $NaHCO_3$ solution, brine, dried with $MgSO_4$ and evaporated. The product is purified by silica gel flash column chromatography.

EXAMPLE 94

N-FMOC-(5S)-Dimethoxytrityloxymethyl-
Pyrrolidine-(2S)-oxymethyl-Hydrogen Phosphonate
Triethylammonium salt The title product is prepared from N-FMOC-(2S)-hydroxymethyl-(5S)-dimethoxytrityloxymethyl-pyrrolidine using the general procedure of Example 59.

EXAMPLE 95

N-FMOC-(5S)-Dimethoxytrityloxymethyl-
Pyrrolidine-(2S)-Oxymethyl Succinate

The title product is prepared from N-FMOC-(2S)-Hydroxymethyl-(5S)-Dimethoxytrityloxymethyl-Pyrrolidine fusing the general procedure of Example 60.

EXAMPLE 96

N-FMOC-(5S)-Dimethoxytrityloxymethyl-
Pyrrolidine-(2S)-Oxymethyl-Succinyl-CPG

The title product is prepared from N-FMOC-(5S)-Dimethoxytrityloxymethyl-Pyrrolidine-(2S)-Oxymethyl Succinate using the general procedure of Example 61.

EXAMPLE 97

N-FMOC-2,2'-Dihydroxyethylamine

Diethanolamine and $Na_2CO_3$ (1.3 eq) are suspended in $H_2O$/Dioxane (1:1) (0.1M). Fluorenylmethyl chloroformate (1.1 eq) in toluene is added dropwise. The temperature of the reaction is not allowed to rise above 25° C. during the addition. The mixture is stirred vigorously overnight, acidified to pH 3 with concentrated HCl, and extracted twice with ethyl acetate. The organic extract is washed with brine, dried with $MgSO_4$, filtered and the solvent removed in vacuo. The product is purified by silica gel flash column chromatography.

EXAMPLE 98

N-FMOC-2'-Hydroxyethyl-2-O-
Dimethoxytritylethylamine

N-FMOC-2,2'-dihydroxyethylamine is coevaporated with dry pyridine, and redissolved in dry pyridine (0.1 M). Dimethoxytrityl chloride (1.2 eq) is added in portions over 15 minutes, and the solution stirred at RT overnight. Methanol (10 ml) is then added and the solvent removed under reduced pressure. The resulting gum is redissolved in ethyl acetate, washed with 0.1 M citric acid, concentrated $NaHCO_3$, solution, brine, dried with $MgSO_4$, and evaporated. The residue is purified by silica gel flash column chromatography.

EXAMPLE 99

N-FMOC-2-O-Dimethoxytritylethylamino-2'-O-
Ethyl Hydrogen Phosphonate Triethylammonium
salt The title product is prepared from N-FMOC-2'-Hydroxyethyl-2-O-Dimethoxytritylethylamine using the general procedure of Example 59.

EXAMPLE 100

N-FMOC-2,3-Propanediol

1-Aminopropanediol and $Na_2CO_3$ (1.3 eq) are suspended in $H_2O$/Dioxane (1:1) (0.1 M). Fluorenylmethyl chloroformate (1.1 eq) in toluene is added dropwise. The temperature of the reaction is not allowed to rise above 25° C. during the addition. The mixture is stirred vigorously overnight, acidified to pH 3 with concentrated HCl, and extracted twice with ethyl acetate. The organic extract is washed with brine, dried with $MgSO_4$, filtered and the solvent removed in vacuo. The product is purified by silica gel flash column chromatography.

EXAMPLE 101

N-FMOC-2-Hydroxy-3-O-Dimethoxytrityl-Propane

N-FMOC-2,3-Propanediol is coevaporated with dry pyridine, and redissolved in dry pyridine (0.1 M). Dimethoxytrityl chloride (1.2 eq) is added in portions over 15 minutes and the solution stirred at RT overnight. Methanol (10 ml)is then added and the solvent removed under reduced pressure. The resulting gum is redissolved in ethyl acetate, washed with 0.1 M citric acid, concentrated $NaHCO_3$ solution, brine, dried with $MgSO_4$, and evaporated. The residue is purified by silica gel flash column chromatography.

EXAMPLE 102

Derivatization of Backbone Segment Amino
Combinatorial Site to Form Ureas General
Procedure To the free amine on solid support is added a solution of carbonyl diimidazole (0.1 mmol/ml) in DMF. A tenfold excess of reagent is added at the 10 umol scale level. The reaction is allowed to proceed for 30 min, and the reagent removed with DMF. A solution of the desired amine in DMF (10% v/v) is then added. After 30 minutes the solid support is washed with DMF until all the reagents are removed to give the urea derivatized backbone segment amino combinatorial site.

EXAMPLE 103

N-Fmoc-3,4-Trans-Dicarboxymethylpyrrolidine

Dimethylfumarate (38.7 g, 268 mmol) was dissolved in 1 l $CH_2Cl_2$, and trifluoroacetic acid added (3 ml, 40 mmol). The Azomethine ylide precursor N-Benzyl-N-Methoxymethyl-N-(Trimethylsilylmethyl)-amine was added dropwise with stirring (60.4 g, 255 mmol). The solution was stirred overnight at RT. The solvent was removed and the crude product was redissolved in 1.5 l methanol. 300 ml 1 N HCl was added, the solution degassed with Ar, and 10 g 10% Pd/C added. $H_2$ was bubbled through then the solution stirred under a $H_2$ balloon until the material was consumed (24 hr). The catalyst was filtered, the solvent removed and the residue redissolved in 500 ml $H_2O$ and 500 ml dioxane to which was added 32 g (300 mmol) $Na_2CO_3$. A solution of Fmoc-Cl (66 g, 255 mmol) in 500 ml dioxane was added dropwise. The solution was stirred 16 h, acidified to pH 3 and the solvent evaporated. The residue was extracted with EtOAc, washed with water, brine dried with $MgSO_4$ and evaporated. 92 g title product was obtained.

EXAMPLE 104

N-Fmoc-3,4-Trans-Dihydroxymethylpyrrolidine

N-Fmoc-3,4-Trans-Dicarboxymethylpyrrolidine (92 g, 225 mmol) was dissolved in 1000 ml THF, and 250 ml $LiBH_4$ (2M in THF, Aldrich) was added with cooling (exothermic). The solution was stirred at RT 2 hrs and carefully quenched with 50% HCl to pH 2. The solvent was evaporated. The residue was extracted with EtOAc (2×500 ml), washed with $NaHCO_3$, brine, and dried with $MgSO_4$ and evaporated. 78.6 g crude product was obtained (100%). The product was recrystallized from 300 ml acetonitrile to give 60 g

EXAMPLE 105

N-Fmoc-3-Dimethoxytrityloxymethyl-4-hydroxymethylpyrrolidine

N-Fmoc-3,4-Trans-Dihydroxymethylpyrrolidine was dissolved in $CH_2Cl_2$ and pyridine (9:1), cooled to 0° C. and DMT-Cl added in portions (1.0 eq). The solution was stirred overnight at 0° C. The reaction was quenched with MeOH, evaporated and excess solvent removed by azeotropic distillation with toluene. The product was redissolved in EtOAc, washed with 5% citric acid, $NaHCO_3$, brine and dried with $MgSO_4$. Purification was achieved by silica gel flash column chromatography, using a gradient of from 0 to 3% methanol, in $CH_2Cl_2$. The product was obtained in 50% yield, along with 25% ditritylated material which is conserved and recycled, and 25% unreacted starting material.

EXAMPLE 106

N-FMOC-trans-3-(oxymethyl)-4-(Dimethoxytrityloxymethyl)-Pyrrolidine Hydrogen Phosphonate Triethylammonium salt The title product is prepared from N-Fmoc-3-Dimethoxytrityloxymethyl-4-hydroxymethylpyrrolidine using the general procedure of Example 59.

EXAMPLE 107

N-FMOC-trans-3-(oxymethyl)-4-(Dimethoxytrityloxymethyl)-Pyrrolidine Succinate

The title product is prepared from N-FMOC-trans-3-(Hydroxymethyl)-4-(Dimethoxytrityloxymethyl)-Pyrrolidine using the general procedure of Example 60.

EXAMPLE 108

N-FMOC-trans-3-(oxymethyl)-4-(Dimethoxytrityloxymethyl)-Pyrrolidine Succinyl CPG The title product is prepared from N-FMOC-trans-3-(Hydroxymethyl)-4-(Dimethoxytrityloxymethyl)-Pyrrolidine using the general procedure of Example 61.

EXAMPLE 109

N-CBZ-cis-4-Amino-2-cyclopenten-1-ol

The product is prepared by the method of A. R. Ritter, M. J. Miller, Tetrahedron Lett. 1994, 35, 9379.

EXAMPLE 110

N-CBZ-cis-4-Amino-2,3-oxocyclopentan-1-ol

N-CBZ-cis-4-Amino-2-cyclopenten-1-ol is dissolved in dichloromethane and meta chloroperbenzoic acid is added. The solution is stirred until the starting material disappears. The reaction is quenched by the addition of a 5% solution of sodium bisulfite, extracted with dichloromethane, washed with $NaHCO_3$, brine and dried. The title compound is purified by silica gel flash column chromatography.

EXAMPLE 111

N-CBZ-cis-4-Aminocyclopentan-1,2-diol

The epoxide of Example 110 is dissolved in THF, and treated with 2 eq $LiBH_4$ in the presence of a catalytic amount of $Ti(OiPr)_4$. Stirring is continued until the reaction is complete. The reaction is diluted with ethyl acetate, washed with 0.1 M citric acid, $NaHCO_3$, brine, dried with $MgSO_4$ and evaporated. The title compound is purified by silica gel flash column chromatography.

EXAMPLE 112

N-CBZ-cis-4-Amino-2-O-dimethoxytritylcyclopentan-1-ol

N-CBZ-cis-4-Aminocyclopentan-1,2-diol is coevaporated with dry pyridine, and redissolved in dry pyridine (0.1 M). Dimethoxytrityl chloride (1.0 eq) is added in portions over 15 minutes and the solution stirred at RT overnight. Methanol is then added (10 ml), and the solvent removed under reduced pressure. The resulting gum is redissolved in ethyl acetate, washed with 0.1 M citric acid, $NaHCO_3$, brine, dried with $MgSO_4$, and evaporated. The title compound is purified by silica gel flash column chromatography.

EXAMPLE 113

N-FMOC-cis-4-Amino-2-O-dimethoxytritylcyclopentan-1-ol

N-CBZ-cis-4-Amino-2-O-dimethoxytritylcyclopentan-1-ol is dissolved in ethanol and 10% Pd/C is added. The mixture is shaken under 1 ATM H$_2$ until all the material is consumed. The catalyst is filtered, the solvent removed. The residue and Na$_2$CO$_3$ (1.3 eq) are suspended in H$_2$O/Dioxane (1:1) (0.1 M). Fluorenylmethyl chloroformate (1.1 eq) in toluene is added dropwise. The temperature of the reaction is not allowed to rise above 25° C. during the addition. The mixture is stirred vigorously overnight, acidified to pH 3 with concentrated HCl, and extracted twice with ethyl acetate. The organic extract is washed with brine, dried with MgSO$_4$, filtered and the solvent removed in vacuo. The title compound is purified by silica gel flash column chromatography.

EXAMPLE 114

N-FMOC-cis-4-Amino-2-O-dimethoxytritylcyclopentan-1-O-Hydrogen Phosphonate triethylammonium salt The title compound is prepared using the general procedure of Example 59.

EXAMPLE 115

N-CBZ-cis-4-Amino-2-cyclohexen-1-ol

The product is prepared by the method of A. R. Ritter, M. J. Miller, J. Org. Chem. 1994, 59, 4602.

EXAMPLE 116

N-CBZ-cis-4-Amino-2,3-oxocyclohexan-1-ol

N-CBZ-cis-4-Amino-2-cyclohexen-1-ol is dissolved in dichloromethane and meta chloroperbenzoic acid is added. The solution is stirred until the starting material disappears. The reaction is quenched by the addition of a 5% solution of sodium bisulfite, extracted with dichloromethane, washed with NaHCO$_3$, brine and dried. The title compound is purified by silica gel flash column chromatography.

EXAMPLE 117

N-CBZ-cis-4-Aminocyclohexan-1,2-diol

The epoxide of the previous example is dissolved in THF, and treated with 2 eq LiBH$_4$ in the presence of a catalytic amount of Ti(OiPr)$_4$. Stirring is continued until the reaction is complete. The reaction is diluted with ethyl acetate, washed with 0.1M citric acid, NaHCO3, brine, dried with MgSO$_4$ and evaporated. The title compound is purified by silica gel flash column chromatography.

EXAMPLE 118

N-CBZ-cis-4-Amino-2-O-dimethoxytritylcyclohexan-1-ol

N-CBZ-cis-4-aminocyclohexan-1,2-diol is coevaporated with dry pyridine, and redissolved in dry pyridine (0.1 M). Dimethoxytrityl chloride (1.0 eq) is added in portions over 15 min, and the solution stirred at RT overnight. Methanol is then added (10 ml), and the solvent removed under reduced pressure. The resulting gum is redissolved in ethyl acetate, washed with 0.1 M citric acid, NaHCO$_3$, brine, dried with MgSO$_4$, and evaporated. The title compound is purified by silica gel flash column chromatography.

EXAMPLE 119

N-FMOC-cis-4-Amino-2-O-dimethoxytritylcyclohexan-1-ol

N-CBZ-cis-4-Amino-2-O-dimethoxytritylcyclohexan-1-ol is dissolved in ethanol and 10% Pd/C is added. The mixture is shaken under 1 ATM H$_2$ until all the material is consumed. The catalyst is filtered, the solvent removed. The residue and Na$_2$CO$_3$ (1.3 eq) are suspended in H$_2$O/Dioxane (1:1) (0.1 M). Fluorenylmethyl chloroformate (1.1 eq) in toluene is added dropwise. The temperature of the reaction is not allowed to rise above 25° C. during the addition. The mixture is stirred vigorously overnight, acidified to pH 3 with concentrated HCl, and extracted twice with ethyl acetate. The organic extract is washed with brine, dried with MgSO$_4$, filtered and the solvent removed in vacua. The title compound is purified by silica gel flash column chromatography.

EXAMPLE 120

N-FMOC-cis-4-Amino-2-O-dimethoxytritylcyclohexan-1-O-Hydrogen Phosphonate triethylammonium salt The title compound is prepared using the general procedure of Example 59.

EXAMPLE 121

Synthesis of a 4-mer Having Backbone Segment Amino Combinatorial Backbone Segment Amino Combinatorial Sites Combinatorialized with the aldehydes benzaldehyde, Aldrich-B133-4; m-tolualdehyde, Aldrich-T3,550-5; m-anisaldehyde, Aldrich-12,965-8; and 3-nitrobenzaldehyde, Aldrich-N1,084-5

Method 1: Bead Splitting

A solid support is derivatized with 2-O-(dimethoxytrityl) ethylsuccinate half ester as in Example 26. The DMT protecting group is removed using the standard method of Example 64. 4-O-Dimethoxytrityl-2-N-Fmoc-aminobutan-1-ol is treated with PCl$_3$ as per Example 28 to form the phosphonic acid which is condensed onto the derivatized resin as in Example 38. The Fmoc amino protecting group is removed as per Example 4 and the solid support is divided into 4 equal portions and each portion is reacted with one of benzaldehyde, m-tolualdehyde, m-anisaldehyde, or 3-nitrobenzaldehyde to effect coupling to the resulting free amino as per the method of Example 66 and the method of Look, G. C., et al., *Tetrahedron Lett.*, 1995, 36, 2937–2940, and the portions of solid support recombined. The combined solid support is treated with a solution of NaCNBH$_3$ or LiBH$_4$ in tetrahydrofuran for 30 minutes followed by washing of the solid support by methanol. The above methods are repeated until four aminodiol monomer subunits are incorporated having an equal molar mixture of each aldehyde letter at each of the amino sites. The resulting four mer is treated using the procedures of Example 67, with a large excess of benzylamine in carbon tetrachloride/pyridine. The solid support is shaken for 15 minutes and the supernatant is removed by filtration and then washed with pyridine. A second treatment with a large excess of benzylamine in carbon tetrachloride/pyridine followed by shaking will insure efficient oxidation to the phosphoramidate. The resin is washed with pyridine/acetonitrile and then the phosphoramidate is cleaved from the resin by a treatment with concentrated ammonium hydroxide at room temperature for 3 hours. Evaporation of the supernatant and purification of the phosphoramidate on an RP-18 HPLC column will yield the final oligomer.

Method 2

A solid support is derivatized with 2-O-(dimethoxytrityl) ethylsuccinate half ester as in Example 26. The DMT protecting group is removed using the standard method of Example 64. 4-O-Dimethoxytrityl-2-N-Fmoc-aminobutan-1-ol is treated with $PCl_3$ as per Example 28 to form the phosphonic acid which is condensed onto the derivatized resin as in Example 38. Following this procedure the four mer is synthesized in four iterations of the above. The Fmoc amino protecting groups are removed as per Example 4 and is reacted concurrently, in one pot, with benzaldehyde, m-tolualdehyde, m-anisaldehyde, and 3-nitrobenzaldehyde. To effect this concurrent reaction 50 µmol of oligomeric compound attached to solid support is reacted with 50 µmol benzaldehyde, 50 µmol m-tolualdehyde, 50 µmol m-anisaldehyde, and 50 µmol 3-nitrobenzaldehyde in triethyl orthoformate. The resulting imines are reduced as per the procedure of method 1 above. In this way the four amino combinatorial sites of each oligomeric compound attached to the solid support are combinatorialized utilizing a competitive mechanism involving a mixture of aldehydes. The resulting four mer is treated using the procedures of Example 67, with a large excess of benzylamine in carbon tetrachloride/pyridine. The solid support is shaken for 15 minutes and the supernatant is removed by filtration and then washed with pyridine. A second treatment with a large excess of benzylamine in carbon tetrachloride/ pyridine followed by shaking will insure efficient oxidation to the phosphoramidate. The resin is washed with pyridine/acetonitrile and then the phosphoramidate is cleaved from the resin by a treatment with concentrated ammonium hydroxide at room temperature for 3 hours. Evaporation of the supernatant and purification of the phosphoramidate on an RP-18 HPLC column will yield the final oligomer.

EXAMPLE 122

Synthesis of Combinatorial Libraries Using Various Selected Aldehydes

Using the procedure of example 121 libraries are prepared from oligomeric compounds of the invention that are derivatized with one, two, three, four or more of the following aldehydes available from Aldrich Chemical Company, Inc., Milwaukee, Wis. The Aldrich catalog number is given in the right hand column and the compound name is given in the left hand column:

Aromatic Aldehydes 10793-5 Phenylacetaldehyde
D20425 Diphenylacetaldehyde
24582-8 Hydrocinnamaldehyde
24136-9 Phenylpropionaldehyde
28902-7 (+/−)-3-Phenylbutyraldehyde
28899-3 Alpha-amylcinnamaldehyde
16116-0 Alpha-bromocinnamaldehyde
26813-5 4-Stilbenecarboxaldehyde
B133-4 Benzaldehyde
11755-2 o-Tolualdehyde
25069-4 Alpha.alpha.alpha-trifluoro-o-tolualdehyde
F480-7 2-Fluorobenzaldehyde
12497-4 2-Chlorobenzaldehyde
B5700-1 2-Bromobenzaldehyde
10962-2 o-Anisaldehyde
15372-9 2-Ethoxybenzaldehyde
N1080-2 2-Nitrobenzaldehyde
T3550-5 m-Tolualdehyde
19687-8 Alpha.alpha.alpha-trifluoro-m-tolualdehyde
F500-5 3-Fluorobenzaldehyde
C2340-3 3-Chlorobenzaldehyde
B5720-6 3-Chlorobenzaldehyde
12965-8 m-Anisaldehyde
34648-9 3-(Trifluoromethoxy)-benzaldehyde
34199-1 3-(1,1,2,2-Tetrafluoroethoxy)-benzaldehyde
H1980-8 3-Hydroxybenzaldehyde
N1084-5 3-Nitrobenzaldehyde
11528-2 Isophthaldehyde
T3560-2 p-Tolualdehyde
23363-3 4-Ethylbenzaldehyde
13517-8 4-Isopropylbenzaldehyde
22494-4 Alpha.alpha.alpha-trifluoro-p-tolualdehyde
12837-6 4-Fluorobenzaldehyde
11221-6 4-Chlorobenzaldehyde
B5740-0 4-Bromobenzaldehyde
A8810-7 p-Anisaldehyde
17360-6 4-Ethoxybenzaldehyde
33363-8 4-Propoxybenzaldehyde
23808-2 4-Butoxybenzaldehyde
37060-6 4-(Trifluoromethoxy)-benzaldehyde
27486-0 Terephthaldehyde mono-(diethyl acetal)
14408-8 4-Hydroxybenzaldehyde
22277-1 4-(Methylthio)benzaldehyde
10976-2 4-(Dimethylamino)benzaldehyde
D8625-6 4-(Dimethylamino)benzaldehyde
33851-6 4-(Dibutylamino)benzaldehyde
29355-5 4-(3-Dimethylaminopropoxy)benzaldehyde
13017-6 4-Nitrobenzaldehyde
T220-7 Terephthaldicarboxaldehyde
34252-1 3-Fluoro-2-methylbenzaldehyde
34649-7 2-Fluoro-3-(trifluoromethyl)-benzaldehyde
26514-4 2,3-Difluorobenzaldehyde
26515-2 2,6-Difluorobenzaldehyde
14124-0 2-Chloro-6-fluorobenzaldehyde
D5650-0 2,6-Dichlorobenzaldehyde
25483-5 2,3-Dichlorobenzaldehyde
D13020-6 2,3-Dimethoxybenzaldehyde
29250-8 2,6-Dimethoxybenzaldehyde
31980-5 3-Fluorosalicylaldehyde
12080-4 o-Vanillin
18983-9 2,3-Dihydroxybenzaldehyde
10604-6 2-Chloro-6-nitrobenzaldehyde
16382-1 3-methoxy-2-nitrobenzaldehyde
11750-1 2,6-Dinitrobenzaldehyde
15104-1 2,4-Dimethylbenzaldehyde
15106-8 2,5-Dimethylbenzaldehyde
37682-5 2-Chloro-5-(trifluoromethyl)benzaldehyde
26516-0 3,4-Difluorobenzaldehyde
26517-9 2,4-Difluorobenzaldehyde
26518-7 2,5-Difluorobenzaldehyde
30600-2 3-Chloro-4-fluorobenzaldehyde
34807-4 2-Chloro-4-fluorobenzaldehyde
33954-7 3-Bromo-3-fluorobenzaldehyde
D5660-8 3,4-Dichlorobenzaldehyde
14675-7 2,4-Dichlorobenzaldehyde 15212-9 3-Methyl-p-anisaldehyde
15558-6 3-Fluoro-p-anisaldehyde
15429-6 5-Bromo-o-anisaldehyde
D13040-0 2,4-Dimethoxybenzaldehyde
D13060-5 2,5-Dimethoxybenzaldehyde
14375-8 3,4-Dimethoxybenzaldehyde
25275-1 3-Ethoxy-4-methoxybenzaldehyde
P4910-4 Piperonal
26459-8 1,4-Benzodioxan-6-carboxaldehyde
31691-1 4-Hydroxy-3-methylbenzaldehyde
34606-3 2-Chloro-4-hydroxybenzaldehyde
25975-6 5-Chlorosalicylaldehyde
13728-6 5-Bromosalicylaldehyde
14686-2 2-Hydroxy-5-methoxybenzaldehyde
16069-5 2-Hydroxy-4-methoxybenzaldehyde
14368-5 3-Hydroxy-4-methoxybenzaldehyde
V110-4 Vanillin
12809-0 3-Ethoxy-4-hydroxybenzaldehyde
34215-7 5-(Trifluoromethoxy)salicylaldehyde
D10840-5 3,4-Dihydroxybenzaldehyde
D10820-0 2,5-Dihydroxybenzaldehyde
16863-7 2,4-Dihydroxybenzaldehyde
22568-1 4-(Diethylamino)salicylaldehyde
C5880-0 5-Chloro-2-nitrobenzaldehyde
13903-3 2-Chloro-5-nitrobenzaldehyde
C5870-3 4-Chloro-3-nitrobenzaldehyde
14432-0 4-Hydroxy-3-nitrobenzaldehyde
15616-7 3-Hydroxy-4-nitrobenzaldehyde
27535-2 2-Hydroxy-5-nitrobenzaldehyde
H4810-7 5-Hydroxy-2-nitrobenzaldehyde
D19360-7 2,4-Nitrobenzaldehyde
29013-0 3,5-Bis(trifluoromethyl)benzaldehyde
29017-3 3,5-Difluorobenzaldehyde
13940-8 3,5-Dichlorobenzaldehyde
36811-3 3,5-Dihydroxybenzaldehyde
12269-2 3,5-Dimethoxybenzaldehyde
36810-5 3,5-Dibenzyloxybenzaldehyde
M680-8 Mesitaldehyde
29233-8 2,3,5-Trichlorobenzaldehyde
13061-3 5-Bromoveratraldehyde
13871-1 2,4,6-Trimethoxybenzaldehyde
T6840-3 3,4,5-Trimethoxybenzaldehyde
14039-2 3,5-Dimethyl-4-hydroxybenzaldehyde
35768-5 2,6-Dimethyl-4-hydroxybenzaldehyde
14040-6 3,5-Di-tert-butyl-4-hydroxybenzaldehyde hemihydrate
26181-5 3,5-Dichlorosalicylaldehyde
12213-0 3,5-Dibromosalicylaldehyde
28344-4 3,5-Diiodosalicylaldehyde
13060-5 5-Bromovanillin
12948-8 5-Iodovanillin
13879-7 4,6-Dimethoxysalicylaldehyde
25871-7 5-Nitrovanillin
S760-2 3,5-Dinitrosalicylaldehyde
25959-4 2,5-Dimethyl-p-anisaldehyde
T6540-4 5-Bromo-2,4-dimethoxybenzaldehyde
N2800-0 4-Nitrovanillin
27680-4 3,5-Dinitrosalicylaldehyde
15205-6 2,5-Dimethyl-p-anisaldehyde
29251-6 5-Bromo-2,4-dimethoxybenzaldehyde
15557-8 6-Bromoveratraldehyde
13215-2 2,4,5-Trimethoxybenzaldehyde
27960-9 6-Nitroveratraldehyde
13765-0 6-Nitropiperonal
27679-0 2,5-Dichloroterephthaldehyde
33066-3 2,3,4-Trifluorobenzaldehyde
29231-1 2,3,6-Trichlorobenzaldehyde
15201-3 2,3-Dimethyl-p-anisaldehyde
29627-9 2,4-Dimethoxy-3-methylbenzaldehyde
15209-9 2,3,4-Trimethoxybenzaldehyde
26084-3 2,3,4-Trihydroxybenzaldehyde
32893-6 Tetrafluorobenzaldehyde
10374-8 Pentafluorobenzaldehyde
B3468-0 4-Biphenylcarboxaldehyde
19175-2 3-Phenoxybenzaldehyde
B2700-5 3-Benzloxybenzaldehyde
19540-5 3-(4-Methylphenoxy)benzaldehyde
19592-8 3-(4-tert-Butylphenoxy)benzaldehyde
19539-1 3-[3-(Trifluoromethyl)phenoxy]benzaldehyde
19530-8 3-(4-Chlorophenoxy)benzaldehyde
19590-1 3-(3,4-Dichlorophenoxy)benzaldehyde
19774-2 3-(3,5-Dichlorophenoxy)benzaldehyde
19589-8 3-(4-Methoxyphonoxy)benzaldehyde
21126-5 4-Phenoxybenzaldehyde
12371-4 4-Benzyloxybenzaldehyde
16361-9 4-Benzyloxy-3-methoxybenzaldehyde
16395-3 3-Benzyloxy-4-methoxybenzaldehyde
34603-9 3-Methoxy-4-(4-nitrobenzyloxy)benzaldehyde
D3600-3 3,4-Dibenzyloxybenzaldehyde
N10-9 1-Naphthaldehyde
N20-6 2-Naphthaldehyde
15134-3 2-Methoxy-1-naphthaldehyde
10324-1 4-Methoxy-1-naphthaldehyde
H4535-3 2-Hydroxy-1-naphthaldehyde
27208-6 4-Dimethylamino-1-naphthaldehyde
38201-9 2,3-Naphthalendicarboxaldehyde
15014-2 2-Fluorenecarboxaldehyde
27868-8 9-Anthraldehyde
M2965-7 10-Methylanthracene-9-carboxaldehyde
15211-0 10-Chloro-9-anthraldehyde
P1160-3 Phenanthrene-9-carboxaldehyde
14403-7 1-Pyrenecarboxaldehyde
Aliphatic Aldehydes
25254-9 Formaldehylde
11007-8 Acetaldehyde
P5145-1 Propionaldehyde
24078-8 Isobutyraldehyde
T7150-1 Trimethylacetaldehyde
B10328-4 Butyraldehyde
M3347-6 2-Methylbutyraldehyde
11009-4 2-Ethylbutyraldehyde
14645-5 Isovaleraldehyde
35990-4 3,3-Dimethylbutyraldehyde
11013-2 Valeraldehyde 25856-3 2-Methylvaleraldehyde
D19050-0 2,4-Dimethylvaleraldehyde
11560-6 Hexanal
E2910-9 2-Ethylhexanal
30355-0 3,5,5-Trimethylhexanal
H212-0 Heptaldehyde
0560-8 Octyl aldehyde
N3080-3 Nonyl aldehyde
12577-6 Decyl aldehyde
U220-2 Undecylic aldehyde
M8675-8 2-Methylundecanal
D22200-3 Dodecyl aldehyde
26923-9 Tridecanal
T1000-6 Tetradecy aldehyde
11022-1 Acrolein
13303-5 Methacrolein
25614-5 2-Ethylacrolein
25613-7 2-Butylacrolein
13298-5 Crotonaldehyde
19261-9 trans-2-Methyl-2-butenal
29468-3 2-Ethyl-trans-2-butenal
30407-7 3-Methyl-2-butenal
26925-5 trans-2-pentenal
29466-7 2-Methyl-2-pentenal
29097-1 2,2-Dimethyl-4-pentenal
13265-9 trans-2-Hexenal
25176-3 trans-2-Heptenal
30796-3 2,6-Dimethyl-5-heptenal
26995-6 trans-2-Octenal
34364-1 (R)-(+)-Citronellal
37375-3 (S)-(−)-Citronellal
25565-3 trans-2-Nonenal
37562-4 cis-4-Decenal
36733-8 trans-4-Decenal
13227-6 Undecylenic aldehyde
24911-4 dis-9-hexadecenal
27221-3 Cyclopropanecarboxaldehyde
10846-4 Cyclohexanecarboxaldehyde
10933-9 Cyclooctanecarboxaldehyde
30441-7 3-Cyclohexylpropionaldehyde
T1220-3 Tetrahydrobenzaldehyde
21829-4 (S)-(−)-Perillaldehyde
26467-9 2,6,6-Trimethyl-1-cyclohexene-1-acetaldehyde
10937-1 5-Norbornen-2-carboxaldehyde
21824-3 (1R)-(−)-Myrtenal
37531-4 Glyoxal-1,1-dimethyl acetal
21877-4 7-Methoxy-3,7-dimethyloctanal
23254-8 3-Ethoxymethacrolein
27525-5 2,5-Dimethoxy-3-tetrahydrofurancarboxaldehyde
26918-2 2,2-Dimethyl-3-hydroxypropionaldehyde
G480-2 DL-Glyceraldehyde
G478-0 D-Glyceraldehyde
21665-8 L-Glyceraldehyde
34140-13-(methylthio)propianaldehyde.
30583-9 3-(Dimethylamino)acrolein
36549-9 3-(Dimethylamino)-2-methyl-2-propenal
17733-4 Pyrubic aldehyde
27706-1 (S)-(−)-2-(Methoxymethyl)-1-pyrrolidinecarboxaldehyde
29211-7 2-Methoxy-1-pyrrolidinecarboxaldehyde
29210-9 2-Methoxy-1-piperidinecarboxaldehyde

EXAMPLE 123

Synthesis of Libraries from Oligomeric Compounds Utilizing Aryl Acid Halides

Use of Benzoyl Chloride Aldrich; 3-methylbenzoyl chloride Aldrich-T3,550-5; 3-methoxybenzoyl chloride, Aldrich-12, 965-9; and 3-nitrobenzoyl Chloride Aldrich-N1,084-5, as Illustrative Letters Preparation of combinatorial libraries as per Example 121 using benzoic acids and benzoic acid derivatives is effected in place of benzyl aldehydes described above using the general procedure of Examples 63 and 65.

Using the above, libraries are prepared from oligomeric compounds that are derivatized with one, two, three, four, or more of the following acid halides available from Aldrich Chemical Company, Inc., Milwaukee, Wis. The Aldrich catalog number is given in the right hand column and the compound name in the left hand column:

10663-1 p-Toluoyl chloride
30253-8 3-Cyanobenzoyl chloride
13096-6 (+/−)-2-Cloro-2-phenylacetyl chloride
26366-4 3-(Chloromethyl)benzoyl chloride
27078-4 4-(Chloromethyl)benzoyl chloride
24947-5 4-(Trifluoromethyl)benzoyl chloride
19394-1 4-Chlorophenoxyacetyl chloride
24948-3 2-(Trifluoromethyl)benzoyl chloride
19394-1 4-Chlorophenoxyacetyl chloride
24948-3 2-(Trifluoromethyl)benzoyl chloride
10663-1 p-Toluoyl chloride
25027-9 3-(Trifluoromethyl)benzoyl chloride
S67828-7 2-(2,4,5-Trichlorophenoxy)acetyl chloride
12201-7 o-Toluoyl chloride
40248-6 4-(Trifluoromethoxy)benzoyl chloride
37502-0 3-(Dichloromethyl)benzoyl chloride
12225-4 m-Toluoyl chloride
12482-6 4-Cyanobenzoyl chloride
P1675-3 Phenylacetyl chloride
S88415-4 2-(Phenylthio)propionyl chloride
15862-3 Phenoxyacetyl chloride
36475-4 trans-4-Nitrocinnamoyl chloride
28882-9 4-Ethoxybenzoyl chloride
23024-3 m-Anisoyl chloride
S67595-4 2,3-Dibromo-3-phenylpropionyl chloride
30101-9 Benzyloxyacetyl chloride
25470-3 o-Anisoyl chloride
C8110-1 Cinnamoyl chloride
31693-8 3-Methoxyphenylacetyl chloride
A8847-6 p-Anisoyl chloride
16519-0 Acetylsalicyloyl chloride
36569-6 4-Methoxyphenylacetyl chloride
24944-0 Hydrocinnamoyl chloride
26528-4 3,5-Bis(trifluoromethyl)benzoyl chloride
28350-94 Ethylbenzoyl chloride
S40503-5 2-Phenoxypropionyl chloride 33304-2 2,5-Bis(trifluoromethyl)benzoyl chloride
S62043-2 p-Tolylacetyl chloride
16171-3 3,5-Dimethoxybenzoyl chloride
42339-4 (R)-(-)-A-Methoxy-A-(trifluoromethyl)-phenylacetyl chloride
26480-6 2,5-Dimethoxyphenylacetyl chloride
25804-0 3,4-Dimethoxybenzoyl chloride
T6980-9 3,4,5-Trimethoxybenzoyl chloride
26242-0 2,6-Dimethoxybenzoyl chloride
13430-9 trans-2-Phenyl-1-cyclopropanecarbonyl chloride
S62264-8 5-(Dimethylsulfamoyl)-2-methoxybenzoyl chloride
37383-4 2,4-Dimethoxybenzoyl chloride
A1740-4 o-Acetylmandelic chloride
24945-9 4-Phenyl-1,2,3,4-tetrachloro-1,3-butadiene-1-carbonyl cloride
36848-2 trans-3-(trifluoromethyl)cinnamoyl chloride
15712-0 4-tert-butylbenzoyl chloride
S42860-4 2-Phenylbutyryl chloride
22203-8 4-Butylbenzoyl chloride
23747-7 3,4-Dimethoxyphenylacetyl chloride
22204-6 4-Butoxybenzoyl chloride
S65659-3 2-(4-Chlorobenzoyl)benzoyl chloride
22214-3 4-Pentylbenzoyl chloride
C3928-8 2-Chloro-2,2-diphenylacetyl chloride
S43639-9 4(4-Nitrophenylazo)benzoyl chloride
33158-9 Diphenylacetyl chloride
S80926-8 4-(Phenylazo)benzoyl chloride
S61661-3 2-Diphenylacetyl chloride
16114-4 4-Biphenylcarbonyl chloride
22209-7 4-Hexylbenzoyl chloride
22205-4 4-Heptyloxybenzoyl chloride
22211-9 4-Hexyloxybenzoyl chloride
22206-2 4-Heptyloxybenzoyl chloride

EXAMPLE 124

Loading of Solid Support, General Procedure

Method 1: Succinylation and Activation of Aminodiol Monomer

An FMOC protected mono-DMT aminodiol monomer (36 mmol) was dissolved in 400 ml $CH_2Cl_2$, and triethylamine (45 mmol, 6.25 ml) and succinic anhydride (40 mmol, 4.0 g) added. A catalytic amount of DMAP was added (5 mol %) and the solution stirred at room temperature overnight. TLC showed all the starting material was converted to a more polar spot. To the solution was then added pentafluorophenyl trifluoroacetate (6.9 ml, 40 mmol). The solution was stirred 1 hr, and the polar material was converted to a non-polar spot on TLC. Toluene (150 ml) was added, and the solvents evaporated. The oily residue was loaded on a flash chromatography column, and eluted with ethyl acetate and hexanes to give the product (33 mmol, 93%).

Method 2: Derivatization of TentaGel

TentaGel-$NH_2$ (50 g, 11 mmol $NH_2$) was swelled in 150 ml $CH_2Cl_2$, then washed with 5% diisopropylethylamine in $CH_2Cl_2$, followed by $CH_2Cl_2$. The resin was sucked dry, and a solution of monomer succinate PFP ester (17 mmol) in 120 ml $CH_2Cl_2$ and triethylamine (3.5 ml, 25 mmol) were added. The solution was agitated on a wrist shaker for 6 hours, filtered and rinsed with $CH_2Cl_2$, and a second portion of PFP ester (16 mmol) and triethylamine (3.5 ml) added. The solid support was shaken overnight, filtered and resuspended in 60 ml $CH_2Cl_2$, 60 ml pyridine and 10 ml acetic anhydride added. After 1 hr, the resin was filtered and washed with $CH_2Cl_2$, pyridine/$CH_2Cl_2$/Methanol (1:8:1), and diethyl ether. The resin was dried under high vacuum. The loading was determined by DMT cation to be 0.14–0.20 mmol/g.

EXAMPLE 125

Derivatization of Scaffolds on Solid Support. General Procedure for Acylation of Scaffold Monomers with Carboxylic Acids An aminodiol monomer on a solid support (0.5 g Tentagel, 0.15 mmol/g) is placed in a shaker flask and purged with argon for 15 minutes. The support is pre-swelled in $CH_2Cl_2$ (60 min.) then washed with DMF(6 ml). The FMOC protecting group, if present, is removed by addition of piperidine/DMF (10%, 6 mL, ~80 eq.), followed by agitation of the reaction mixture for 15 minutes. The support was washed with DMF (6 ml×5). A solution of a carboxylic acid (0.4 M, ~5 eq.) and DIEA (0.8 M, ~10 eq.) in DMF was added, followed by a solution of activator, BOP or HATU in DMF (0.4 M, 5 eq). The reaction mixture was agitated (30 min.) and then washed with DMF (6 ml×3) and $CH_2Cl_2$ (6 ml×3). Several other activating agents can be used. These include carbodiimides such as dicyclohexyl carbodiimide (DCC), diisopropyl carbodiimide (DIC), dimethylaminopropyl ethyl carbodiimide hydrochloride (EDC), EEDQ and IIDQ, carbonyl diimidazole, with or without the addition of additives such as dimethylaminopyridine, N-hydroxybenzotriazole, N-hydroxy-7-azabenzotriazole, and others known to those skilled in the art. Other useful coupling agents include substituted uronium salts and phosphonium salts such as HBTU, TBTU, BOP, PyBROP and other analogous reagents, and reagents for producing acyl fluorides, such as cyanuric fluoride. Representative examples of each of these reagents can be found in Bodanszky, M. Principles of Peptide Synthesis, 2nd Ed. Springer-Verlag, Berlin, 1993.

Representative carboxylic acids that can be used to derivatize an amino group of an aminodiol of the invention include:
2-oxovaleric acid
2-oxo-octanoic acid
2-oxo-2-(2-furyl)acetic acid
indole-3-pyruvic acid
2-nitrophenylpyruvic acid
2-furylthiopyruvic acid
methacrylic acid
2-methylpropionic acid (isobutyric acid)
cyanoacetic acid
methoxyacetic acid
3-methylthiopropionic acid
4-methylpentanoic acid
3-trimethylsilylpropionic acid sodium salt
N-BOC-5-aminovaleric acid
3-(N,N-diethylamino)propionic acid hydrochloride
monomethyl glutarate
7-oxo-octanoic acid
neodecanoic acid
1,2,3-thiadiazole-4-carboxylic acid
3-amino-1,2,4-triazole-5-carboxylic acid
3-furoic acid
2-furoic acid
4-(S)-butyrolactone-4-carboxylic acid 1-methylpyrrole-2-carboxylic acid
4-methyl-2-phenyl-1,2,3-triazole-5-carboxylic acid
1-(3'-aminophenyl)-3-carboxy-5-pyrazolone
4-phenyl-5-trifluoromethyl-thiophene-2-carboxylic acid
3-(4-chlorophenylthio)thiophene-4-carboxylic acid
5-(2-pyridylthiomethyl)-2-furancarboxylic acid
indole-2-carboxylic acid
1-methylindole-2-carboxylic acid
7-benzyloxyindole-2-carboxylic acid
4-oxo-4,5,6,7-tetrahydrobenzo[b]furan-3-carboxylic acid
1-methylindene-2-carboxylic acid
4-chloro-3-sulfamoylbenzoic acid
2-hydroxybenzoic acid (salicylic acid)
a-mercapto-p-toluic acid
BOC 4-(aminomethyl)benzoic acid
BOC 4-(methylamino)benzoic acid
N-acetyl-4-aminobenzoic acid
4-isopropoxybenzoic acid
4-(2-[methylsulfonamido]ethoxy) benzoic acid
4-(1H-pyrrol-1-yl)benzoic acid
4-(3-methyl-5-oxo-2-pyrazolin-1-yl)benzoic acid
4'-(trifluoromethyl)-2-biphenylcarboxylic acid
2-(4-nitrophenylthio)benzoic acid
2-phenoxybenzoic acid
2-(4-chlorobenzoyl)benzoic acid
2-benzoylbenzoic acid
a-phenyl-o-toluic acid
a-(4-methoxy-1-naphthyl)-o-toluic acid
2-(1,2,3,4-tetrahydro-6-naphthylmethyl)benzoic acid
2-(2-pyridylcarbonyl)benzoic acid
4-(3-fluorobenzamido)benzoic acid
3'-carboxy-3-methylbenzanilide
2'-methoxyphthalanilic acid
3-benzyloxy-4-methoxybenzoic acid
N-(3-methyl-2-pyridyl)phthalamic acid
1-(4-carboxyphenyl)-3-(o-tolyl)urea
benzotriazole-5-carboxylic acid
5-benzimidazolecarboxylic acid
piperonylic acid
2,2,5,7-tetramethylindan-1-one-4-carboxylic acid
2-naphthoic acid
2-pyrazinecarboxylic acid
picolinic acid
nicotinic acid
isonicotinic acid
6-hydroxynicotinic acid
tetrahydropyran-4-carboxylic acid
N-BOC 4-piperidinecarboxylic acid (isonipecotic acid)
1,3-dimethyl-6-uracilcarboxylic acid
2-pyrrolopyridine-5-carboxylic acid
2-phenoxynicotinic acid
2-(4-methylphenoxy)pyridine-3-carboxylic acid
2-phenylimidazo(1,2-A)pyridine-6-carboxylic acid
3-isoquinolinecarboxylic acid
4-quinolinecarboxylic acid
4-hydroxy-7-trifluoromethyl-3-quinolinecarboxylic acid
2-p-tolylcinchoninic acid
nalidixic acid
thiophene-2-acetic acid
5-(1-pyrrolidine)2-tetrazoleacetic acid
N-phthaloylglycine
indole-3-acetic acid
cyclopentylacetic acid
2-indanylacetic acid
pentafluorophenylacetic acid
2-(2-fluorophenyl)acetic acid
(S)-(+)-mandelic acid
(a,a,a-trifluoro-m-tolyl)acetic acid
R-(−)-a-methoxyphenylacetic acid
2-(4-chlorophenyl)-2,2-dimethylacetic acid
(R)-(−)-2-phenylbutyric acid
(3,4-dimethoxyphenyl)acetic acid]
4-(dimethylamino)phenylacetic acid
4-biphenylacetic acid
2-benzyloxyphenylacetic acid
1-(4-methylphenyl)-1-cyclopropanecarboxylic acid
benzilic acid
orotic acid
4-pyridylacetic acid hydrochloride
phenylacetic acid
2-(2-phenyl-1-cyclohexenyl)acetic acid
trans-3-furanacrylic acid
2-methyl-4-nitro-1-imidazolepropionic acid
5-phenyl-2-pyrrolepropionic acid
2-(4-chlorophenoxy)acetic acid
phenoxyacetic acid
N-phenylglycine
2,5-difluorocinnamic acid
3-(4-iodophenyl)propionic acid
N-(2,4-dinitrophenyl)-L-alanine
3-(3-hydroxyphenyl)propionic acid
p-toluenesulfonylacetic acid
BOC-3-(p-aminophenyl)propionic acid
4-cyanocinnamic acid
4-methoxycinnamic acid
2-(p-chlorophenoxy)-2-methylpropionic acid
p-(p-nitrobenzyloxy)cinnamic acid
2-naphthoxyacetic acid
3,3-diphenylpropionic acid
3,5,6-trichloro-2-pyridoxyacetic acid
4-pyridylthioacetic acid
5-trifluoromethyl-2-pyridylthioacetic acid
1-piperidinepropionic acid
4-oxo-4-(1-pyrrolidine)butyric acid
3-(4-fluorobenzoyl)propionic acid
3-benzoylpropionic acid
N-methylhippuric acid
4-oxo-4-(2-trifluoromethylphenyl)butyric acid
3-(4-methoxybenzoyl)propionic acid
3-(4-methylsulfonylbenzoyl)propionic acid
4-(4-acetylphenyl)butyric acid
4-oxo-4-(2-naphthyl)butyric acid
dansyl glycine
3-(4-methoxy-1-naphthoyl)propionic acid
(−)-O,O'-dibenzoyl-L-tartaric acid mono(dimethylamide)
1-(3-carboxy-1-oxopropyl)-1,2,3,4-tetrahydroquinoline
1,2-dihydro-2-methyl-1-oxo-3-isoquinolinebutyric acid
2-(2-carboxyethylthio)-3,5,6-trimethyl-1,4-benzoquinone
(+)-biotin
4-(2-mercaptobenzothiazolyl)butyric acid
Z-styrenesulfonylacetic acid
4-(p-chlorophenoxy)butyric acid
3-(benzylthio)propionic acid
N-(2-pyridyl)succinamic acid
Cbz-glycine
2-[(2-phenoxyethyl)thio]acetic acid
2-(benzenesulfonyl)ethylthioacetic acid
2'-carbamoylglutaranilic acid.

EXAMPLE 126

Acylation of Scaffold Monomers with Acyl Chlorides, Anhydrides, and Activated Carboxylic Acid Derivatives An aminodiol monomer on a solid support (0.5 g Tentagel, 0.15 mmol/g) was placed in a shaker flask and purged with argon (15 min.). The support was pre-swelled in CH$_2$Cl$_2$ (60 min.) then washed with DMF(6 ml). The FMOC protecting group, if present, is removed by addition of piperidine/DMF (10%, 6 mL, ~80 eq.), followed by agitation of the reaction mixture for 15 minutes. The support was washed with DMF (6 ml×5). A solution of py/DMF (10%, 3 mL, ~50 eq.), acid chloride/DMF (0.12 M, 3 mL, ~5 eq.) was added, and the reaction mixture agitated for 30 minutes. A solution of acid anhydride or other activated derivative in DMF could be used instead of acid chloride. The support was then washed with DMF (6 ml×3) and CH$_2$Cl$_2$ (6 ml×3). Examples of reagents which can be substituted for acid chlorides are: acid anhydrides and mixed anhydrides, imidazolides, or active esters such as N-hydroxy succinimide esters and other O-acyl hydroxylamine derivatives, acyl azides, 4-nitrophenol esters, pentachlorophenyl or pentafluorophenyl esters and other active aryl and vinyl esters. Representative examples of each of these reagents can be found in Bodanszky, M. Principles of Peptide Synthesis, 2nd Ed. Springer-Verlag, Berlin, 1993.

EXAMPLE 127

Sulfonylation of Scaffold Monomers

An aminodiol monomer on a solid support (0.5 g Tentagel, 0.15 mmol/g) was placed in a shaker flask and purged with argon (15 min.). The support was pre-swelled in CH$_2$Cl$_2$ (60 min.) then washed with DMF(6 ml). The FMOC protecting group, if present, is removed by addition of piperidine/DMF (10%, 6 mL, ~80 eq.), followed by agitation of the reaction mixture for 15 minutes. The support was washed with DMF (6 ml×5). A solution of TEA/CH$_3$CN (10%, 3 mL, ~30 eq.) was added followed by the sulfonyl chloride in CH3CN/Pyridine (0.12 M, 3 mL, ~5 eq.), and the reaction mixture agitated for 30 minutes. The support was washed with pyridine (6 ml×3), DMF (6 ml×3) and CH$_2$Cl$_2$ (6 ml×3).

Representative sulfonyl chlorides suitable for use in the invention include:
methanesulfonyl chloride
dimethylsulfamoyl chloride
1-butanesulfonyl chloride
3,5-dimethylisoxazole-4-sulfonyl chloride
5-(4-chlorobenzamidomethyl) thiophene-2-sulfonyl chloride
benzenesulfonyl chloride
o-carbomethoxybenzenesulfonyl chloride
N-acetylsulfanilyl chloride
2,5-dimethoxybenzenesulfonyl chloride
3-(chlorosulfonyl)benzoic acid
2-dibenzofuransulfonyl chloride
2-naphthalenesulfonyl chloride
8-quinolinesulfonyl chloride
phenylmethanesulfonyl chloride
(+/−)-10-camphorsulfonyl chloride
N-acetylsulfanilyl chloride
3,5-dichlorobenzene sulfonyl chloride
dansyl chloride.

EXAMPLE 128

Alkylation of Scaffold Monomers

An aminodiol monomer on a solid support (0.5 g Tentagel, 0.15 mmol/g) was placed in a shaker flask and purged with argon (15 min.). The support was pre-swelled in CH$_2$Cl$_2$ (60 min.) then washed with DMF (6 ml). The FMOC protecting group, if present, is removed by addition of piperidine/DMF (10%, 6 mL, ~80 eq.), followed by agitation of the reaction mixture for 15 minutes. The support was washed with DMF (6 ml×5). A solution of DIEA in DMF (10%, 3 mL, ~50 eq.), alkylating reagent (Alkyl halide, mesylate, tosylate or triflate) in DMF (0.2 M, 3 mL, ~5 eq.) is added, and the reaction mixture is agitated for 120 min. The support is then washed with DMF (6 ml×3) and CH$_2$Cl$_2$ (6 ml×3).

EXAMPLE 129

Synthesis of Ureas on Solid Support

An aminodiol monomer on a solid support (0.5 g Tentagel, 0.15 mmol/g) was placed in a shaker flask and purged with argon (15 min.). The support was pre-swelled in CH$_2$Cl$_2$ (60 min.) then washed with DMF(6 ml). The FMOC protecting group, if present, is removed by addition of piperidine/DMF (10%, 6 mL, ~80 eq.), followed by agitation of the reaction mixture for 15 minutes. The support was washed with DMF (6 ml×5). A solution of isocyanate in DMF (2.0 ml, 0.2M) is added, followed by DMAP in DMF (2.0 ml, 0.02M) and the resulting mixture agitated (120 min.). The support is then washed with DMF (6 ml×3) and CH$_2$Cl$_2$ (6 ml×3).

Representative isocyanates suitable for use in the invention include:
benzoyl isocyanate
4-chlorobenzenesulfonyl isocyanate
benzenesulfonyl isocyanate
3-nitrophenyl isocyanate
4-acetylphenyl isocyanate
2,5-dimethylphenyl isocyanate
ethyl 4-isocyanatobenzoate
2-phenylphenyl isocyanate
4-phenoxyphenyl isocyanate
1-naphthyl isocyanate
R-(+)-a-methylbenzyl isocyanate
Methyl Isocyanate
Isopropyl Isocyanate
Cyclohexyl isocyanate
Allyl Isocyanate
Chloromethyl Isocyanate
Chloropropyl Isocyanate
Ethyl Isocyanatoacetate
4-(Chloromethyl) phenyl isocyanate
3-Chlorophenyl Isocyanate
4-Fluorophenyl Isocyanate
Ethyl 4-Isocyanatobenzoate
3,5-Dichlorophenyl Isocyanate

EXAMPLE 130

Quality Control

An aliquot (5 mg) of a scaffold attached to a solid support that has been derivatized is placed in a 1 mL disposable syringe fitted with glass wool plug. TCA/CH$_2$Cl$_2$ (3%, 0.4 ml×5) is drawn in, and the reaction mixture is agitated manually to remove the DMT. The support is washed with CH$_2$Cl$_2$ (6 ml×3) and pyridine-CH$_3$CN (6 ml×3). DMT-deoxythymidine H-phosphonate in pyridine-CH$_3$CN (0.1 M, 0.4 mL, ~50 eq.) is added, followed by a solution of adamantoyl chloride in pyridine-CH$_3$CN, and the reaction mixture is agitated manually for 3 minutes. The support is washed with pyridine-CH$_3$CN (1 ml×3) and THF (1 ml×3). Oxidation of the H-phosphonate diester is achieved by adding a solution of I$_2$ in THF (0.2 M, 0.4 mL, ~100 eq.) and H$_2$O/TEA/THF (1:1:8, 0.4 mL), and agitating periodically. The support is washed with THF (1 mL×3), pyridine-CH$_3$CN (1 mL×5), DMF (1 mL×3), CH$_2$Cl$_2$ (1 mL×3), and MeOH (1 mL×3). NH$_4$OH (28–30%, 0.5 mL) is added to cleave the product from the support. After 1–2 hours, the ammonia solution is collected in vials and subjected to HPLC and mass spectrometric analyses.

EXAMPLE 131

(S)-2-t-Butoxycarbonyl-1,2,3,4-tetrahydro-7-hydroxyisoquinoline-3-carboxylic Acid The title compound was made by the method of Verschueren, K., Thoth, G., Tourwé, D., Lebl, M., Van Binst, G., Hruby, V. *Synthesis*, 1992, 5, 458–4602.

EXAMPLE 132

(S)-2-t-Butoxycarbonyl-1,2,3,4-tetrahydro-3-hydroxymethyl-7-hydroxyisoquinoline (S)-2-t-Butoxycarbonyl-1,2,3,4-tetrahydro-7-hydroxyisoquinoline-3-carboxylic acid (100 mmol) is dissolved in THF (1 L). Borane methyl sulfide complex (200 mmol) is added carefully, and the solution heated at reflux for 1 hour. The solution is cooled, quenched with MeOH, and 1 N HCl to pH 2. The solution is neutralized to pH 7–8 with NaHCO$_3$ and the solvent evaporated. The oily residue is diluted with water, extracted with EtOAC, washed with NaHCO$_3$ and brine, then dried with MgSO$_4$ and evaporated to give the title compound.

EXAMPLE 133

(S)-2-t-Butoxycarbonyl-3-hydroxymethyl-7-hydroxyoctahydroisoquinoline

To a solution of t-butyl alcohol (9.1 g, 123 mmol), 50 ml ether, and ammonia (150 mL) is added (S)-2-t-butoxycarbonyl-1,2,3,4-tetrahydro-3-hydroxymethyl-7-hydroxyisoquinoline (5 mmol). The solution is brought to reflux, and lithium shot (0.51 g, 82 mmol) is added over 30 minutes. The solution is allowed to reflux for 3 hours, and solid NH$_4$Cl added until the color disappears. The ammonia is allowed to evaporate overnight, ice-water is added, and the organic layer separated. The aqueous layer is extracted with chloroform and the combined organic phases are washed with brine, dried and evaporated. The crude product is redissolved in methanol, 5% Pt/C added and the solution shaken under 3 atm H$_2$ for 6 hours to complete the reduction. The catalyst is filtered and the solvent evaporated. The resulting residue is purified by silica gel flash column chromatography to give the title compound.

EXAMPLE 134

(S)-2-FMOC-3-hydroxymethyl-7-hydroxyoctahydroisoquinoline

The Boc protected material from the previous example is dissolved in ethyl acetate and 1 N HCl in ethyl acetate is added. The solution is stirred until all the starting material is consumed. The solvent is evaporated and the residue redissolved in 2M NaHCO$_3$ (25 ml) and dioxane (25 ml). FMOC-Cl is added and the solution stirred for 6 hours. The solvent is evaporated, and the product is extracted with ethyl acetate, washed with NaHCO$_3$, and then brine, dried with MgSO$_4$, and evaporated. The resulting residue is purified by silica gel flash column chromatography to give the title compound.

EXAMPLE 135

(S)-2-FMOC-3-dimethoxytrityloxymethyl-7-hydroxyoctahydroisoquinoline

The product from the previous example is dissolved in pyridine, cooled to 0° C. and 1.2 eq DMT-Cl added. The solution is stirred overnight at 0° C., quenched with methanol, and the solvent evaporated. The residue is redissolved in EtOAc, washed with 5% citric acid, NaHCO$_3$, and brine, and evaporated. The resulting residue is purified by silica gel flash column chromatography to give the title compound.

EXAMPLE 136

1-BOC-3-hydroxymethylpyrrole

The title compound is prepared according to the method of Davies, H. M. L., Matasi, J. J., Ahmed, G. *J. Org. Chem.* 1996, 61, 2305.

EXAMPLE 137

1-BOC-3-O-TBDMS-hydroxymethylpyrrole

1-BOC-3-hydroxymethylpyrrole (2.5 eq) and imidazole (2.5 eq) are dissolved in DMF and TBDMS-Cl (1.2 eq) is added. The solution is stirred overnight, quenched with water, and extracted with EtOAc. The extracts are washed with water, NaHCO$_3$, and brine, and dried with MgSO$_4$. The resulting residue is purified by silica gel flash column chromatography to give the title compound.

EXAMPLE 138

Methyl-3-O-TBDMS-6-(O-TBDMS)-oxymethyl-8-BOC-8-azabicyclo[3.2.1.]octa-2,6-diene-2-carboxylate A solution of methyl 2-diazoacetoacetate (25 mmol) and triethylamine (30 mmol) in CH$_2$Cl$_2$ is cooled to 0° C., and TBDMS-triflate (27 mmol) is added. The solution is stirred at 0° C. for 30 minutes, diluted with hexane, and washed with 5% NaHCO$_3$. The extracts are dried and evaporated, and the crude enol silyl ether is used directly. The enol ether is dissolved in hexane (50 mL), and added slowly to a solution of 1-BOC-3-O-TBDMS-hydroxymethylpyrrole (20 mmol) and rhodium (II) hexanoate in refluxing hexane (50 mL) under an atmosphere of argon. The solution is heated a further 12 hours and evaporated. The product is purified by flash cromatography. The resulting residue is purified by silica gel flash column chromatography to give the title compound.

EXAMPLE 139

Methyl-3-O-TBDMS-6-(O-TBDMS)-oxymethyl-8-BOC-8-azabicyclo[3.2.1.]octa-2-ene-2-carboxylate The diene product of the previous example and tris (triphenylphosphine) rhodium chloride (5 mol %) are dissolved in ethanol, and shaken under 45 psi H$_2$ for 12 hours. The solvent is evaporated and the resulting residue is purified by silica gel flash column chromatography to give the title compound.

EXAMPLE 140

Methyl-3-oxo-6-hydroxymethyl-8-BOC-8-azabicyclo[3.2.1.]octane-2-carboxylate

The bis silyl ether of the previous example is dissolved in THF, and a solution of tetrabutylammonium fluoride in THF

EXAMPLE 141

3-Oxo-6-hydroxymethyl-8-BOC-8-azabicyclo [3.2.1.]octane

The keto ester of the previous example is dissolved in DMSO, and 1 eq NaCl and 1 eq $H_2O$ added. The solution is heated to 160° C. for 1 hour in an open vessel, cooled to room temperature and diluted with water. The suspension is extracted with EtOAc, washed with 5% $NaHCO_3$, brine, dried over $MgSO_4$, and evaporated. The resulting residue is purified by silica gel flash column chromatography to give the title compound.

EXAMPLE 142

3-Oxo-6-O-DMT-oxymethyl-8-FMOC-8-azabicyclo [3.2.1.]octane 3-oxo-6-hydroxymethyl-8-BOC-8-azabicyclo[3.2.1.] octane is dissolved in ethyl acetate and 1 N HCl in ethyl acetate is added. The solution is stirred until all the starting material is consumed. The solvent is evaporated and the residue redissolved in 2M $NaHCO_3$ (25 mL) and dioxane (25 mL). FMOC-Cl is added and the solution stirred for 6 hours. The solvent is evaporated, and the product extracted with ethyl acetate, washed with $NaHCO_3$, brine, dried over $MgSO_4$, and evaporated. The crude material is dissolved in pyridine, cooled to 0° C. and 1.2 eq DMT-Cl added. The solution is stirred overnight at 0° C., quenched with methanol, and the solvent evaporated. The residue is redissolved in EtOAc, washed with 5% citric acid, $NaHCO_3$, brine and evaporated. The resulting residue is purified by silica gel flash column chromatography to give the title compound.

EXAMPLE 143

3-Hydroxy-6-O-DMT-oxymethyl-8-FMOC-8-azabicyclo[3.2.1.]octane

The product from the previous example is dissolved in THF and 1 eq of a solution of $LiBH_4$ is added. The solution is stirred until the starting material was consumed. The reaction is carefully quenched to pH 4 (wet litmus), and neutralized with $NaHCO_3$. The solvent is evaporated, the residue extracted with ethyl acetate, washed with $NaHCO_3$, brine, dried and evaporated. The product is purified by flash chromatography.

EXAMPLE 144

N-Methyl-2,6-diacetoxy-9-azabicyclo[3.3.1]nonane

The title compound is made by the method of Clousdale, I. S., Kluge, A. F., McClure, N. L. *J. Org. Chem.* 1982, 47, 919.

EXAMPLE 145

2,6-Diacetoxy-9-azabicyclo[3.3.1]nonane

The material from the previous example (10 mmol) is dissolved in 100 ml 1,2-dichloroethane, cooled to 0° C. and 1-chloroethyl chloroformate (11 mmol) is added. The solution is warmed to reflux temperature after 15 minutes, and heated until the starting material is consumed. The solvent is then removed, and the residue redissolved in anhydrous methanol, and warmed to 50° C. for 1 hour. The solvent is removed to give the title compound as the HCl salt.

EXAMPLE 146

2,6-Dihydroxy-9-FMOC-9-azabicyclo[3.3.1]nonane

The material from the previous example (10 mmol) is dissolved in 50 ml 1:1 aqueous THF, and 50 mmol LiOH added. The biphasic solution is stirred at room temperature for 6 hours. A solution of FMOC-Cl (11 mmol) in THF is then added dropwise at room temperature over 15 minutes. After 1 hour the solution is acidified with 10% HCl to pH 2, and extracted with EtOAc, washed with water, brine and dried with $MgSO_4$. The product is purified by flash chromatography.

EXAMPLE 147

2-O-DMT-6-hydroxy-9-FMOC-9-azabicyclo[3.3.1.] nonane

The diol from the previous example (10 mmol) is dissolved in $CH_2Cl_2$ and pyridine (9:1), cooled to 0° C. and DMT-Cl (10 mmol) is added in portions (1.0 eq). The solution is stirred overnight at 0° C. The reaction is quenched with MeOH, evaporated, and excess solvent is removed by azeotropic distillation with toluene. The residue is redissolved in EtOAc, washed with 5% citric acid, $NaHCO_3$, brine and dried with $MgSO_4$. The product is purified by flash chromatography using a gradient of MeOH in $CH_2Cl_2$. The product is obtained in 50% yield, along with 25% ditritylated material which is conserved and recycled, and 25% unreacted starting material.

EXAMPLE 148

Dimethyl 3-O-TBDMS-glutarate

Dimethyl 3-hydroxyglutarate (34 mmol) and imidazole (85 mmol) are dissolved in 150 ml DMF, and TBDMS-Cl added (40 mmol). The solution is stirred overnight, quenched with water (400 ml), extracted with EtOAc, washed with $NaHCO_3$, brine and dried with $MgSO_4$ to give the title compound.

EXAMPLE 149

3-O-TBDMS-1,5-pentanediol

The material from the previous example in dissolved in dry THF and 35 ml of 2M $LiBH_4$ in THF added. The solution is heated to reflux for 1.5 hrs, cooled to room temperature and quenched carefully with 10% HCl to pH 2, neutralized with $NaHCO_3$ and evaporated. The residue is extracted with EtOAc, washed with $NaHCO_3$, brine and dried with $MgSO_4$ to give the title compound.

EXAMPLE 150

N-Methyl-3-O-TBDMS-7-keto-9-azabicyclo[3.3.1] nonane

To a stirred solution of oxalyl chloride (10 mmol) in 20 ml THF at −78° C. is added 11 mmol dimethylsulfoxide. The solution is warmed to −35° C. for 5 minutes and recooled to (continued at top of page: is added (3 eq). The solution is stirred at room temperature until the starting material is consumed. The solvent is evaporated, the residue redissolved in ether and washed with dilute $NaHCO_3$, brine, and dried with $MgSO_4$. The crude material is filtered through silica gel to give the title compound.)

−78° C. A solution of 3-O-TBDMS-1,5-pentanediol (5 mmol) in 10 ml THF is added, and the solution warmed to 0° C. After 15 minutes, triethylamine (40 mmol) is added and the solution stirred at room temperature to effect complete conversion to the dialdehyde. The solvent is evaporated under reduced pressure, and the crude dialdehyde is redissolved in 40 ml citrate/phosphate buffer (pH 5.5) to which is added 15 mmol methylamine hydrochloride in 50 ml water, followed by the dropwise addition of 12 mmol acetone dicarboxylate in 80 ml water. The solution is stirred 24 hrs, 5 ml concentrated HCl added, and the solution heated to 90° C. for 1 hr to complete the decarboxylation. Sodium hydroxide is added to pH 12, and the solution extracted with $CH_2Cl_2$, dried over $MgSO_4$ and purified by chromatography on alumina to yield the product.

EXAMPLE 151

N-FMOC-3-O-TBDMS-7-keto-9-azabicyclo[3.3.1]nonane

The material from the previous example (10 mmol) is dissolved in 100 ml 1,2-dichloroethane, cooled to 0° C. and 1-chloroethyl chloroformate (22 mmol) is added. The solution is warmed to reflux temperature after 15 minutes, and heated until the starting material is consumed. The solvent is then removed, and the residue redissolved in anhydrous methanol, and warmed to 50° C. for 1 hour. The solvent is removed and the residue redissolved in 25 ml THF and 25 ml saturated $NaHCO_3$. A solution of FMOC-Cl (11 mmol) in THF is then added dropwise at room temperature over 15 minutes. After 1 hr the solution is acidified with 10% HCl to pH 2, and extracted with EtOAc, washed with water, brine and dried with $MgSO_4$. The product is purified by flash chromatography.

EXAMPLE 152

N-FMOC-3-O-TBDMS-7-hydroxy-9-azabicyclo[3.3.1]nonane

The material from the previous example (10 mmol) in dissolved in dry THF and 6 ml of 2 M $LiBH_4$ in THF added. The solution is stirred at room temperature and quenched carefully with 10% HCl to pH 2, neutralized with $NaHCO_3$ and evaporated. The residue is extracted with EtOAc, washed with $NaHCO_3$, brine and dried with $MgSO_4$.

EXAMPLE 153

N-FMOC-3-O-TBDMS-7-O-DMT-9-azabicyclo[3.3.1]nonane

The alcohol from the previous example (10 mmol) is dissolved in $CH_2Cl_2$ and pyridine (9:1), cooled to 0° C. and DMT-Cl (11 mmol) added in portions (1.0 eq). The solution is stirred overnight at room temperature. The reaction is quenched with MeOH, evaporated, and excess solvent removed by azeotropic distillation with toluene. The residue is redissolved in EtOAc, washed with 5% citric acid, $NaHCO_3$, brine and dried with $MgSO_4$. The product is purified by silica gel flash chromatography with a gradient of MeOH in $CH_2Cl_2$.

EXAMPLE 154

N-FMOC-3-hydroxy-7-O-DMT-9-azabicyclo[3.3.1]nonane

The product of the previous example is added to a solution of triethylamine trihydrofluoride (100 mmol) and triethylamine (50 mmol) in 50 ml of THF. The solution is stirred until the starting material is completely consumed. The reaction is stopped by the addition of saturated $NaHCO_3$ followed by evaporation of the solvent. The residue is extracted with EtOAc, washed with $NaHCO_3$, brine and dried with $MgSO_4$. The product is purified by flash chromatography.

EXAMPLE 155

N-Methyl-2,6-diacetoxy-9-azabicyclo[3.3.1]nonane

The title compound is made by the method of Clousdale, I. S., Kluge, A. F., McClure, N. L. *J. Org. Chem.* 1982, 47, 919.

EXAMPLE 156

2,6-Diacetoxy-9-azabicyclo[3.3.1]nonane

The material from the previous example (10 mmol) is dissolved in 100 ml 1,2-dichloroethane, cooled to 0° C. and 1-chloroethyl chloroformate (11 mmol) is added. The solution is warmed to reflux temperature after 15 minutes, and heated until the starting material is consumed. The solvent is then removed, and the residue redissolved in anhydrous methanol, and warmed to 50° C. for 1 hour. The solvent is removed to give the title compound as the HCl salt.

EXAMPLE 157

2,6-Dihydroxy-9-FMOC-9-azabicyclo[3.3.1]nonane

The material from the previous example (10 mmol) is dissolved in 50 ml 1:1 aqueous THF, and 50 mmol LiOH added. The biphasic solution is stirred at room temperature for 6 hours. A solution of FMOC-Cl (11 mmol) in THF is then added dropwise at room temperature over 15 minutes. After 1 hr the solution is acidified with 10% HCl to pH 2, and extracted with EtOAc, washed with water, brine and dried with $MgSO_4$. The product is purified by flash chromatography.

EXAMPLE 158

2-O-DMT-6-hydroxy-9-FMOC-9-azabicyclo[3.3.1]nonane

The diol from the previous example (10 mmol) is dissolved in $CH_2Cl_2$ and pyridine (9:1), cooled to 0° C. and DMT-Cl (10 mmol) is added in portions (1.0 eq). The solution is stirred overnight at 0° C. The reaction is quenched with MeOH, evaporated, excess solvent removed by azeotropic distillation with toluene. The residue is redissolved in EtOAc, washed with 5% citric acid, $NaHCO_3$, brine and dried with $MgSO_4$. The product is purified by flash chromatography on a gradient of MeOH in $CH_2Cl_2$. The product is obtained in 50% yield, along with 25% ditritylated material which is conserved and recycled, and 25% unreacted starting material.

EXAMPLE 159

Dimethyl 3-O-TBDMS-glutarate

Dimethyl 3-hydroxyglutarate (34 mmol) and imidazole (85 mmol) are dissolved in 150 ml DMF, and TBDMS-Cl added (40 mmol). The solution is stirred overnight, quenched with water (400 ml), extracted with EtOAc, washed with $NaHCO_3$, brine and dried with $MgSO_4$.

EXAMPLE 160

3-O-TBDMS-1,5-pentanediol

The material from the previous example in dissolved in dry THF and 35 ml 2 M LiBH$_4$ in THF added. The solution is heated at reflux for 1.5 hrs, cooled to room temperature and quenched carefully with 10% HCl to pH 2, neutralized with NaHCO$_3$ and evaporated. The residue is extracted with EtOAc, washed with NaHCO$_3$, brine and dried with MgSO$_4$.

EXAMPLE 161

N-Methyl-3-O-TBDMS-7-keto-9-azabicyclo[3.3.1] nonane

To a stirred solution of oxalyl chloride (10 mmol) in 20 ml THF at −78° C. is added 11 mmol dimethylsulfoxide. The solution is warmed to −35° C. for 5 minutes and recooled to −78° C. A solution of 3-O-TBDMS-1,5-pentanediol (5 mmol) in 10 ml THF is added, and the solution warmed to 0° C. After 15 minutes, triethylamine (40 mmol) is added and the solution stirred at room temperature to effect complete conversion to the dialdehyde. The solvent is evaporated under reduced pressure, and the crude dialdehyde is redissolved in 40 ml citrate/phosphate buffer (pH 5.5) to which is added 15 mmol methylamine hydrochloride in 50 ml water, followed by the dropwise addition of 12 mmol acetone dicarboxylate in 80 ml water. The solution is stirred 24 hrs, 5 ml of concentrated Hcl is added, and the solution is heated to 90° C. for 1 hr to complete the decarboxylation. Sodium hydroxide is added to pH 12, and the solution extracted with CH$_2$Cl$_2$, dried over MgSO$_4$ and purified by chromatography on alumina.

EXAMPLE 162

N-FMOC-3-O-TBDMS-7-keto-9-azabicyclo[3.3.1] nonane

The material from the previous example (10 mmol) is dissolved in 100 ml 1,2-dichloroethane, cooled to 0° C. and 1-chloroethyl chloroformate (22 mmol) is added. The solution is warmed to reflux temperature after 15 minutes, and heated until the starting material is consumed. The solvent is then removed, and the residue redissolved in anhydrous methanol, and warmed to 50° C. for 1 hour. The solvent is removed and the residue redissolved in 25 ml THF and 25 ml saturated NaHCO$_3$. A solution of FMOC-Cl (11 mmol) in THF is then added dropwise at room temperature over 15 minutes. After 1 hr the solution is acidified with 10% HCl to pH 2, and extracted with EtOAc, washed with water, brine and dried with MgSO$_4$. The product is purified by flash chromatography.

EXAMPLE 163

N-FMOC-3-O-TBDMS-7-hydroxy-9-azabicyclo [3.3.1]nonane

The material from the previous example (10 mmol) is dissolved in dry THF and 6 ml 2 M LiBH$_4$ in THF is added. The solution is stirred at room temperature and quenched carefully with 10% HCl to pH 2, neutralized with NaHCO$_3$ and evaporated. The residue is extracted with EtOAc, washed with NaHCO$_3$, brine and dried with MgSO$_4$.

EXAMPLE 164

N-FMOC-3-O-TBDMS-7-O-DMT-9-azabicyclo [3.3.1]nonane

The alcohol from the previous example (10 mmol) is dissolved in CH$_2$Cl$_2$ and pyridine (9:1), cooled to 0° C. and DMT-Cl (11 mmol) added in portions (1.0 eq). The solution is stirred overnight at room temperature. The reaction is quenched with MeOH, evaporated, and excess solvent removed by azeotropic distillation with toluene. The residue is redissolved in EtOAc, washed with 5% citric acid, NaHCO$_3$, brine and dried with MgSO$_4$. The product is purified by silica gael flash chromatography with a gradient of MeOH in CH$_2$Cl$_2$.

EXAMPLE 165

N-FMOC-3-hydroxy-7-O-DMT-9-azabicyclo[3.3.1] nonane

The product of the previous example is added to a solution of triethylamine trihydrofluoride (100 mmol) and triethylamine (50 mmol) in 50 ml THF. The solution is stirred until the starting material is completely consumed. The reaction is stopped by the addition of saturated NaHCO$_3$ followed by evaporation of the solvent. The residue is extracted with EtOAc, washed with NaHCO$_3$, brine and dried with MgSO$_4$. The product is purified by flash chromatography.

EXAMPLE 166

Synthesis of a Trimer Containing Different Aminodiol Backbone Units

A shaker flask is charged with 10 umol (ca. 67 mg) of N-FMOC-2-O-DMT-diethylamino-2'-O-succinylamino TentaGel (abbreviated DMT-FMOC-dea-TG), prepared by succinylation of N-FMOC-2'-hydroxyethyl-2-O-DMT-ethylamine of Example 98, followed by coupling to amino Tentagel using using the General Procedure of Example 124. The DMT-FMOC-diethanolamine-TG is treated with 10% piperidine in DMF to remove the FMOC group, washed with DMF, and then with CH$_2$Cl$_2$. The free amine is acylated with cyclohexane carboxylic acid using HATU as the coupling agent following General Procedure of Example 125 and Example 126 to give DMT-de(CH)-TG. The resin is washed with DMF and CH$_2$Cl$_2$, the trityl group removed with 3% TCA in CH$_2$Cl$_2$, and the resin washed with CH$_2$Cl$_2$ and pyridine/CH$_3$CN (1:1). The resin is then treated with the second scaffold H-phosphonate of Example 81 (abbr. DMT-FMOC-pd-Hphos) and adamantoyl chloride in pyridine/CH$_3$CN using the method of the General Procedures of Example 69 and Example 73. After washing with pyridine/CH$_3$CN, the resin is treated with a 10% solution of isopropoxyethylamine in carbon tetrachloride/pyridine (1:1) for 20 minutes. The amine solution is removed and the resin washed with DMF, followed by 10% piperidine in DMF to remove the second FMOC group. After washing the resin with DMF, the dimer is acylated with Thiophene carboxylic acid and HATU using the General Procedure. After the acylation is complete, the resin is again washed with DMF, CH$_2$Cl$_2$ and detritylated with 3% TCA in CH$_2$Cl$_2$, and then washed with pyridine/CH$_3$CN (1:1). The resin is then treated with the third scaffold H-phosphonate of Example 59 (abbr. DMT-FMOC-hp-Hphos) and adamantoyl chloride in pyridine/CH$_3$CN using the method of the General Procedures of Example 69 and Example 73. After washing with pyridine/CH$_3$CN, the resin is treated with a 10% solution of 3-aminomethylpyridine in carbon tetrachloride/pyridine (1:1) for 20 minutes. The amine solution is removed and the resin washed with DMF, followed by 10% piperidine in DMF to remove the third FMOC group. After washing the resin with DMF, the trimer is acylated with 4-nitrobenzoic acid and HATU using the General Procedure. The resin is washed with DMF, CH$_2$Cl$_2$, and detritylated with 3% TCA in CH$_2$Cl$_2$. The resin is washed with CH$_2$Cl$_2$ to remove traces of acid, and the solid support treated with NH$_4$OH to cleave the product from the solid support. The ammonia solution is removed in vacuo to give the final compound composed of three different scaffolds (1: diethanolamine, 2: piperidinediol and 3: hydroxyprolinol) acylated with three different carboxylic acids (1: cyclohexane carboxylic acid, 2: thiophene carboxylic acid, and 3: 4-nitrobenzoic acid) and linked with two different substituted phosphoramidates (1–2: isopropoxyethylamine, and 2–3: 3-aminomethylpyridine).

EVALUATION

Procedure 1

Antimicrobial Assay

Staphylococcus aureus

Staphylococcus aureus is known to cause localized skin infections as a result of poor hygiene, minor trauma, psoriasis or eczema. It also causes respiratory infections, pneumonia, toxic shock syndrome and septicemia. It is a common cause of acute food poisoning. It exhibits rapid emergence of drug resistance to penicillin, cephalosporin, vancomycin and nafcillin.

In this assay, the strain S. aureus ATCC 25923 (American Type Culture Collection) is used in the bioassay. To initiate the exponential phase of bacterial growth prior to the assay, a sample of bacteria grown overnight at 37° C. in typtocase soy broth (BBL) is used to reinoculate sample wells of 96-well microtiter plates. The assays are carried out in the 96-well microtiter plates in 150 μL volume with approximately 1×10$^6$ cells per well.

Bacteria in typtocase soy broth (75 μL) is added to the compound mixtures of the invention in solution in 75μ water in the individual well of the microtiter plate. Final concentrations of the compound mixtures are 25 μM, 10 μM and 1 μM. Each concentration of the compound mixtures is assayed in triplicate. The plates are incubated at 37° C. and growth monitored over a 24 hour period by measuring the optical density at 595 nm using a BioRad model 3550 UV microplate reader. The percentage of growth relative to a well containing no compound is determined. Ampicillin and tetracycline antibiotic positive controls are concurrently tested in each screening assay.

PROCEDURE 2

Antimicrobial Mechanistic Assay

Bacterial DNA Gyrase

DNA gyrase is a bacterial enzyme which can introduce negative supercoils into DNA utilizing the free energy derived from ATP hydrolysis. This activity is critical during DNA replication and is a well characterized target for antibiotic inhibition of bacterial growth. In this assay, libraries of compounds of the invention are screened for inhibition of DNA gyrase. The assay measures the supercoiling of a relaxed plasmid by DNA gyrase as an electrophoretic shift on an agarose gel. Initially all library pools are screened for inhibitory activity at 30 μM and then a dose response analysis is effected with active subsets. Novobiocin, an antibiotic that binds to the β subunit of DNA gyrase is used as a positive control in the assay. The sensitivity of the DNA gyrase assay was determined by titrating the concentration of the know DNA gyrase inhibitor, Novobiocin, in the supercoiling assay. The IC$_{50}$ was determined to be 8 nM, sufficient to identify the activity of a single active species of comparable activity in a library having 30 μM concentration.

PROCEDURE 3

Use of a Combinatorial Library for Identifying of Metal Chelators and Imaging Agents This procedure is used to identify specific compounds of the invention contained in libraries of compounds which each contain a ring which contains an ultraviolet chromophore. The diversity groups attached to the compound bridge are selected from metal binders, coordinating groups such as amine, hydroxyl and carbonyl groups, and other groups having lone pairs of electrons, such that the oligomeric compounds of the invention can form coordination complexes with heavy metals and imaging agents. The procedure is used to identify oligomeric compounds of the invention for chelating and removing heavy metals from industrial broths, waste stream eluents, heavy metal poisoning of farm animals and other sources of contaminating heavy metals, and for use in identifying imaging agent carriers, such as carriers for technetium 99.

An aliquot of a test solution having the desired ion or imaging agent at a known concentration is added to an aliquot of standard solution of the pool of compounds of the invention being assayed. The UV spectrum of this aliquot is measured and is compared to the UV spectrum of a further aliquot of the same solution lacking the test ion or imaging agent. A shift in the extinction coefficient is indicative of binding of the metal ion or imaging ion to a compound in the library pool being assayed.

PROCEDURE 4

Assay of Combinatorial Library for PLA$_2$ Inhibitors

A preferred target for assay of combinatorially generated pools of compounds is the phospholipase A family. Phospholipases A$_2$ (PLA$_2$) are a family of enzymes that hydrolyze the sn-2 ester linkage of membrane phospholipids resulting in release of a free fatty acid and a lysophospholipid (Dennis, E. A., The Enzymes, Vol. 16, pp. 307–353, Boyer, P. D., ed., Academic Press, New York, 1983). Elevated levels of type II PLA$_2$ are correlated with a number of human inflammatory diseases. The PLA$_2$-catalyzed reaction is the rate-limiting step in the release of a number of pro-inflammatory mediators. Arachidonic acid, a fatty acid commonly linked at the sn-2 position, serves as a precursor to leukotrienes, prostaglandins, lipoxins and thromboxanes. The lysophospholipid can be a precursor to platelet-activating factor. PLA$_2$ is regulated by pro-inflammatory cytokines and, thus, occupies a central position in the inflammatory cascade (Dennis, ibid.; Glaser et al., *TiPs Reviews* 1992, 14, 92; and Pruzanski et al., *Inflammation* 1992, 16, 451). All mammalian tissues evaluated thus far have exhibited PLA$_2$ activity. At least three different types of PLA$_2$ are found in humans: pancreatic (type I), synovial fluid (type II) and cytosolic. Studies suggest that additional isoenzymes exist. Type I and type II, the secreted forms of PLA$_2$, share strong similarity with phospholipases isolated from the venom of snakes. The PLA$_2$ enzymes are important for normal functions including digestion, cellular membrane remodeling and repair, and in mediation of the inflammatory response. Both cytosolic and type II enzymes are of interest as therapeutic targets. Increased levels of the type II PLA$_2$ are correlated with a variety of inflammatory disorders including rheumatoid arthritis, osteoarthritis, inflammatory bowel disease and septic shock, suggesting that inhibitors of this enzyme would have therapeutic utility. Additional support for a role of PLA$_2$ in promoting the pathophysiology observed in certain chronic inflammatory disorders was the observation that injection of type II PLA$_2$ into the footpad of rats (Vishwanath et al., *Inflammation* 1988, 12, 549) or into the articular space of rabbits (Bomalaski et al., *J. Immunol.* 1991, 146, 3904) produced an inflammatory response. When the protein was denatured before injection, no inflammatory response was produced.

The type II PLA$_2$ enzyme from synovial fluid is a relatively small molecule (about 14 kD) and can be distinguished from type I enzymes (e.g. pancreatic) by the sequence and pattern of its disulfide bonds. Both types of enzymes require calcium for activity. The crystal structures of secreted $PLA_2$ enzymes from venom and pancreatic $PLA_2$, with and without inhibitors, have been reported (Scott et al., Science 1990, 250, 1541). Recently, the crystal structure of $PLA_2$ from human synovial fluid has been determined (Wery et al., Nature 1991, 352, 79). The structure clarifies the role of calcium and amino acid residues in catalysis. Calcium acts as a Lewis acid to activate the scissile ester carbonyl bond of 1,2-diacylglycerophospholipids and binds to the lipid, and a His-Asp side chain dyad acts as a general base catalyst to activate a water molecule nucleophile. This is consistent with the absence of any acyl enzyme intermediates, and is also comparable to the catalytic mechanism of serine proteases. The catalytic residues and the calcium ion are at the end of a deep cleft (ca. 14 Å) in the enzyme. The walls of this cleft contact the hydrocarbon portion of the phospholipid and are composed of hydrophobic and aromatic residues. The positively-charged amino-terminal helix is situated above the opening of the hydrophobic cleft. Several lines of evidence suggest that the N-terminal portion is the interfacial binding site (Achari et al., Cold Spring Harbor Symp. Quant. Biol. 1987, 52, 441; Cho et al., J. Biol. Chem. 1988, 263, 11237; Yang et al., Biochem. J. 1989, 262, 855; and Noel et al., J. Am. Chem. Soc. 1990, 112, 3704).

Much work has been reported in recent years on the study of the mechanism and properties of $PLA_2$-catalyzed hydrolysis of phospholipids. In in vitro assays, $PLA_2$ displays a lag phase during which the enzyme adsorbs to the substrate bilayer and a process called interfacial activation occurs. This activation may involve desolvation of the enzyme/lipid interface or a change in the physical state of the lipid around the cleft opening. Evidence favoring this hypothesis comes from studies revealing that rapid changes in $PLA_2$ activity occur concurrently with changes in the fluorescence of a membrane probe (Burack et al., Biochemistry 1993, 32, 583). This suggests that lipid rearrangement is occurring during the interfacial activation process. $PLA_2$ activity is maximal around the melting temperature of the lipid, where regions of gel and liquid-crystalline lipid coexist. This is also consistent with the sensitivity of $PLA_2$ activity to temperature and to the composition of the substrate, both of which can lead to structurally distinct lipid arrangements separated by a boundary region. Fluorescence microscopy was used to simultaneously identify the physical state of the lipid and the position of the enzyme during catalysis (Grainger et al., FEBS Lett. 1989, 252, 73). These studies clearly show that $PLA_2$ binds exclusively at the boundary region between liquid and solid phase lipid. While the hydrolysis of the secondary ester bond of 1,2-diacylglycerophospholipids catalyzed by the enzyme is relatively simple, the mechanistic and kinetic picture is clouded by the complexity of the enzyme-substrate interaction. A remarkable characteristic of $PLA_2$ is that maximal catalytic activity is observed on substrate that is aggregated (i.e. phospholipid above its critical micelle concentration), while low levels of activity are observed on monomeric substrate. As a result, competitive inhibitors of $PLA_2$ either have a high affinity for the active site of the enzyme before it binds to the substrate bilayer or partition into the membrane and compete for the active site with the phospholipid substrate. Although a number of inhibitors appear to show promising inhibition of $PLA_2$ in biochemical assays (Yuan et al., J. Am. Chem. Soc. 1987, 109, 8071; Lombardo et al., J. Biol. Chem. 1985, 260, 7234; Washburn et al., J. Biol. Chem. 1991, 266, 5042; Campbell et al., J. Chem. Soc., Chem. Commun. 1988, 1560; and Davidson et al., Biochem. Biophys. Res. Commun. 1986, 137, 587), reports describing in vivo activity are limited (Miyake et al., J. Pharmacol. Exp. Ther. 1992, 263, 1302).

In one preferred embodiment, oligomeric compounds of the invention are selected for their potential to interact with, and preferably inhibit, the enzyme $PLA_2$. Thus, compounds of the invention can be used for topical and/or systemic treatment of inflammatory diseases including atopic dermatitis and inflammatory bowel disease. In selecting the functional groups, advantage can be taken of $PLA_2$'s preference for anionic vesicles over zwitterionic vesicles. Preferred compounds of the invention for assay for $PLA_2$ include those having aromatic diversity groups to facilitate binding to the cleft of the $PLA_2$ enzyme (Oinuma et al., J. Med. Chem. 1991, 34, 2260; Marki et al., Agents Actions 1993, 38, 202; and Tanaka et al., J. Antibiotics 1992, 45, 1071). Benzyl and 4-hexylbenzyl groups are preferred aromatic diversity groups. $PLA_2$-directed oligoneric compounds of the invention can further include hydrophobic functional groups such as tetraethylene glycol groups. Since the $PLA_2$ enzyme has a hydrophobic channel, hydrophobicity is believed to be an important property of inhibitors of the enzyme.

After each round of synthesis as described in the above examples, the resulting pools of compounds are screened for inhibition of human type II $PLA_2$ enzymatic activity. The assay is effected at the conclusion of synthesis to identify the wining compounds of that synthesis. Concurrently, the libraries additionally can be screened in other in vitro assays to determine further mechanisms of inhibition.

The pools of the oligomeric compound libraries are screened for inhibition of $PLA_2$ in the assay using E. coli labeled with $^3$H-oleic acid (Franson et al., J. Lipid Res. 1974, 15, 380; and Davidson et al., J. Biol. Chem. 1987, 262, 1698) as the substrate. Type II $PLA_2$ (originally isolated from synovial fluid), expressed in a baculovirus system and partially purified, serves as a source of the enzyme. A series of dilutions of each the library pools is done in water: 10 μl of each pool is incubated for 5 minutes at room temperature with a mixture of 10 μl $PLA_2$, 20 μl 5×$PLA_2$ Buffer (500 mM Tris 7.0–7.5, 5 mM $CaCl_2$), and 50 μl water. Samples of each pool are run in duplicate. At this point, 10 μl of $^3$H E. coli cells is added. This mixture is incubated at 37° C. for 15 minutes. The enzymatic reaction is stopped with the addition of 50 μl 2M HCl and 50 μl fatty-acid-free BSA (20 mg/ml PBS), vortexed for 5 seconds, and centrifuged at high speed for 5 minutes. 165 μl of each supernate is then put into a scintillation vial containing 6 ml of scintillant (ScintiVerse) and cpms are measured in a Beckman Liquid Scintillation Counter. As a control, a reaction without the combinatorial pool is run alongside the other reactions as well as a baseline reaction containing no oligomeric compounds as well as no $PLA_2$ enzyme. CPMs are corrected for by subtracting the baseline from each reaction data point.

Confirmation of the "winners" is made to confirm that the oligomeric compound binds to enzyme rather than substrate and that the inhibition of any oligomeric compound selected is specific for type II $PLA_2$. An assay using $^{14}$C-phosphatidyl ethanolamine ($^{14}$C-PE) as substrate, rather than E. coli membrane, is used to insure enzyme rather than substrate specificity. Micelles of $^{14}$C-PE and deoxycholate are incubated with the enzyme and oligomer. $^{14}$C-labeled arachidonic acid released as a result of $PLA_2$-catalyzed hydrolysis is separated from substrate by thin layer chromatography and the radioactive product is quantitated. The "winner" is compared to phosphatidyl ethanolamine, the preferred substrate of human type II PLA$_2$, to confirm its activity. PLA$_2$ from other sources (snake venom, pancreatic, bee venom) and phospholipase C, phospholipase D and lysophospholipase can be used to further confirm that the inhibition is specific for human type II PLA$_2$.

PROCEDURE 5
Probes for the Detection of Specific Proteins and mRNA in Biological Samples For the reliable, rapid, simultaneous quantification of multiple varieties of proteins or mRNA in a biological sample without the need to purify the protein or mRNA from other cellular components, a protein or mRNA of interest from a suitable biological sample, i.e., a blood borne virus, a bacterial pathogen product in stool, urine and other like biological samples, is identified using standard microbiological techniques. A probe comprising an oligomeric compound of the invention is identified by a combinatorial search as noted in the above examples. Preferred for the mRNA probe are compounds synthesized to include "nucleobase" diversity groups (adenine, guanine, thymine and cytosine as the letters) complementary to at least a portion of the nucleic acid sequence of the mRNA. Preferred for the protein probe are compounds synthesized to include chemical functional groups that act as hydrogen bond donors and acceptors, sulfhydryl groups, hydrophobic lipophilic moieties capable of hydrophobic interactions groups and groups capable of ionic interactions. The probe is immobilized on insoluble CPG solid support utilizing the procedure of Pon, R. T., Protocols for Oligonucleotides and Analogs, Agrawal, S., Ed., Humana Press, Totowa, N.J., 1993, p 465–496. A known aliquot of the biological sample under investigation is incubated with the insoluble CPG support having the probe thereon for a time sufficient to hybridize the protein or mRNA to probe and thus to link them via the probe to the solid support. This immobilizes protein or mRNA present in the sample to the CPG support. Other non-immobilized materials and components are then washed off the CPG with a wash media suitable for use with the biological sample. The mRNA on the support is labeled with ethidium bromide, biotin or a commercial radionucleotide and the amount of label immobilized on the CPG support is measured to indicate the amount of mRNA present in the biological sample. In a similar a protein is also labeled and quantified.

PROCEDURE 6
Leukotriene B$_4$ Assay

Leukotriene B$_4$ (LTB$_4$) has been implicated in a variety of human inflammatory diseases, and its pharmacological effects are mediated via its interaction with specific surface cell receptors. Library subsets are screened for competitive inhibition of radiolabeled LTB$_4$ binding to a receptor preparation.

A Nenquest™ Drug Discovery System Kit (NEN Research Products, Boston, Mass.) is used to select an inhibitor of the interaction of Leukotriene B$_4$ (LTB$_4$) with receptors on a preparation of guinea pig spleen membrane. [$^3$H] Leukotriene B$_4$ reagent is prepared by adding 5 mL of ligand diluent (phosphate buffer containing NaCl, MgCl$_2$, EDTA and Bacitracin, pH 7.2) to 0.25 mL of the radioligand. The receptor preparation is made by thawing the concentrate, adding 35 mL of ligand diluent and swirling gently in order to resuspend the receptor homogeneously. Reagents are kept on ice during the course of the experiment, and the remaining portions are stored at −20° C.

Library subsets prepared as per general procedure of examples above are diluted to 5 μM, 50 μM and 500 μM in phosphate buffer (1×PBS, 0.1% azide and 0.1% BSA, pH 7.2), yielding final test concentrations of 0.5 μM, 5 μM and 50 μM, respectively. Samples are assayed in duplicate. [$^3$H] LTB$_4$ (25 μL) is added to 25 μL of either appropriately diluted standard (unlabeled LTB$_4$) or library subset. The receptor suspension (0.2 mL) is added to each tube. Samples are incubated at 4° C. for 2 hours. Controls include [$^3$H] LTB$_4$ without receptor suspension (total count vials), and sample of ligand and receptor without library molecules (standard).

After the incubation period, the samples are filtered through GF/B paper that had been previously rinsed with cold saline. The contents of each tube are aspirated onto the filter paper to remove unbound ligand from the membrane preparation, and the tubes washed (2×4 mL) with cold saline. The filter paper is removed from the filtration unit and the filter disks are placed in appropriate vials for scintillation counting. Fluor is added, and the vials shaken and allowed to stand at room temperature for 2 to 3 hours prior to counting. The counts/minute (cpm) obtained for each sample are subtracted from those obtained from the total count vials to determine the net cpm for each sample. The degree of inhibition of binding for each library subset is determined relative to the standard (sample of ligand and receptor without library molecules).

Each of the published documents mentioned in this specification are herein incorporated in their entirety.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. An oligomeric compound comprising a plurality of aminodiol monomer subunits joined by linking groups, wherein each of said aminodiol monomer subunits has one of the structures II, III, IV or VI:

II
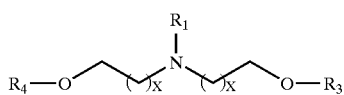

III
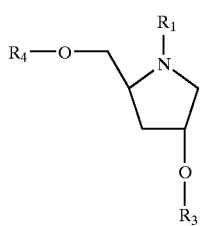

IV
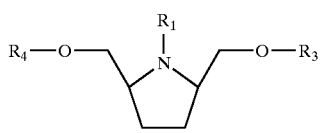

V
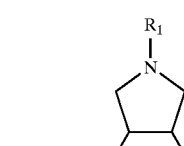

VI
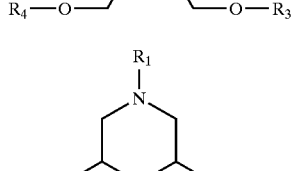

wherein:

each x is, independently, 0 to 5;

$R_1$ is —T—L or a base labile protecting group;

T is a single bond, a methylene group or a group having formula:

wherein:

$R_{10}$ is =O, =S, or =NR$_{11}$;

$R_5$ and E, independently, are a single bond, CH=CH, C≡C, O, S, NR$_{11}$, or $C_6$–$C_{14}$ aryl;

each $R_6$, $R_7$, $R_8$, $R_9$, $R_{11}$, $R_{12}$ and $R_{13}$ are, independently, H, alkyl or haloalkyl having 1 to about 10 carbon atoms, alkenyl having 2 to about 10 carbon atoms, alkenyl having 2 to about 10 carbon atoms, or aryl having 7 to about 14 carbon atoms;

m and n, independently, are 0 to 5;

p is 0 or 1;

q is 1 to about 10;

L is H, substituted or unsubstituted $C_2$–$C_{10}$ alkyl, substituted or unsubstituted $C_2$–$C_{10}$ alkenyl, substituted or unsubstituted $C_2$–$C_{10}$ alkynyl, substituted or unsubstituted $C_4$–$C_7$ carbocyclic alkyl, substituted or unsubstituted $C_4$–$C_7$ carbocyclic alkenyl, substituted or unsubstituted $C_4$–$C_7$ carbocyclic alkynyl, substituted or unsubstituted $C_6$–$C_{14}$ aryl, an ether having 2 to 10 carbon atoms and 1 to 4 oxygen or sulfur atoms, a nitrogen containing heterocycle, a sulfur containing heterocycle, an oxygen containing heterocycle, a metal coordination group, a conjugate group, halogen, hydroxyl (OH), thiol (SH), keto (C=O), carboxyl (COOH), amide (CONR$_{12}$), amidine (C(=NH)NR$_{12}$R$_{13}$), guanidine (NHC(=NH)NR$_{12}$R$_{13}$), glutamyl (R$_{12}$OOCCH(NR$_{12}$R$_{13}$)(CH$_2$)$_2$C(=O), nitrate (ONO$_2$), nitro (NO$_2$), nitrile (CN), trifluoromethyl (CF$_3$), trifluoromethoxy (OCF$_3$), O-alkyl, S-alkyl, NH-alkyl, N-dialkyl, O-aralkyl, S-aralkyl, NH-aralkyl, amino (NH$_2$), azido (N$_3$), hydrazino (NHNH$_2$), hydroxylamino (ONH$_2$), sulfoxide (SO), sulfone (SO$_2$), sulfide (S—), disulfide (S—S), silyl, a nucleosidic base, an amino acid side chain, a carbohydrate, a biopharmaceutically active moiety, or group capable of hydrogen bonding where the substituent groups are selected from hydroxyl, amino, alkoxy, alcohol, benzyl, phenyl, nitro, thiol, thioalkoxy, halogen, alkyl, aryl, alkenyl, and alkynyl groups;

$R_2$ is hydrogen or $C_1$–$C_{10}$ alkyl;

$R_3$ and $R_4$ are independently hydrogen, an acid labile hydroxyl protecting group, a linking group or a conjugate group, wherein said linking group has the formula:

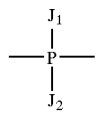

wherein:

$J_1$ is =O or =S;

$J_2$ is OH or N(Y$_0$)T$_0$;

Y$_0$ is H or (Q$_2$)$_j$—Z$_2$;

T$_0$ is (Q$_1$)$_k$—Z$_1$, or together Y$_0$ and T$_0$ are joined in a nitrogen heterocycle;

Q$_1$ and Q$_2$ independently are $C_2$–$C_{10}$ alkyl, $C_2$–$C_{10}$ alkenyl, $C_2$–$C_{10}$ alkynyl, $C_4$–$C_7$ carbocylo alkyl $C_4$–$C_7$ carbocylo alkenyl, a heterocycle, an ether having 2 to 10 carbon atoms and 1 to 4 oxygen or sulfur atoms, a polyalky glycol, or $C_7$–$C_{14}$ aralkyl;

j and k independently are 0 or 1;

$Z_1$ and $Z_2$ independently are H, $C_1$–$C_2$ alkyl, $C_2$–$C_{20}$ alkenyl, $C_2$–$C_{20}$ alkynyl, $C_6$–$C_{14}$ aryl, $C_7$–$C_{15}$ aralkyl, halogen, CH=O, OR$_{12}$, SR$_{12}$, NR$_{12}$R$_{13}$, C(=NH)NR$_{12}$R$_{13}$ CH(NR$_{12}$R$_{13}$), NHC(=NH) NR$_{12}$R$_{13}$, CH(NH$_2$)C(=O)OH, C(=O)NR$_{12}$R$_{13}$, C(=O)OR$_{12}$, a metal coordination group, a reporter group, a nitrogen-containing heterocycle, a purine, a pyrimidine, a phosphate group, a polyether group, or a polyethylene glycol group; and provided that at least one of said aminodiol monomer subunits in said oligomeric compound does not have structure III.

2. The oligomeric compound of claim 1 wherein said $J_1$ is =O or =S and said $J_2$ is OH.

3. The oligomeric compound of claim 1 wherein said $J_1$ is =O, said $J_2$ is N(Y$_0$)T$_0$ and at least two of said N(Y$_0$)T$_0$ are the same.

4. The oligomeric compound of claim 1 wherein said $J_1$ is =O, said $J_2$ is N(Y$_0$)T$_0$ and wherein at least two of said N(Y$_0$)T$_0$ are different.

5. The oligomeric compound of claim 1 wherein each said $R_1$ are the same.

6. The oligomeric compound of claim 1 wherein at least two of said $R_1$ are different.

7. The oligomeric compound of claim 1 wherein each of said aminodiol monomer subunits are the same.

8. The oligomeric compound of claim 1 wherein at least two of said aminodiol monomer subunits are different.

9. A method for preparing an oligomer comprising:
(a) selecting an aminodiol monomer subunit having the structure II, III, IV, V, or VI;

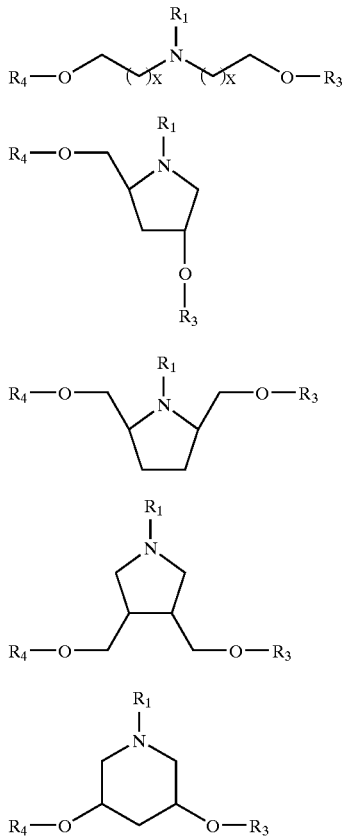

wherein:

each x is, independently, 0 to 5;

$R_1$ is a base labile amino protecting group;

$R_2$ is hydrogen or $C_1$–$C_{10}$ alkyl;

one of $R_3$ or $R_4$ is hydrogen or an activated phosphite group and the other of $R_3$ or $R_4$ is an acid labile hydroxyl protecting group;

(b) attaching said aminodiol monomer subunit to a solid support to form a solid support bound aminodiol monomer subunit;

(c) treating said acid labile hydroxyl protecting group with a dilute acid to form a free hydroxyl group;

(d) reacting said free hydroxyl group with a further aminodiol monomer subunit having structure I, I, III, IV, V, or VI thereby forming an oligomeric compound bound to said solid support, said oligomeric compound containing a phosphite linkage;

(e) optionally iteratively repeating steps (c) and (d) to increase the length of the oligomeric compound bound to said solid support;

(f) optionally, prior to step (c) or after step (d) oxidizing said phosphite linkage to form a phosphate liking group wherein said linking groups are selected having formula:

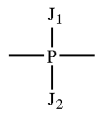

wherein:

$J_1$ is =O or =S;

$J_2$ is OH or $N(Y_0)T_0$;

$Y_0$ is H or $(Q_2)_j$—$Z_2$;

$T_0$ is $(Q_1)_k$—$Z_1$, or together $Y_0$ and $T_0$ are joined in a nitrogen heterocycle;

$Q_1$ and $Q_2$ independently are $C_2$–$C_{10}$ alkyl, $C_2$–$C_{10}$ alkenyl, $C_2$–$C_{10}$ alkynyl, $C_4$–$C_7$ carbocylo alkyl $C_4$–$C_7$ carbocylo alkenyl, a heterocycle, an ether having 2 to 10 carbon atoms and 1 to 4 oxygen or sulfur atoms, a polyalkyl glycol, or $C_7$–$C_{14}$ aralkyl;

j and k independently are 0 or 1;

$Z_1$ and $Z_2$ independently are H, $C_1$–$C_2$ alkyl, $C_2$–$C_{20}$ alkenyl, $C_2$–$C_{20}$ alkynyl, $C_6$–$C_{14}$ aryl, $C_7$–$C_{15}$ aralkyl, halogen, CH=O, $OR_{12}$, $SR_{12}$, $NR_{12}R_{13}$, C(=NH)$NR_{12}R_{13}$, $CH(NR_{12}R_{13})$, NHC(=NH)$NR_{12}R_{13}$, $CH(NH_2)C(=O)OH$, C(=O)$NR_{12}R_{13}$, C(=O)$OR_{12}$, a metal coordination group, a reporter group, a nitrogen-containing heterocycle, a purine, a pyrimidine, a phosphate group, a polyether group, or a polyethylene glycol group, provided that at least one of said aminodiol monomer subunits in said oligomeric compound does not have structure III;

(g) prior to step (e) or after step (f) contacting said solid support bound aminodiol monomer subunit or said support bound oligomeric compound with a base to remove said base labile or protecting group to form the solid support bound aminodiol monomer subunit or support bound oligomeric compound having a free amine, and derivatizing said free amine with a group of the formula:

—T—L wherein:

T is a single bond, a methylene group or a group having formula:

wherein:

$R_{10}$ is =O, =S, or =$NR_{11}$;

$R_5$ and E, independently, are a single bond, CH=CH, C≡C, O, S, $NR_{11}$, or $C_6$–$C_{14}$ aryl;

each $R_6$, $R_7$, $R_8$, $R_9$, $R_{11}$, $R_{12}$ and $R_{13}$ are, independently, H, alkyl or haloalkyl having 1 to about 10 carbon atoms alkenyl having 2 to about 10 carbon atoms, alkynyl having 2 to about 10 carbon atoms, or aryl having 7 to about 14 carbon atoms;

m and n, independently, are 0 to 5;

p is 0 or 1;

q is 1 to about 10;

L is H, substituted or unsubstituted $C_2$–$C_{10}$ alkyl, substituted or unsubstituted $C_2$–$C_{10}$ alkenyl, substituted or unsubstituted $C_2$–$C_{10}$ alkynyl, substituted or unsubstituted $C_4$–$C_7$ carbocyclic alkyl, substituted or unsubstituted $C_4$–$C_7$ carbocyclic alkenyl, substituted or unsubstituted $C_4$–$C_7$ carbocyclic alkynyl, substituted or unsubstituted $C_6$–$C_{14}$ aryl, an ether having 2 to 10 carbon atoms and 1 to 4 oxygen or sulfur atoms, a nitrogen containing heterocycle, a sulfur containing heterocycle, an oxygen containing heterocycle, a metal coordination group, a conjugate group, halogen, hydroxyl (OH), thiol (SH), keto (C=O), carboxyl (COOH), amide ($CONR_{12}$), amidine (C(=NH)$NR_{12}R_{13}$), guanidine (NHC(=NH)$NR_{12}R_{13}$), glutamyl ($R_{12}OOCCH(NR_{12}R_{13})(CH_2)_2C$(=O), nitrate ($ONO_2$), nitro ($NO_2$), nitrile (CN), trifluoromethyl ($CF_3$), trifluoromethoxy ($OCF_3$), O-alkyl, S-alkyl, NH-alkyl, N-dialkyl, O-aralkyl, S-aralkyl, NH-aralkyl, amino ($NH_2$), azido ($N_3$), hydrazino ($NHNH_2$), hydroxylamino ($ONH_2$), sulfoxide (SO), sulfone ($SO_2$), sulfide (S—), disulfide (S—S), silyl, a nucleosidic base, an amino acid side chain, a carbohydrate, a biopharmaceutically active moiety, or group capable of hydrogen bonding where the substituent groups are selected from hydroxyl, amino, alkoxy, alcohol, benzyl phenyl, nitro, thiol, thioalkoxy, halogen, alkyl, aryl, alkenyl, and alkynyl groups;

(h) optionally repeating steps (c) and (d) followed by step (g) to increase the length of the oligomeric compound bound to said solid support;

(i) treating said oligomeric compound bound to said solid support with acid to deprotect any protecting groups; and (j) cleaving said oligomeric compound from said solid support.

10. The process of claim 9 wherein said step (g) is conducted after said step (b).

11. The process of claim 9 wherein said step (g) is conducted prior to step (d) for the addition of at least one monomeric subunit to said oligomeric compound.

12. The process of claim 9 wherein said step (g) is conducted prior to each iteration of said step (d).

13. The process of claim 9 wherein said step (g) is conducted only after at least one iteration of said step (e).

14. The process of claim 9 wherein said step (g) is conducted after said step (f) for the addition of at least one monomeric subunit to said oligomeric compound.

* * * * *

UNITED STATES PATENT AND TRADEMARK OFFICE
CERTIFICATE OF CORRECTION

PATENT NO. : 6,828,427 B1 Page 1 of 1
APPLICATION NO. : 08/973381
DATED : December 7, 2004
INVENTOR(S) : Normand Hebert It is certified that error appears in the above-identified patent and that said Letters Patent is hereby corrected as shown below:

Title page,
Item [56], References Cited, OTHER PUBLICATIONS,
"Ezquerra" reference, delete "Pyrrolidine-2.5" and insert -- Pyrrolidine-2,5 --;

Column 87,
Line 56, delete "alkenyl" and insert -- alkynyl --;

Column 89,
Line 65, delete "liking" and insert -- linking --;

Column 90,
Line 37, delete "or".

Signed and Sealed this

Twentieth Day of June, 2006

JON W. DUDAS
*Director of the United States Patent and Trademark Office*

SEQUENCE LISTING

<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 1
ttgcttccat cttcctcgtc                                            20